US011819236B2

(12) United States Patent
Kelly et al.

(10) Patent No.: US 11,819,236 B2
(45) Date of Patent: Nov. 21, 2023

(54) TISSUE-REMOVING CATHETER

(71) Applicant: MEDTRONIC VASCULAR, INC., Santa Rosa, CA (US)

(72) Inventors: Tomas Kelly, Galway (IE); John Kelly, Galway (IE); Aram Jamous, Athenry (IE); Matthew Fleming, Roscommon (IE); Ronan Finn, Galway (IE); Bryan Hansen, Galway (IE); Niall Kelly, Galway (IE); Damian Cunniffe, Galway (IE); Tommy Hayden, Galway (IE); John Clifford, Galway (IE); Michael Sayers, Limerick (IE); Eoin Walsh, Galway (IE); Shane Cooney, Galway (IE); Cian Walsh, Galway (IE); Mick Donegan, Galway (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 166 days.

(21) Appl. No.: 16/874,372

(22) Filed: May 14, 2020

(65) Prior Publication Data

US 2020/0360047 A1 Nov. 19, 2020

Related U.S. Application Data

(60) Provisional application No. 62/849,627, filed on May 17, 2019.

(51) Int. Cl.
*A61B 17/3207* (2006.01)
*A61B 17/00* (2006.01)

(52) U.S. Cl.
CPC ........... *A61B 17/320758* (2013.01); *A61B 17/320783* (2013.01); *A61B 2017/00075* (2013.01);

(Continued)

(58) Field of Classification Search
CPC .... A61B 17/320758; A61B 17/320783; A61B 2017/00075; A61B 2017/320716; A61B 2017/32775; A61B 2017/320791
See application file for complete search history.

(56) References Cited

U.S. PATENT DOCUMENTS

| 182,499 A | 9/1876 | Waterman |
| 639,898 A | 12/1899 | Huenefeld |

(Continued)

FOREIGN PATENT DOCUMENTS

| AU | 2007271820 A1 | 2/2009 |
| AU | 2009255433 A1 | 11/2010 |

(Continued)

OTHER PUBLICATIONS

US 7,316,661 B2, 01/2008, Zadno (withdrawn)

(Continued)

*Primary Examiner* — Tuan V Nguyen
(74) *Attorney, Agent, or Firm* — Stinson LLP

(57) ABSTRACT

A tissue-removing catheter for removing tissue in a body lumen includes a catheter body assembly having an axis and proximal and distal end portions spaced apart from one another along the axis. At least a portion of the catheter body assembly is sized and shaped to be received in the body lumen. A handle is mounted to the proximal end portion of the catheter body assembly and operable to cause rotation of the catheter body assembly. The handle includes internal handle components that interface with the catheter body assembly. The internal handle components provide at least four interface locations spaced axially along the catheter body assembly. A tissue-removing element is mounted on the distal end portion of the catheter body assembly. The tissue-removing element is configured to remove the tissue (Continued)

as the tissue-removing element is rotated by the catheter body assembly within the body lumen.

20 Claims, 63 Drawing Sheets

(52) U.S. Cl.
CPC ............. *A61B 2017/320716* (2013.01); *A61B 2017/320775* (2013.01); *A61B 2017/320791* (2013.01)

(56) References Cited

U.S. PATENT DOCUMENTS

| | | | |
|---|---|---|---|
| 970,748 A | 9/1910 | Post | |
| 1,045,879 A | 12/1912 | Peterson | |
| 2,099,368 A | 11/1937 | Lucien | |
| 2,203,121 A | 6/1940 | Philipp | |
| 2,280,657 A | 4/1942 | Mccandliss | |
| 2,282,688 A | 5/1942 | Zuck | |
| 2,303,149 A | 11/1942 | Verhagen | |
| 2,303,151 A | 11/1942 | Watkins et al. | |
| 2,398,405 A | 4/1946 | Brooks | |
| 2,429,356 A | 10/1947 | Hicks | |
| 2,579,791 A | 12/1951 | Carter | |
| 2,742,881 A | 4/1956 | Rideout et al. | |
| 3,141,201 A | 7/1964 | Hermann et al. | |
| 3,166,512 A | 1/1965 | Mizuno | |
| 4,445,509 A | 5/1984 | Auth | |
| 4,631,052 A | 12/1986 | Kensey et al. | |
| 4,650,466 A | 3/1987 | Luther | |
| 4,679,557 A | 7/1987 | Opie et al. | |
| 4,729,763 A | 3/1988 | Henrie | |
| 4,784,636 A | 11/1988 | Rydell | |
| 4,795,438 A | 1/1989 | Kensey et al. | |
| 4,829,999 A | 5/1989 | Auth | |
| 4,850,957 A | 7/1989 | Summers | |
| 4,857,046 A | 8/1989 | Stevens et al. | |
| 4,883,460 A | 11/1989 | Zanetti | |
| 4,886,061 A | 12/1989 | Fischell et al. | |
| 4,890,611 A | 1/1990 | Monfort et al. | |
| 4,895,560 A | 1/1990 | Papantonakos | |
| 4,917,085 A | 4/1990 | Smith | |
| 4,950,238 A | 8/1990 | Sullivan | |
| 4,990,134 A | 2/1991 | Auth | |
| 5,030,201 A | 7/1991 | Palestrant | |
| 5,041,082 A | 8/1991 | Shiber | |
| 5,049,124 A | 9/1991 | Bales, Jr. | |
| 5,059,203 A | 10/1991 | Husted | |
| 5,100,425 A | 3/1992 | Fischell et al. | |
| 5,113,613 A | 5/1992 | Ackeret | |
| 5,116,350 A | 5/1992 | Stevens | |
| 5,116,352 A | 5/1992 | Schnepp et al. | |
| 5,120,516 A | 6/1992 | Ham et al. | |
| 5,126,667 A | 6/1992 | Kataoka et al. | |
| 5,129,698 A | 7/1992 | Cohrs et al. | |
| 5,129,734 A | 7/1992 | Van Erden | |
| 5,158,564 A | 10/1992 | Schnepp et al. | |
| 5,160,342 A | 11/1992 | Reger et al. | |
| 5,165,187 A | 11/1992 | Shahidi Hamedani et al. | |
| 5,170,805 A | 12/1992 | Kensey et al. | |
| 5,176,693 A | 1/1993 | Pannek, Jr. | |
| 5,178,625 A | 1/1993 | Groshong | |
| 5,193,735 A | 3/1993 | Knight | |
| 5,195,954 A | 3/1993 | Schnepp et al. | |
| 5,221,087 A | 6/1993 | Fenton et al. | |
| 5,242,460 A | 9/1993 | Klein et al. | |
| 5,242,461 A | 9/1993 | Kortenbach et al. | |
| 5,250,060 A | 10/1993 | Carbo | |
| 5,267,955 A | 12/1993 | Hanson | |
| 5,287,858 A | 2/1994 | Hammerslag et al. | |
| 5,295,958 A | 3/1994 | Shturman | |
| 5,308,354 A | 5/1994 | Zacca et al. | |
| 5,312,427 A | 5/1994 | Zacca et al. | |
| 5,314,407 A * | 5/1994 | Auth | A61B 17/320758 606/159 |
| 5,314,438 A | 5/1994 | Shturman | |
| 5,318,576 A | 6/1994 | Plassche, Jr. et al. | |
| 5,344,395 A | 9/1994 | Whalen et al. | |
| 5,356,481 A | 10/1994 | Yoshimura et al. | |
| 5,360,432 A | 11/1994 | Shturman | |
| 5,366,463 A | 11/1994 | Ryan | |
| 5,366,464 A | 11/1994 | Belknap | |
| 5,376,077 A | 12/1994 | Gomringer | |
| 5,376,100 A | 12/1994 | Lefebvre | |
| 5,417,703 A | 5/1995 | Brown et al. | |
| 5,490,859 A | 2/1996 | Mische et al. | |
| 5,501,694 A | 3/1996 | Ressemann et al. | |
| 5,507,760 A | 4/1996 | Wynne et al. | |
| 5,507,761 A | 4/1996 | Duer | |
| 5,507,795 A | 4/1996 | Chiang et al. | |
| 5,512,044 A | 4/1996 | Duer | |
| 5,540,707 A | 7/1996 | Ressemann et al. | |
| 5,554,163 A | 9/1996 | Shtruman | |
| 5,569,275 A | 10/1996 | Kotula et al. | |
| 5,569,276 A | 10/1996 | Jang et al. | |
| 5,571,136 A | 11/1996 | Weaver | |
| 5,584,843 A | 12/1996 | Wulfman et al. | |
| 5,626,562 A | 5/1997 | Castro | |
| 5,628,761 A | 5/1997 | Rizik | |
| 5,632,755 A * | 5/1997 | Nordgren | A61B 17/32075 606/159 |
| 5,634,897 A | 6/1997 | Dance et al. | |
| 5,667,490 A | 9/1997 | Keith et al. | |
| 5,681,336 A | 10/1997 | Clement et al. | |
| 5,685,718 A | 11/1997 | Mcclintic | |
| 5,701,119 A | 12/1997 | Jurras, III | |
| 5,723,390 A | 3/1998 | Kijima et al. | |
| 5,728,063 A | 3/1998 | Preissman et al. | |
| 5,728,123 A | 3/1998 | Lemelson et al. | |
| 5,728,129 A | 3/1998 | Summers | |
| 5,766,190 A | 6/1998 | Wulfman | |
| 5,766,192 A | 6/1998 | Zacca | |
| 5,779,721 A | 7/1998 | Nash | |
| 5,792,157 A | 8/1998 | Mische et al. | |
| 5,800,083 A | 9/1998 | Gaarder et al. | |
| 5,836,868 A | 11/1998 | Ressemann et al. | |
| 5,836,957 A | 11/1998 | Schulz et al. | |
| 5,843,103 A | 12/1998 | Wulfman | |
| 5,843,150 A | 12/1998 | Dreessen et al. | |
| 5,855,601 A | 1/1999 | Bessler et al. | |
| 5,868,767 A | 2/1999 | Farley et al. | |
| 5,895,397 A | 4/1999 | Jang et al. | |
| 5,895,399 A | 4/1999 | Barbut et al. | |
| 5,895,400 A | 4/1999 | Abela | |
| 5,895,402 A | 4/1999 | Hundertmark et al. | |
| 5,897,566 A | 4/1999 | Shturman et al. | |
| 5,897,567 A | 4/1999 | Ressemann et al. | |
| 5,904,698 A | 5/1999 | Thomas et al. | |
| 5,916,227 A | 6/1999 | Keith et al. | |
| 5,916,234 A | 6/1999 | Lam | |
| 5,919,200 A | 7/1999 | Stambaugh et al. | |
| 5,925,055 A | 7/1999 | Adrian et al. | |
| 5,938,670 A | 8/1999 | Keith et al. | |
| 5,954,747 A | 9/1999 | Lee | |
| 5,961,534 A | 10/1999 | Banik et al. | |
| 5,976,165 A | 11/1999 | Ball et al. | |
| 5,989,208 A | 11/1999 | Nita | |
| 5,997,557 A | 12/1999 | Barbut et al. | |
| 6,010,449 A | 1/2000 | Selmon et al. | |
| 6,010,622 A | 1/2000 | Chinn et al. | |
| 6,015,420 A | 1/2000 | Wulfman et al. | |
| 6,027,450 A | 2/2000 | Brown et al. | |
| 6,039,747 A | 3/2000 | Shturman et al. | |
| 6,059,812 A | 5/2000 | Clerc et al. | |
| 6,077,282 A | 6/2000 | Shturman et al. | |
| 6,080,171 A | 6/2000 | Keith et al. | |
| RE36,764 E | 7/2000 | Zacca et al. | |
| 6,083,228 A | 7/2000 | Michelson | |
| 6,090,135 A | 7/2000 | Plaia et al. | |
| 6,093,157 A | 7/2000 | Chandrasekaran | |
| 6,096,054 A | 8/2000 | Wyzgala et al. | |
| 6,099,534 A | 8/2000 | Bates et al. | |

(56) References Cited

U.S. PATENT DOCUMENTS

| | | |
|---|---|---|
| 6,113,579 A | 9/2000 | Eidenschink et al. |
| 6,113,613 A | 9/2000 | Spaulding |
| 6,113,614 A | 9/2000 | Mears |
| 6,113,615 A | 9/2000 | Wulfman |
| 6,120,516 A | 9/2000 | Selmon et al. |
| 6,120,517 A | 9/2000 | Daum et al. |
| 6,126,667 A | 10/2000 | Barry et al. |
| 6,129,698 A | 10/2000 | Beck |
| 6,129,734 A | 10/2000 | Shturman et al. |
| 6,132,444 A | 10/2000 | Shturman |
| 6,146,395 A | 11/2000 | Kanz |
| 6,156,046 A | 12/2000 | Passafaro et al. |
| 6,165,187 A | 12/2000 | Reger |
| 6,165,209 A | 12/2000 | Patterson et al. |
| 6,183,487 B1 | 2/2001 | Berry |
| 6,193,735 B1 | 2/2001 | Stevens |
| 6,217,595 B1 | 4/2001 | Shturman et al. |
| 6,221,015 B1 | 4/2001 | Yock |
| 6,221,087 B1 | 4/2001 | Anderson et al. |
| 6,235,042 B1 | 5/2001 | Katzman |
| 6,245,007 B1 | 6/2001 | Bedingham |
| 6,251,121 B1 | 6/2001 | Saadat |
| 6,258,052 B1 | 7/2001 | Milo |
| 6,266,550 B1 | 7/2001 | Selmon et al. |
| 6,270,509 B1 | 8/2001 | Berry |
| 6,295,712 B1 | 10/2001 | Shturman et al. |
| 6,299,623 B1 | 10/2001 | Wulfman |
| 6,300,434 B1 | 10/2001 | Schwager et al. |
| 6,306,151 B1 | 10/2001 | Lary |
| 6,312,444 B1 | 11/2001 | Barbut |
| 6,319,242 B1 | 11/2001 | Patterson et al. |
| 6,328,750 B1 | 12/2001 | Berry |
| 6,343,605 B1 | 2/2002 | Lafontaine |
| 6,375,609 B1 | 4/2002 | Hastings et al. |
| 6,391,832 B2 | 5/2002 | Lyons et al. |
| 6,398,798 B2 | 6/2002 | Selmon et al. |
| 6,400,980 B1 | 6/2002 | Lemelson |
| 6,416,523 B1 | 7/2002 | Lafontaine |
| 6,416,526 B1 | 7/2002 | Wyzgala et al. |
| 6,425,904 B1 | 7/2002 | Lemelson |
| 6,428,552 B1 | 8/2002 | Sparks et al. |
| 6,434,507 B1 | 8/2002 | Clayton et al. |
| 6,436,111 B1 | 8/2002 | Kadavy et al. |
| 6,440,503 B1 | 8/2002 | Merdan et al. |
| 6,443,967 B1 | 9/2002 | Kadavy et al. |
| 6,443,979 B1 | 9/2002 | Stalker et al. |
| 6,451,037 B1 | 9/2002 | Chandraskaran et al. |
| 6,461,383 B1 | 10/2002 | Gesswein et al. |
| 6,468,227 B2 | 10/2002 | Zimmon |
| 6,475,225 B1 | 11/2002 | Wulfman et al. |
| 6,478,807 B1 | 11/2002 | Foreman et al. |
| 6,482,209 B1 | 11/2002 | Engh et al. |
| 6,482,215 B1 | 11/2002 | Shiber |
| 6,482,216 B1 | 11/2002 | Hiblar et al. |
| 6,488,654 B2 | 12/2002 | Gonzalez et al. |
| 6,491,660 B2 | 12/2002 | Guo et al. |
| 6,494,890 B1 | 12/2002 | Shturman et al. |
| 6,497,711 B1 | 12/2002 | Plaia et al. |
| 6,500,186 B2 | 12/2002 | Lafontaine et al. |
| 6,503,227 B1 | 1/2003 | Guo et al. |
| 6,503,261 B1 | 1/2003 | Bruneau et al. |
| 6,517,544 B1 | 2/2003 | Michelson |
| 6,537,202 B1 | 3/2003 | Frantzen |
| 6,537,279 B1 | 3/2003 | Michelson |
| 6,540,719 B2 | 4/2003 | Bigus et al. |
| 6,554,846 B2 | 4/2003 | Hamilton et al. |
| 6,562,049 B1 | 5/2003 | Norlander et al. |
| 6,569,177 B1 | 5/2003 | Dillard et al. |
| 6,572,630 B1 | 6/2003 | McGuckin, Jr. et al. |
| 6,579,298 B1 | 6/2003 | Bruneau et al. |
| 6,579,299 B2 | 6/2003 | McGuckin, Jr. et al. |
| 6,589,251 B2 | 7/2003 | Yee |
| 6,596,005 B1 | 7/2003 | Kanz |
| 6,602,265 B2 | 8/2003 | Dubrul et al. |
| 6,613,066 B1 | 9/2003 | Fukaya et al. |
| 6,613,075 B1 | 9/2003 | Healy |
| 6,616,676 B2 | 9/2003 | Bashiri |
| 6,620,179 B2 | 9/2003 | Book et al. |
| 6,626,861 B1 | 9/2003 | Hart et al. |
| 6,626,923 B1 | 9/2003 | Wyzgala |
| 6,632,230 B2 | 10/2003 | Barry |
| 6,638,228 B1 | 10/2003 | Chandrasekaran et al. |
| 6,638,288 B1 | 10/2003 | Shturman et al. |
| 6,652,548 B2 | 11/2003 | Evans et al. |
| 6,669,710 B2 | 12/2003 | Moutafis et al. |
| 6,682,543 B2 | 1/2004 | Barbut et al. |
| 6,685,718 B1 | 2/2004 | Wyzgala et al. |
| 6,702,834 B1 | 3/2004 | Boylan |
| 6,719,775 B2 | 4/2004 | Slaker et al. |
| 6,719,781 B1 | 4/2004 | Kim |
| 6,723,390 B2 | 4/2004 | Merdan et al. |
| 6,761,733 B2 | 7/2004 | Chobotov et al. |
| 6,764,498 B2 | 7/2004 | Mische |
| 6,786,876 B2 | 9/2004 | Cox |
| 6,790,215 B2 | 9/2004 | Findlay |
| 6,792,979 B2 | 9/2004 | Konya et al. |
| 6,800,083 B2 | 10/2004 | Hiblar et al. |
| 6,800,085 B2 | 10/2004 | Selmon et al. |
| 6,800,086 B2 | 10/2004 | Strong |
| 6,808,531 B2 | 10/2004 | Lafontaine et al. |
| 6,827,734 B2 | 12/2004 | Fariabi |
| 6,837,890 B1 | 1/2005 | Chludzinski et al. |
| 6,852,097 B1 | 2/2005 | Fulton |
| 6,852,118 B2 | 2/2005 | Shturman et al. |
| 6,872,204 B2 | 3/2005 | Houser et al. |
| 6,884,235 B2 | 4/2005 | McGuckin, Jr. et al. |
| 6,899,712 B2 | 5/2005 | Moutafis et al. |
| 6,911,026 B1 | 6/2005 | Hall et al. |
| 6,939,352 B2 | 9/2005 | Buzzard et al. |
| 6,951,554 B2 | 10/2005 | Johansen et al. |
| 6,951,570 B2 | 10/2005 | Linder et al. |
| 6,953,468 B2 | 10/2005 | Jones et al. |
| 6,986,778 B2 | 1/2006 | Zadno et al. |
| 7,004,173 B2 | 2/2006 | Sparkes et al. |
| 7,027,460 B2 | 4/2006 | Iyer et al. |
| 7,063,714 B2 | 6/2006 | Dorros et al. |
| 7,141,045 B2 | 11/2006 | Johansson et al. |
| 7,169,118 B2 | 1/2007 | Reynolds et al. |
| 7,172,571 B2 | 2/2007 | Moskowitz et al. |
| 7,179,269 B2 | 2/2007 | Welch et al. |
| 7,189,240 B1 | 3/2007 | Dekel |
| 7,211,041 B2 | 5/2007 | Mueller |
| 7,217,255 B2 | 5/2007 | Boyle et al. |
| 7,247,269 B2 | 7/2007 | Keidar |
| 7,252,674 B2 | 8/2007 | Wyzgala et al. |
| 7,311,719 B2 | 12/2007 | Bonutti |
| 7,344,546 B2 | 3/2008 | Wulfman et al. |
| 7,381,216 B2 | 6/2008 | Buzzard et al. |
| 7,384,407 B2 | 6/2008 | Rodriguez et al. |
| 7,485,127 B2 | 2/2009 | Nistal |
| 7,494,485 B2 | 2/2009 | Beck et al. |
| 7,507,245 B2 | 3/2009 | Shturman et al. |
| 7,513,886 B2 | 4/2009 | Konstantino |
| 7,517,352 B2 | 4/2009 | Evans et al. |
| 7,534,249 B2 | 5/2009 | Nash et al. |
| 7,537,588 B2 | 5/2009 | Palasis et al. |
| 7,582,112 B2 | 9/2009 | Scheuemann et al. |
| 7,585,300 B2 | 9/2009 | Cha |
| 7,591,996 B2 | 9/2009 | Hwang et al. |
| 7,594,900 B1 | 9/2009 | Nash et al. |
| 7,618,434 B2 | 11/2009 | Santra et al. |
| D607,102 S | 12/2009 | Robinson |
| 7,632,301 B2 | 12/2009 | Alt |
| 7,645,290 B2 | 1/2010 | Lucas |
| D610,258 S | 2/2010 | Robinson |
| 7,670,327 B2 | 3/2010 | Kucharczyk et al. |
| 7,674,272 B2 | 3/2010 | Torrance et al. |
| 7,686,824 B2 | 3/2010 | Konstantino et al. |
| 7,687,144 B2 | 3/2010 | Clark et al. |
| 7,691,121 B2 | 4/2010 | Rosenbluth et al. |
| 7,697,996 B2 | 4/2010 | Manning et al. |
| 7,699,865 B2 | 4/2010 | Johnson et al. |
| 7,715,896 B2 | 5/2010 | Ramzipoor et al. |
| 7,731,731 B2 | 6/2010 | Abela |

(56) References Cited

U.S. PATENT DOCUMENTS

| | | | |
|---|---|---|---|
| 7,734,332 B2 | 6/2010 | Sher |
| 7,744,587 B2 | 6/2010 | Murphy |
| 7,749,266 B2 | 7/2010 | Forster et al. |
| 7,758,604 B2 | 7/2010 | Wu et al. |
| 7,789,860 B2 | 9/2010 | Brady et al. |
| 7,819,863 B2 | 10/2010 | Eggers et al. |
| 7,832,406 B2 | 11/2010 | Ellis et al. |
| 7,833,240 B2 | 11/2010 | Okushi et al. |
| 7,854,755 B2 | 12/2010 | Lafontaine et al. |
| 7,887,557 B2 | 2/2011 | Kelley et al. |
| 7,909,873 B2 | 3/2011 | Tan-Malecki et al. |
| 7,922,650 B2 | 4/2011 | Mcweeney et al. |
| 7,938,851 B2 | 5/2011 | Olson et al. |
| 7,951,161 B2 | 5/2011 | Bonnette et al. |
| 7,963,915 B2 | 6/2011 | Bleich |
| 7,967,790 B2 | 6/2011 | Whiting et al. |
| 7,967,834 B2 | 6/2011 | Tai et al. |
| 7,976,460 B2 | 7/2011 | Richardson |
| 7,985,200 B2 | 7/2011 | Lary et al. |
| 7,993,384 B2 | 8/2011 | Wu et al. |
| 7,997,226 B2 | 8/2011 | Diaz et al. |
| 8,002,725 B2 | 8/2011 | Hogendijk |
| 8,011,316 B2 | 9/2011 | Diaz et al. |
| 8,012,153 B2 | 9/2011 | Woloszko et al. |
| 8,021,379 B2 | 9/2011 | Thompson et al. |
| 8,043,287 B2 | 10/2011 | Conquergood et al. |
| 8,043,362 B2 | 10/2011 | Gong et al. |
| 8,052,637 B2 | 11/2011 | Von Oepen et al. |
| 8,052,716 B2 | 11/2011 | Gilson et al. |
| 8,062,298 B2 | 11/2011 | Schmitz et al. |
| 8,067,055 B2 | 11/2011 | Savage et al. |
| 8,080,026 B2 | 12/2011 | Konstantino et al. |
| 8,083,713 B2 | 12/2011 | Smith et al. |
| 8,105,351 B2 | 1/2012 | Lehman et al. |
| 8,109,954 B2 | 2/2012 | Shturman |
| 8,109,955 B2 | 2/2012 | Shtruman |
| 8,123,750 B2 | 2/2012 | Norton et al. |
| 8,123,776 B2 | 2/2012 | Gilson et al. |
| 8,134,041 B2 | 3/2012 | Etchells |
| 8,137,369 B2 | 3/2012 | Shturman |
| 8,142,457 B2 | 3/2012 | Lafontaine |
| 8,147,507 B2 | 4/2012 | Shtruman |
| 8,157,825 B2 | 4/2012 | Shtruman |
| 8,158,670 B2 | 4/2012 | Kunz et al. |
| 8,162,964 B2 | 4/2012 | Piippo et al. |
| 8,175,677 B2 | 5/2012 | Sayler et al. |
| 8,177,801 B2 | 5/2012 | Kallock et al. |
| 8,182,499 B2 | 5/2012 | Abraham et al. |
| 8,192,402 B2 | 6/2012 | Anderson et al. |
| 8,192,451 B2 | 6/2012 | Cambronne et al. |
| 8,208,990 B2 | 6/2012 | Maschke |
| 8,221,348 B2 | 7/2012 | Hackett et al. |
| 8,241,335 B2 | 8/2012 | Truckai et al. |
| 8,282,246 B2 | 10/2012 | Quadri et al. |
| 8,308,711 B2 | 11/2012 | Lee et al. |
| 8,308,790 B2 | 11/2012 | Arbefeuille et al. |
| 8,317,786 B2 | 11/2012 | Dahla et al. |
| 8,323,249 B2 | 12/2012 | Wulfman et al. |
| 8,323,261 B2 | 12/2012 | Kugler et al. |
| 8,323,279 B2 | 12/2012 | Dahla et al. |
| 8,337,518 B2 | 12/2012 | Nance et al. |
| 8,348,965 B2 | 1/2013 | Prudnikov et al. |
| 8,348,987 B2 | 1/2013 | Eaton |
| 8,353,923 B2 | 1/2013 | Shturman |
| 8,353,944 B2 | 1/2013 | Weber et al. |
| 8,377,037 B2 | 2/2013 | Sachdeva et al. |
| 8,382,423 B1 | 2/2013 | Frodis et al. |
| 8,382,739 B2 | 2/2013 | Walak |
| 8,388,582 B2 | 3/2013 | Eubanks et al. |
| 8,388,636 B2 | 3/2013 | Shturman |
| 8,388,637 B2 | 3/2013 | Shturman |
| 8,398,663 B2 | 3/2013 | Paul et al. |
| 8,435,228 B2 | 5/2013 | Wulfman et al. |
| 8,439,937 B2 | 5/2013 | Montague et al. |
| 8,449,566 B2 | 5/2013 | Finitsis |
| 8,454,638 B2 | 6/2013 | Shturman |
| 8,465,510 B2 | 6/2013 | Shturman |
| 8,475,478 B2 | 7/2013 | Robinson |
| 8,475,487 B2 | 7/2013 | Bonnette et al. |
| 8,480,628 B2 | 7/2013 | Hawkins et al. |
| 8,496,678 B2 | 7/2013 | Shturman |
| 8,500,764 B2 | 8/2013 | Shturman |
| 8,500,765 B2 | 8/2013 | Shturman |
| 8,524,132 B2 | 9/2013 | Von Oepen et al. |
| 8,529,614 B2 | 9/2013 | Berez et al. |
| 8,530,783 B2 | 9/2013 | Ow et al. |
| 8,532,746 B2 | 9/2013 | Gelbart et al. |
| 8,551,128 B2 | 10/2013 | Hanson et al. |
| 8,551,130 B2 | 10/2013 | Schoenle et al. |
| 8,562,607 B2 | 10/2013 | Truckai et al. |
| 8,568,432 B2 | 10/2013 | Straub |
| 8,579,926 B2 | 11/2013 | Pinto et al. |
| 8,597,239 B2 | 12/2013 | Gerrans et al. |
| 8,597,313 B2 | 12/2013 | Thatcher et al. |
| 8,603,038 B2 | 12/2013 | Nelson |
| 8,612,022 B1 | 12/2013 | Morero et al. |
| 8,613,721 B2 | 12/2013 | Wulfman |
| 8,617,144 B2 | 12/2013 | Ravikumar |
| 8,628,550 B2 | 1/2014 | Narveson |
| 8,628,551 B2 | 1/2014 | Hanson et al. |
| 8,632,556 B2 | 1/2014 | Jacobs et al. |
| 8,632,557 B2 | 1/2014 | Thatcher et al. |
| 8,657,821 B2 | 2/2014 | Palermo |
| 8,663,195 B2 | 3/2014 | Shturman |
| 8,663,228 B2 | 3/2014 | Schmitz et al. |
| 8,663,260 B2 | 3/2014 | Shturman |
| 8,663,261 B2 | 3/2014 | Shturman |
| 8,679,141 B2 | 3/2014 | Goodin et al. |
| 8,684,952 B2 | 4/2014 | Weitzner et al. |
| 8,696,645 B2 | 4/2014 | Tai et al. |
| 8,702,652 B2 | 4/2014 | Fiorella et al. |
| 8,702,735 B2 | 4/2014 | Rivers |
| 8,709,087 B2 | 4/2014 | Cragg |
| 8,715,227 B2 | 5/2014 | Kontos |
| 8,715,240 B2 | 5/2014 | Cunningham |
| 8,728,106 B2 | 5/2014 | Weber et al. |
| 8,758,325 B2 | 6/2014 | Webster et al. |
| 8,758,377 B2 | 6/2014 | Rivers et al. |
| 8,771,302 B2 | 7/2014 | Woolfson et al. |
| 8,779,328 B2 | 7/2014 | Anukhin et al. |
| 8,790,299 B2 | 7/2014 | Gunday et al. |
| 8,792,962 B2 | 7/2014 | Esguerra et al. |
| 8,795,241 B2 | 8/2014 | O'Connell et al. |
| 8,795,303 B2 | 8/2014 | McBroom et al. |
| 8,795,304 B2 | 8/2014 | Svendsen |
| 8,814,892 B2 | 8/2014 | Galdonik et al. |
| 8,827,951 B2 | 9/2014 | Besser et al. |
| 8,840,566 B2 | 9/2014 | Seibel et al. |
| 8,864,762 B2 | 10/2014 | Gunday et al. |
| 8,882,697 B2 | 11/2014 | Celermajer |
| 8,882,790 B2 | 11/2014 | Kassab et al. |
| 8,888,787 B2 | 11/2014 | Wynberg |
| 8,920,402 B2 | 12/2014 | Nash et al. |
| 8,926,560 B2 | 1/2015 | Dinh et al. |
| 8,932,694 B2 | 1/2015 | Rolfes et al. |
| 8,936,589 B2 | 1/2015 | Shturman |
| 8,945,089 B2 | 2/2015 | Johnson et al. |
| 8,951,224 B2 | 2/2015 | Wulfman et al. |
| 8,961,533 B2 | 2/2015 | Stabler et al. |
| 8,968,346 B2 | 3/2015 | Lockard et al. |
| 8,974,519 B2 | 3/2015 | Gennrich et al. |
| 8,986,331 B2 | 3/2015 | Chekan et al. |
| 8,992,553 B2 | 3/2015 | Diamant et al. |
| 8,992,557 B2 | 3/2015 | Whayne et al. |
| 8,992,717 B2 | 3/2015 | Zeroni et al. |
| 8,998,843 B2 | 4/2015 | Bonnette et al. |
| 9,017,294 B2 | 4/2015 | McGuckin, Jr. et al. |
| 9,050,127 B2 | 6/2015 | Bonnette et al. |
| 9,050,414 B2 | 6/2015 | Schoenie et al. |
| 9,055,951 B2 | 6/2015 | Deshpande |
| 9,055,966 B2 | 6/2015 | Cambronne et al. |
| 9,072,873 B2 | 7/2015 | Lippert et al. |
| 9,078,692 B2 | 7/2015 | Shturman et al. |
| 9,078,779 B2 | 7/2015 | Dorn et al. |

(56) References Cited

U.S. PATENT DOCUMENTS

| | | |
|---|---|---|
| 9,084,620 B2 | 7/2015 | Ludin et al. |
| 9,084,627 B2 | 7/2015 | Weber |
| 9,089,362 B2 | 7/2015 | Shturman |
| 9,101,382 B2 | 8/2015 | Krolik et al. |
| 9,101,387 B2 | 8/2015 | Plowe et al. |
| 9,101,430 B2 | 8/2015 | Muller |
| 9,108,027 B2 | 8/2015 | Eubanks et al. |
| 9,114,235 B2 | 8/2015 | Cambronne |
| 9,119,662 B2 | 9/2015 | Moberg |
| 9,119,944 B2 | 9/2015 | Chambers et al. |
| 9,138,210 B2 | 9/2015 | Schulte et al. |
| 9,162,040 B2 | 10/2015 | Vo et al. |
| 9,162,046 B2 | 10/2015 | Hill et al. |
| 9,174,019 B2 | 11/2015 | Gregersen |
| 9,180,274 B2 | 11/2015 | Cully et al. |
| 9,186,129 B2 | 11/2015 | Blitzer et al. |
| 9,186,170 B2 | 11/2015 | Welty et al. |
| 9,186,210 B2 | 11/2015 | Jenson |
| 9,192,405 B2 | 11/2015 | Shturman |
| 9,199,058 B2 | 12/2015 | Lentz |
| 9,205,234 B2 | 12/2015 | Hardin |
| 9,211,138 B2 | 12/2015 | Shturman |
| 9,211,386 B2 | 12/2015 | Aboytes |
| 9,216,033 B2 | 12/2015 | Feld et al. |
| 9,216,034 B2 | 12/2015 | Avneri |
| 9,217,442 B2 | 12/2015 | Wiessler et al. |
| 9,220,529 B2 | 12/2015 | Rivers et al. |
| 9,220,530 B2 | 12/2015 | Moberg |
| 9,226,763 B2 | 1/2016 | To et al. |
| 9,237,903 B2 | 1/2016 | Shturman |
| 9,238,126 B2 | 1/2016 | Gerrans et al. |
| 9,254,143 B2 | 2/2016 | Huynh et al. |
| 9,259,215 B2 | 2/2016 | Chou et al. |
| 9,265,563 B2 | 2/2016 | Racz et al. |
| 9,289,230 B2 | 3/2016 | Cambronne |
| 9,295,373 B2 | 3/2016 | Torrance et al. |
| 9,301,769 B2 | 4/2016 | Brady et al. |
| 9,301,774 B2 | 4/2016 | O'Day |
| 9,308,007 B2 | 4/2016 | Cully et al. |
| 9,308,019 B2 | 4/2016 | Kugler et al. |
| 9,314,324 B2 | 4/2016 | Janardhan et al. |
| 9,320,530 B2 | 4/2016 | Grace |
| 9,320,535 B2 | 4/2016 | Zaretzka et al. |
| 9,320,540 B2 | 4/2016 | Badie |
| 9,326,789 B2 | 5/2016 | Fruland et al. |
| 9,333,006 B2 | 5/2016 | Shturman |
| 9,333,335 B2 | 5/2016 | Ollivier et al. |
| 9,345,508 B2 | 5/2016 | Hendrick |
| 9,345,511 B2 | 5/2016 | Smith et al. |
| 9,345,858 B2 | 5/2016 | Flaherty et al. |
| 9,351,741 B2 | 5/2016 | Schmitz et al. |
| 9,351,757 B2 | 5/2016 | Kusleika |
| 9,364,255 B2 | 6/2016 | Weber |
| 9,364,256 B2 | 6/2016 | Shturman |
| 9,370,649 B2 | 6/2016 | Chang et al. |
| 9,375,234 B2 | 6/2016 | Vrba |
| 9,375,328 B2 | 6/2016 | Farnan |
| 9,381,062 B2 | 7/2016 | Kapur et al. |
| 9,387,006 B2 | 7/2016 | Shtruman |
| 9,387,305 B2 | 7/2016 | Courtney et al. |
| 9,398,837 B2 | 7/2016 | Vazales et al. |
| 9,402,981 B2 | 8/2016 | Anderson |
| 9,413,896 B2 | 8/2016 | Bowe et al. |
| 9,414,852 B2 | 8/2016 | Gifford, III et al. |
| 9,427,553 B2 | 8/2016 | Nelson |
| D766,433 S | 9/2016 | Blackledge et al. |
| 9,433,437 B2 | 9/2016 | Kesten et al. |
| 9,439,674 B2 | 9/2016 | Rydberg et al. |
| 9,445,829 B2 | 9/2016 | Brady et al. |
| 9,452,241 B2 | 9/2016 | Gill et al. |
| 9,456,843 B2 | 10/2016 | Kessler et al. |
| 9,463,041 B2 | 10/2016 | Bleich et al. |
| 9,468,457 B2 | 10/2016 | Blackledge et al. |
| 9,474,536 B2 | 10/2016 | Carrison et al. |
| 9,474,543 B2 | 10/2016 | McGuckin, Jr. et al. |
| 9,486,611 B2 | 11/2016 | Petersen et al. |
| 9,498,183 B2 | 11/2016 | Brown et al. |
| 9,498,290 B2 | 11/2016 | Piferi et al. |
| 9,510,885 B2 | 12/2016 | Burger et al. |
| 9,526,519 B2 | 12/2016 | Kessler et al. |
| 9,526,674 B2 | 12/2016 | Heyns et al. |
| 9,532,797 B2 | 1/2017 | Vreeman |
| 9,532,799 B2 | 1/2017 | Simpson et al. |
| 9,539,019 B2 | 1/2017 | Sullivan et al. |
| 9,545,298 B2 | 1/2017 | Ginn et al. |
| 9,561,347 B2 | 2/2017 | Holm et al. |
| 9,572,492 B2 | 2/2017 | Simpson et al. |
| 9,597,109 B2 | 3/2017 | Shturman |
| 9,597,110 B2 | 3/2017 | Kessler et al. |
| 9,675,376 B2 | 6/2017 | To et al. |
| 9,687,266 B2 | 6/2017 | Moberg et al. |
| 9,693,796 B2 | 7/2017 | Rydberg |
| 9,700,346 B2 | 7/2017 | Levine et al. |
| 9,700,347 B2 | 7/2017 | Shiber |
| 9,717,520 B2 | 8/2017 | Zeroni et al. |
| 9,750,509 B2 | 9/2017 | Carrison |
| 9,855,072 B2 | 1/2018 | Moberg |
| 9,901,252 B2 | 2/2018 | Tran |
| 10,786,278 B2 | 9/2020 | Nishio et al. |
| 10,869,689 B2 | 12/2020 | Flemming et al. |
| 10,925,632 B2 | 2/2021 | Jamous et al. |
| 10,987,126 B2 | 4/2021 | Jamous et al. |
| 11,051,842 B2 | 7/2021 | Jamous et al. |
| 2001/0018591 A1 | 8/2001 | Brock et al. |
| 2001/0047165 A1 | 11/2001 | Makower et al. |
| 2002/0007190 A1* | 1/2002 | Wulfman ....... A61B 17/320758 606/171 |
| 2002/0029057 A1 | 3/2002 | McGuckin, Jr. |
| 2002/0098278 A1 | 7/2002 | Bates et al. |
| 2002/0151917 A1 | 10/2002 | Barry |
| 2003/0069522 A1 | 4/2003 | Jacobsen et al. |
| 2003/0109837 A1 | 6/2003 | McBride |
| 2003/0139689 A1 | 7/2003 | Shturman et al. |
| 2003/0144656 A1 | 7/2003 | Ocel et al. |
| 2003/0187498 A1 | 10/2003 | Bishop |
| 2003/0191435 A1 | 10/2003 | Shkolnik |
| 2003/0199889 A1 | 10/2003 | Kanz et al. |
| 2003/0236533 A1 | 12/2003 | Wilson et al. |
| 2004/0097995 A1 | 5/2004 | Nash et al. |
| 2004/0147934 A1 | 7/2004 | Kiester |
| 2004/0215222 A1 | 10/2004 | Krivoruchko |
| 2004/0225355 A1 | 11/2004 | Stevens |
| 2004/0267191 A1 | 12/2004 | Gifford et al. |
| 2005/0031495 A1 | 2/2005 | Choi et al. |
| 2005/0096633 A1 | 5/2005 | Moskowitz |
| 2005/0149083 A1 | 7/2005 | Prudnikov et al. |
| 2005/0149084 A1 | 7/2005 | Kanz et al. |
| 2005/0187537 A1 | 8/2005 | Loeb et al. |
| 2005/0187556 A1 | 8/2005 | Stack et al. |
| 2005/0203553 A1 | 9/2005 | Maschke |
| 2005/0216044 A1 | 9/2005 | Hong |
| 2005/0228417 A1 | 10/2005 | Teitelbaum et al. |
| 2005/0251187 A1 | 11/2005 | Beane et al. |
| 2005/0272976 A1 | 12/2005 | Tanaka et al. |
| 2006/0030934 A1 | 2/2006 | Hogendijk et al. |
| 2006/0047291 A1 | 3/2006 | Barry |
| 2006/0095059 A1 | 5/2006 | Bleich et al. |
| 2006/0142630 A1 | 6/2006 | Meretei |
| 2006/0142632 A1 | 6/2006 | Meretei |
| 2006/0264988 A1 | 11/2006 | Boyle |
| 2006/0271155 A1 | 11/2006 | Herr |
| 2007/0088230 A1 | 4/2007 | Terashi et al. |
| 2007/0093779 A1 | 4/2007 | Kugler et al. |
| 2007/0093781 A1 | 4/2007 | Kugler et al. |
| 2007/0135830 A1 | 6/2007 | Schaeffer |
| 2007/0203516 A1 | 8/2007 | Nayak |
| 2007/0213753 A1 | 9/2007 | Waller |
| 2007/0282367 A1 | 12/2007 | Jeffrey et al. |
| 2007/0287933 A1 | 12/2007 | Phan et al. |
| 2008/0033423 A1 | 2/2008 | Peacock |
| 2008/0033467 A1 | 2/2008 | Miyamoto et al. |
| 2008/0161840 A1 | 7/2008 | Osiroff et al. |
| 2008/0208230 A1 | 8/2008 | Chin |
| 2008/0221566 A1 | 9/2008 | Krishnan |

(56) References Cited

U.S. PATENT DOCUMENTS

| | | |
|---|---|---|
| 2008/0228208 A1 | 9/2008 | Wulfman et al. |
| 2008/0306498 A1 | 12/2008 | Thatcher et al. |
| 2008/0312671 A1* | 12/2008 | Riles ............... A61B 17/32037 606/159 |
| 2009/0018564 A1 | 1/2009 | Shturman |
| 2009/0069829 A1 | 3/2009 | Shturman |
| 2009/0112239 A1 | 4/2009 | To |
| 2009/0149865 A1 | 6/2009 | Schmitz et al. |
| 2009/0163940 A1 | 6/2009 | Sliwa |
| 2009/0182359 A1 | 7/2009 | Shturman |
| 2009/0182362 A1 | 7/2009 | Thompson et al. |
| 2009/0216284 A1 | 8/2009 | Chin et al. |
| 2009/0264907 A1 | 10/2009 | Vrba et al. |
| 2009/0306689 A1 | 12/2009 | Welty et al. |
| 2009/0306690 A1 | 12/2009 | Rivers et al. |
| 2009/0318942 A1 | 12/2009 | Shturman |
| 2009/0326568 A1 | 12/2009 | Shturman |
| 2010/0010522 A1 | 1/2010 | Shturman |
| 2010/0030251 A1 | 2/2010 | Sandhu et al. |
| 2010/0063534 A1 | 3/2010 | Kugler et al. |
| 2010/0082051 A1 | 4/2010 | Thorpe et al. |
| 2010/0121361 A1 | 5/2010 | Plowe et al. |
| 2010/0211088 A1 | 8/2010 | Narveson |
| 2010/0228152 A1 | 9/2010 | Fisher |
| 2010/0234864 A1 | 9/2010 | Keller |
| 2010/0241148 A1 | 9/2010 | Schon et al. |
| 2010/0280534 A1 | 11/2010 | Sher |
| 2010/0292720 A1 | 11/2010 | Thatcher et al. |
| 2011/0046543 A1 | 2/2011 | Brandeis |
| 2011/0077673 A1 | 3/2011 | Grubac et al. |
| 2011/0082483 A1 | 4/2011 | Diamant et al. |
| 2011/0087254 A1 | 4/2011 | Welty |
| 2011/0172598 A1 | 7/2011 | Sampognaro et al. |
| 2011/0184447 A1 | 7/2011 | Leibowitz |
| 2011/0213391 A1 | 9/2011 | Rivers et al. |
| 2011/0224625 A1 | 9/2011 | Flickinger et al. |
| 2011/0282354 A1 | 11/2011 | Schulte |
| 2011/0282368 A1 | 11/2011 | Swayze et al. |
| 2011/0301626 A1 | 12/2011 | To |
| 2011/0306995 A1 | 12/2011 | Moberg |
| 2012/0035633 A1 | 2/2012 | Shturman |
| 2012/0035705 A1 | 2/2012 | Giasolli |
| 2012/0046599 A1 | 2/2012 | Schoenle et al. |
| 2012/0046600 A1 | 2/2012 | Kohler et al. |
| 2012/0065639 A1 | 3/2012 | Schmitz |
| 2012/0109170 A1 | 5/2012 | Shturman |
| 2012/0109171 A1 | 5/2012 | Zeroni |
| 2012/0158120 A1 | 6/2012 | Hacker |
| 2012/0165846 A1 | 6/2012 | Shturman |
| 2012/0165847 A1 | 6/2012 | Shturman |
| 2012/0172901 A1 | 7/2012 | Manderfeld et al. |
| 2012/0172903 A1 | 7/2012 | Shturman |
| 2012/0209176 A1 | 8/2012 | Anderson |
| 2012/0232570 A1 | 9/2012 | Jenson et al. |
| 2012/0253372 A1 | 10/2012 | Ross et al. |
| 2012/0259354 A1 | 10/2012 | Kellett |
| 2012/0265229 A1 | 10/2012 | Rottenberg et al. |
| 2013/0005218 A1 | 1/2013 | von Oepen et al. |
| 2013/0010397 A1 | 1/2013 | Ohara et al. |
| 2013/0018398 A1 | 1/2013 | Rivers et al. |
| 2013/0018399 A1 | 1/2013 | Rivers et al. |
| 2013/0023913 A1 | 1/2013 | Rivers et al. |
| 2013/0060234 A1 | 3/2013 | Besser et al. |
| 2013/0072936 A1 | 3/2013 | To et al. |
| 2013/0085514 A1 | 4/2013 | Lee et al. |
| 2013/0092298 A1 | 4/2013 | Bregulla et al. |
| 2013/0103067 A1 | 4/2013 | Fabo et al. |
| 2013/0116655 A1 | 5/2013 | Bacino et al. |
| 2013/0123661 A1 | 5/2013 | Dewaele et al. |
| 2013/0158578 A1 | 6/2013 | Ghodke et al. |
| 2013/0253467 A1 | 9/2013 | Gianotti et al. |
| 2013/0267870 A1 | 10/2013 | Lonky |
| 2013/0296904 A1 | 11/2013 | Shturman |
| 2013/0296905 A1 | 11/2013 | Shturman |
| 2013/0310859 A1 | 11/2013 | Shturman |
| 2013/0317529 A1 | 11/2013 | Golden et al. |
| 2014/0024945 A1 | 1/2014 | Mung et al. |
| 2014/0025044 A1 | 1/2014 | Zamarripa et al. |
| 2014/0039494 A1 | 2/2014 | Kick et al. |
| 2014/0074097 A1 | 3/2014 | Schmitz |
| 2014/0081298 A1 | 3/2014 | Cambronne |
| 2014/0094833 A1 | 4/2014 | Malhi |
| 2014/0100585 A1 | 4/2014 | Anderson et al. |
| 2014/0128893 A1 | 5/2014 | Guggenheimer et al. |
| 2014/0128963 A1 | 5/2014 | Quill et al. |
| 2014/0155990 A1 | 6/2014 | Nyuli et al. |
| 2014/0163664 A1 | 6/2014 | Goldsmith |
| 2014/0180317 A1 | 6/2014 | Shturman |
| 2014/0180319 A1 | 6/2014 | Shturman |
| 2014/0213893 A1 | 7/2014 | Simpson et al. |
| 2014/0214060 A1 | 7/2014 | Bonnette et al. |
| 2014/0222042 A1 | 8/2014 | Kessler et al. |
| 2014/0222045 A1 | 8/2014 | Schneider et al. |
| 2014/0275770 A1 | 9/2014 | Gunday et al. |
| 2014/0276390 A1 | 9/2014 | Eubanks et al. |
| 2014/0276407 A1 | 9/2014 | DeVries et al. |
| 2014/0276684 A1 | 9/2014 | Huennekens et al. |
| 2014/0276696 A1 | 9/2014 | Schneider |
| 2014/0276920 A1 | 9/2014 | Hendrick et al. |
| 2014/0277002 A1 | 9/2014 | Grace |
| 2014/0277011 A1 | 9/2014 | Meader |
| 2014/0296706 A1 | 10/2014 | Chronos et al. |
| 2014/0296742 A1 | 10/2014 | Kalloo et al. |
| 2014/0296868 A1 | 10/2014 | Garrison |
| 2014/0296897 A1 | 10/2014 | Sotak et al. |
| 2014/0303658 A1 | 10/2014 | Bonnette et al. |
| 2014/0316448 A1 | 10/2014 | Higgins |
| 2014/0316449 A1 | 10/2014 | Grothe et al. |
| 2014/0330284 A1 | 11/2014 | Sawada |
| 2014/0330286 A1 | 11/2014 | Wallace |
| 2014/0330366 A1 | 11/2014 | Dehdeshtian |
| 2014/0343538 A1 | 11/2014 | Lenker et al. |
| 2014/0350582 A1 | 11/2014 | Higgins |
| 2014/0358123 A1 | 12/2014 | Ueda et al. |
| 2014/0358156 A1 | 12/2014 | Argentine |
| 2014/0371770 A1 | 12/2014 | Schoenle et al. |
| 2015/0005791 A1 | 1/2015 | Schoenle et al. |
| 2015/0018711 A1 | 1/2015 | Furlong et al. |
| 2015/0032141 A1 | 1/2015 | Silvestro |
| 2015/0032142 A1 | 1/2015 | Silvestro |
| 2015/0038902 A1 | 2/2015 | Mark et al. |
| 2015/0051625 A1 | 2/2015 | Petrucci et al. |
| 2015/0068069 A1 | 3/2015 | Fran et al. |
| 2015/0080795 A1 | 3/2015 | Mattison et al. |
| 2015/0080928 A1 | 3/2015 | Kugler et al. |
| 2015/0088246 A1 | 3/2015 | Astarci et al. |
| 2015/0119909 A1 | 4/2015 | Rydberg |
| 2015/0127035 A1 | 5/2015 | Frappetai. |
| 2015/0133978 A1 | 5/2015 | Paul, Jr. |
| 2015/0142028 A1 | 5/2015 | Ellering et al. |
| 2015/0150587 A1 | 6/2015 | Smith et al. |
| 2015/0150588 A1 | 6/2015 | Rydberg |
| 2015/0157303 A1 | 6/2015 | Brandeis |
| 2015/0164541 A1 | 6/2015 | Shiber |
| 2015/0190622 A1 | 7/2015 | Saab |
| 2015/0201956 A1 | 7/2015 | Higgins et al. |
| 2015/0202044 A1 | 7/2015 | Chau et al. |
| 2015/0209066 A1 | 7/2015 | Dahm et al. |
| 2015/0209072 A1 | 7/2015 | Higgins et al. |
| 2015/0223948 A1 | 8/2015 | Lopez |
| 2015/0224281 A1 | 8/2015 | Kim et al. |
| 2015/0230810 A1 | 8/2015 | Creighton et al. |
| 2015/0230821 A1 | 8/2015 | Batchelor et al. |
| 2015/0238207 A1 | 8/2015 | Cox et al. |
| 2015/0245851 A1 | 9/2015 | McGuckin, Jr. |
| 2015/0258258 A1 | 9/2015 | Bonnette et al. |
| 2015/0265813 A1 | 9/2015 | Xie et al. |
| 2015/0273184 A1 | 10/2015 | Scott et al. |
| 2015/0289902 A1 | 10/2015 | Hehrlein |
| 2015/0290438 A1 | 10/2015 | Gerrans et al. |
| 2015/0313629 A1 | 11/2015 | Shturman |
| 2015/0320971 A1 | 11/2015 | Leeflang et al. |
| 2015/0327884 A1 | 11/2015 | Moberg |
| 2015/0335348 A1 | 11/2015 | Cohen et al. |

(56) References Cited

U.S. PATENT DOCUMENTS

| | | |
|---|---|---|
| 2015/0342682 A1 | 12/2015 | Bowe |
| 2015/0342718 A1 | 12/2015 | Weber et al. |
| 2015/0351729 A1 | 12/2015 | Chin et al. |
| 2015/0352330 A1 | 12/2015 | Wasdyke et al. |
| 2015/0359595 A1 | 12/2015 | Ben et al. |
| 2015/0374908 A1 | 12/2015 | Piferi |
| 2016/0001062 A1 | 1/2016 | Weber et al. |
| 2016/0015420 A1 | 1/2016 | Higgins et al. |
| 2016/0015434 A1 | 1/2016 | Stieglitz et al. |
| 2016/0022244 A1 | 1/2016 | Courtney et al. |
| 2016/0022296 A1 | 1/2016 | Brady et al. |
| 2016/0022307 A1 | 1/2016 | Wasdyke et al. |
| 2016/0051323 A1 | 2/2016 | Stigall et al. |
| 2016/0058467 A1 | 3/2016 | Shturman |
| 2016/0058468 A1 | 3/2016 | Shturman |
| 2016/0066803 A1 | 3/2016 | Hu et al. |
| 2016/0067465 A1 | 3/2016 | Gerrans et al. |
| 2016/0095733 A1 | 4/2016 | Sharma et al. |
| 2016/0120565 A1 | 5/2016 | Kobayashi et al. |
| 2016/0120570 A1 | 5/2016 | Kobayashi et al. |
| 2016/0128718 A1 | 5/2016 | Aggerholm et al. |
| 2016/0128857 A1 | 5/2016 | Kao |
| 2016/0135796 A1 | 5/2016 | Hundertmark et al. |
| 2016/0136393 A1 | 5/2016 | Tsai et al. |
| 2016/0151639 A1 | 6/2016 | Scharf et al. |
| 2016/0157872 A1 | 6/2016 | Cage et al. |
| 2016/0157886 A1 | 6/2016 | WasDyke et al. |
| 2016/0158490 A1 | 6/2016 | Leeflang et al. |
| 2016/0166265 A1 | 6/2016 | Nita |
| 2016/0174964 A1 | 6/2016 | Tobis |
| 2016/0183963 A1 | 6/2016 | Richter et al. |
| 2016/0183966 A1 | 6/2016 | McGuckin, Jr. et al. |
| 2016/0183968 A1 | 6/2016 | Cambronne |
| 2016/0199091 A1 | 7/2016 | Pigott |
| 2016/0199093 A1 | 7/2016 | Cambronne |
| 2016/0206340 A1 | 7/2016 | Vetter et al. |
| 2016/0213397 A1 | 7/2016 | Shturman |
| 2016/0220399 A1 | 8/2016 | Longo |
| 2016/0228681 A1 | 8/2016 | di Palma et al. |
| 2016/0242790 A1 | 8/2016 | Brandeis |
| 2016/0242805 A1 | 8/2016 | Kohler et al. |
| 2016/0242809 A1 | 8/2016 | Shturman |
| 2016/0249942 A1 | 9/2016 | Olson |
| 2016/0256620 A1 | 9/2016 | Scheckel et al. |
| 2016/0263361 A1 | 9/2016 | Vadivelu et al. |
| 2016/0263391 A1 | 9/2016 | Tasci et al. |
| 2016/0270814 A1 | 9/2016 | Palme et al. |
| 2016/0278805 A1 | 9/2016 | Hatta et al. |
| 2016/0287438 A1 | 10/2016 | Badawi et al. |
| 2016/0296683 A1 | 10/2016 | Jin et al. |
| 2016/0302950 A1 | 10/2016 | Marmur et al. |
| 2016/0310709 A1 | 10/2016 | Gotou et al. |
| 2016/0324535 A1 | 11/2016 | Chang et al. |
| 2016/0331394 A1 | 11/2016 | Rottenberg et al. |
| 2016/0338727 A1 | 11/2016 | Bowe et al. |
| 2016/0346003 A1 | 12/2016 | Grothe et al. |
| 2016/0354107 A1 | 12/2016 | Nakano et al. |
| 2016/0354108 A1 | 12/2016 | Nakano et al. |
| 2016/0361528 A1 | 12/2016 | Kanz et al. |
| 2016/0374715 A1 | 12/2016 | McPeak |
| 2016/0375235 A1 | 12/2016 | Schoenle et al. |
| 2017/0000518 A1 | 1/2017 | Smith et al. |
| 2017/0000977 A1 | 1/2017 | Dtorbeck et al. |
| 2017/0027725 A1 | 2/2017 | Argentine |
| 2017/0056169 A1 | 3/2017 | Johnson et al. |
| 2017/0071624 A1 | 3/2017 | McGuckin, Jr. et al. |
| 2017/0079546 A1 | 3/2017 | Costello et al. |
| 2017/0079685 A1 | 3/2017 | Sullivan et al. |
| 2017/0100570 A1 | 4/2017 | Giasolli et al. |
| 2017/0156749 A1 | 6/2017 | Pigott |
| 2017/0164965 A1 | 6/2017 | Chang et al. |
| 2017/0173262 A1 | 6/2017 | Veltz |
| 2017/0273698 A1 | 9/2017 | McGuckin, Jr. et al. |
| 2017/0274270 A1 | 9/2017 | Lundbaek |
| 2017/0348019 A1* | 12/2017 | Nakano ............ A61B 17/320725 |
| 2017/0354435 A1 | 12/2017 | Hatta et al. |
| 2018/0042640 A1 | 2/2018 | Govari et al. |
| 2018/0133436 A1 | 5/2018 | Garrison et al. |
| 2018/0263654 A1 | 9/2018 | Steele et al. |
| 2018/0317952 A1 | 11/2018 | Jamo et al. |
| 2018/0317953 A1 | 11/2018 | Jamo et al. |
| 2018/0317954 A1 | 11/2018 | Jamo et al. |
| 2018/0317955 A1 | 11/2018 | Jamo et al. |
| 2018/0317956 A1 | 11/2018 | Fleming et al. |
| 2019/0038300 A1* | 2/2019 | Savastano ............ A61M 1/842 |
| 2019/0058543 A1 | 2/2019 | Stephenson et al. |
| 2019/0201052 A1 | 7/2019 | Sahadevan et al. |
| 2019/0247084 A1 | 8/2019 | Spangler et al. |
| 2019/0307483 A1 | 10/2019 | Flury et al. |
| 2019/0357936 A1 | 11/2019 | To et al. |
| 2019/0365412 A1 | 12/2019 | WasDyke et al. |
| 2020/0046403 A1 | 2/2020 | Piippo Svendsen et al. |
| 2020/0229844 A1 | 7/2020 | Rawson et al. |

FOREIGN PATENT DOCUMENTS

| | | |
|---|---|---|
| AU | 2011267862 A1 | 12/2012 |
| AU | 2013316091 A1 | 3/2015 |
| CA | 2648870 A1 | 1/2008 |
| CA | 2722317 A1 | 12/2009 |
| CA | 2800920 A1 | 12/2011 |
| CA | 2883961 A | 3/2014 |
| CN | 102056558 A | 5/2011 |
| CN | 102946815 A | 2/2013 |
| CN | 104955406 A | 9/2015 |
| CN | 205866805 U | 1/2017 |
| DE | 29521096 U1 | 8/1996 |
| EP | 446932 A2 | 9/1991 |
| EP | 566426 A1 | 10/1993 |
| EP | 566656 A1 | 10/1993 |
| EP | 689468 A1 | 1/1996 |
| EP | 895458 A2 | 2/1999 |
| EP | 921761 A1 | 6/1999 |
| EP | 1003425 A1 | 5/2000 |
| EP | 1030705 A2 | 8/2000 |
| EP | 1037560 A1 | 9/2000 |
| EP | 1039864 A1 | 10/2000 |
| EP | 1083829 A1 | 3/2001 |
| EP | 1105049 A2 | 6/2001 |
| EP | 1112103 A2 | 7/2001 |
| EP | 1148900 A1 | 10/2001 |
| EP | 1168965 A1 | 1/2002 |
| EP | 1187561 A1 | 3/2002 |
| EP | 1250108 A1 | 10/2002 |
| EP | 1274372 A2 | 1/2003 |
| EP | 1343422 A2 | 9/2003 |
| EP | 1377234 A2 | 1/2004 |
| EP | 1776938 A2 | 2/2004 |
| EP | 1302178 B1 | 3/2006 |
| EP | 1660151 A2 | 5/2006 |
| EP | 1673003 A2 | 6/2006 |
| EP | 1708779 A2 | 10/2006 |
| EP | 1737335 A2 | 1/2007 |
| EP | 1755489 A2 | 2/2007 |
| EP | 1761206 A2 | 3/2007 |
| EP | 187499 A2 | 1/2008 |
| EP | 1874224 A1 | 1/2008 |
| EP | 1897581 A2 | 3/2008 |
| EP | 1906888 A1 | 4/2008 |
| EP | 1983882 A2 | 10/2008 |
| EP | 2010265 A2 | 1/2009 |
| EP | 2024001 A2 | 2/2009 |
| EP | 2040626 A1 | 4/2009 |
| EP | 2040627 A2 | 4/2009 |
| EP | 2040628 A1 | 4/2009 |
| EP | 2079407 A2 | 7/2009 |
| EP | 2099368 A1 | 9/2009 |
| EP | 1864618 B1 | 10/2009 |
| EP | 2155080 A1 | 2/2010 |
| EP | 2008770478 A1 | 2/2010 |
| EP | 2203121 A1 | 7/2010 |
| EP | 2280657 A1 | 2/2011 |
| EP | 2282688 A1 | 2/2011 |
| EP | 2303149 A1 | 4/2011 |

(56) References Cited

FOREIGN PATENT DOCUMENTS

| | | |
|---|---|---|
| EP | 2303151 A1 | 4/2011 |
| EP | 2398405 A1 | 12/2011 |
| EP | 2579791 A1 | 4/2013 |
| EP | 2280656 B1 | 10/2013 |
| EP | 2742881 A1 | 6/2014 |
| EP | 2819586 A2 | 1/2015 |
| EP | 2895088 A2 | 7/2015 |
| EP | 2298220 B1 | 6/2016 |
| EP | 1887945 B1 | 8/2016 |
| EP | 3141201 A1 | 3/2017 |
| EP | 3166512 A1 | 5/2017 |
| EP | 2967635 B1 | 6/2017 |
| EP | 3366239 A1 | 8/2018 |
| ES | 2482608 T3 | 8/2014 |
| ES | 2594707 T3 | 12/2016 |
| GB | 2440220 A | 1/2008 |
| GB | 2440221 A | 1/2008 |
| GB | 2440222 A | 1/2008 |
| JP | 2013532027 A | 8/2013 |
| JP | 2013532028 A | 10/2015 |
| JP | 2015529530 A | 10/2015 |
| NL | 1016653 C2 | 5/2002 |
| RU | 2012150415 A | 7/2014 |
| RU | 2538174 C2 | 1/2015 |
| WO | 94/17739 A1 | 8/1994 |
| WO | 1994028803 A1 | 12/1994 |
| WO | 1997043949 A1 | 11/1997 |
| WO | 1998008554 A1 | 3/1998 |
| WO | 1999018862 A1 | 4/1999 |
| WO | 1999018864 A1 | 4/1999 |
| WO | 1999029420 A1 | 6/1999 |
| WO | 1999035980 A1 | 7/1999 |
| WO | 1999044516 A1 | 9/1999 |
| WO | 1999047053 A1 | 9/1999 |
| WO | 2000056230 A2 | 9/2000 |
| WO | 200195801 A2 | 12/2001 |
| WO | 2002049518 A2 | 6/2002 |
| WO | 2002083226 A2 | 10/2002 |
| WO | 2004073524 A1 | 9/2004 |
| WO | 2005112834 A2 | 12/2005 |
| WO | 2006084256 A1 | 8/2006 |
| WO | 2008006705 A2 | 1/2008 |
| WO | 2008006706 A1 | 1/2008 |
| WO | 2008006708 A1 | 1/2008 |
| WO | 2008062069 A1 | 5/2008 |
| WO | 2008099424 A2 | 8/2008 |
| WO | 2008154480 A1 | 12/2008 |
| WO | 2009146248 A1 | 12/2009 |
| WO | 2009148805 A1 | 12/2009 |
| WO | 2009148807 A1 | 12/2009 |
| WO | 2010002507 A1 | 1/2010 |
| WO | 2010096140 A1 | 8/2010 |
| WO | 2010112617 A | 10/2010 |
| WO | 2010112618 A1 | 10/2010 |
| WO | 2011057060 A2 | 5/2011 |
| WO | 2011143203 A1 | 11/2011 |
| WO | 2011159697 A1 | 12/2011 |
| WO | 2013072777 A2 | 5/2013 |
| WO | 2013123007 A1 | 8/2013 |
| WO | 2014022866 A1 | 2/2014 |
| WO | 2014042752 A2 | 3/2014 |
| WO | 2014080424 A2 | 5/2014 |
| WO | 2014106847 A1 | 7/2014 |
| WO | 2015006309 A1 | 1/2015 |
| WO | 2015013590 A1 | 1/2015 |
| WO | 2015075708 A1 | 5/2015 |
| WO | 2015148284 A1 | 10/2015 |
| WO | 2016007652 A1 | 1/2016 |
| WO | 2016011312 A1 | 1/2016 |
| WO | 2016019991 A1 | 2/2016 |
| WO | 2016044406 A1 | 3/2016 |
| WO | 2016073710 A1 | 5/2016 |
| WO | 2016077758 A1 | 5/2016 |
| WO | 2016108860 A1 | 7/2016 |
| WO | 2016123557 A1 | 8/2016 |
| WO | 2016126974 A1 | 8/2016 |
| WO | 2016133931 A1 | 8/2016 |
| WO | 2016133932 A1 | 8/2016 |
| WO | 2016150806 A1 | 9/2016 |
| WO | 2017035381 A1 | 3/2017 |
| WO | 2017109788 A1 | 6/2017 |

OTHER PUBLICATIONS

Boston Scientific Convex Burrs, Rotablator, Rotational Atherectomy System Reference Guide, Apr. 2014, 22 pages, Natick, MA.

PCT International Search Report and Written Opinion in International Application No. PCT/2020/033023, dated Aug. 31, 2020, 14 pages.

\* cited by examiner

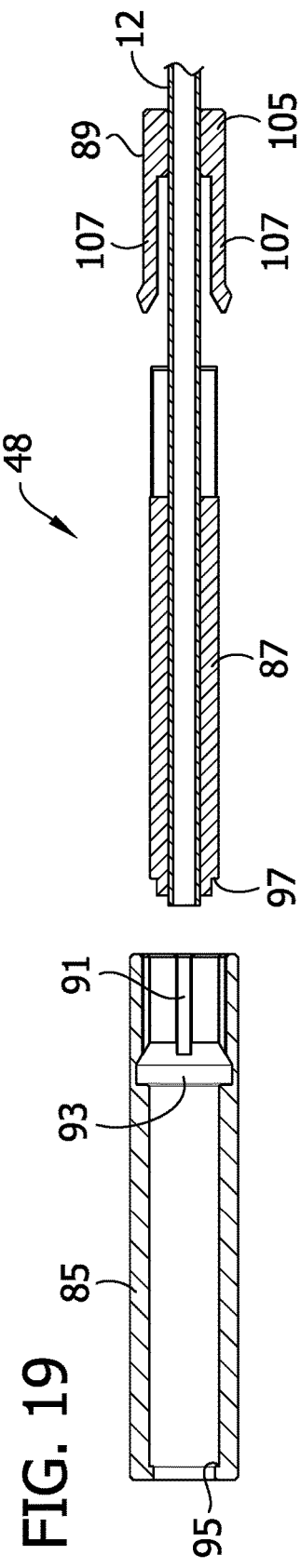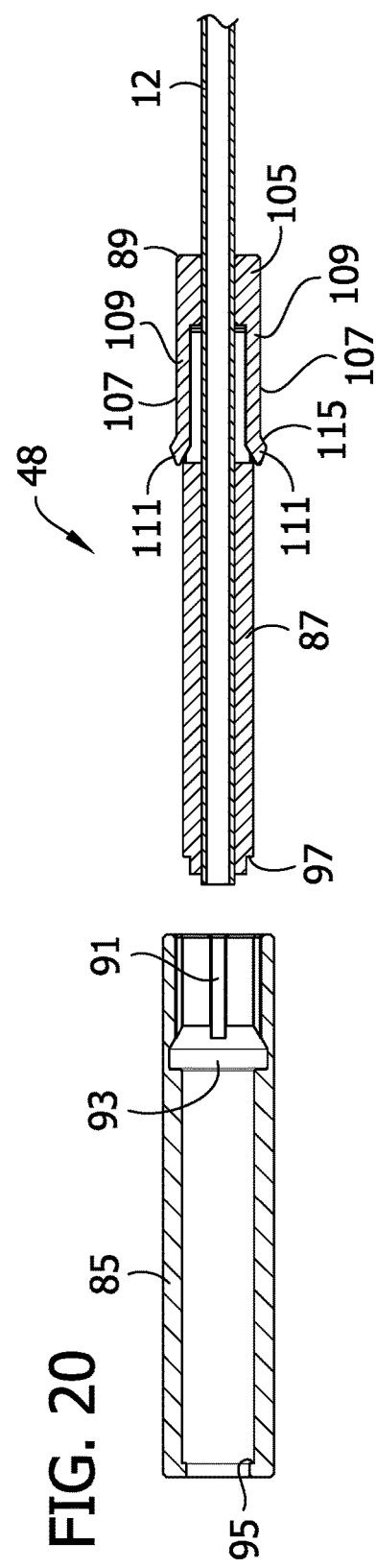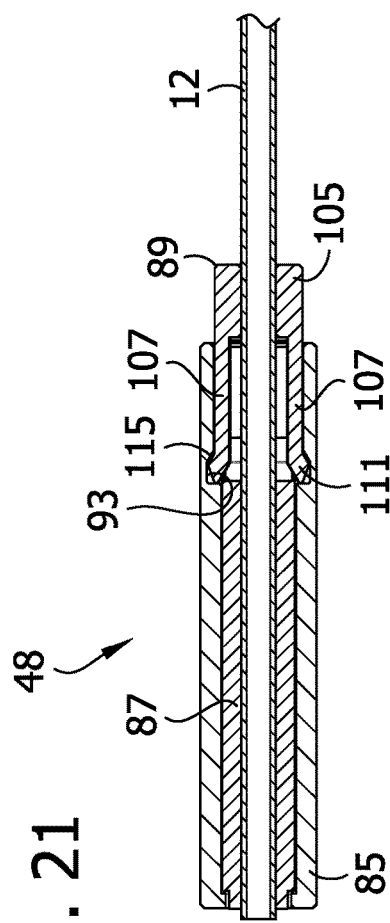
FIG. 19
FIG. 20
FIG. 21

TISSUE-REMOVING CATHETER

CROSS-REFERENCE TO RELATED APPLICATION

This application claims priority to U.S. Provisional Patent Application Ser. No. 62/849,627, filed May 17, 2019, which is hereby incorporated by reference in its entirety.

FIELD

The present disclosure generally relates to a tissue-removing catheter, and more particular, to a handle of a tissue-removing catheter.

BACKGROUND

Tissue-removing catheters are used to remove unwanted tissue in body lumens. As an example, atherectomy catheters are used to remove material from a blood vessel to open the blood vessel and improve blood flow through the vessel. This process can be used to prepare lesions within a patient's coronary artery to facilitate percutaneous coronary angioplasty (PTCA) or stent delivery in patients with severely calcified coronary artery lesions. Atherectomy catheters typically employ a rotating element which is used to abrade or otherwise break up the unwanted tissue.

SUMMARY

In one aspect, a tissue-removing catheter for removing tissue in a body lumen generally comprise a catheter body assembly having an axis and proximal and distal end portions spaced apart from one another along the axis. At least a portion of the catheter body assembly is sized and shaped to be received in the body lumen. A handle is mounted to the proximal end portion of the catheter body assembly and operable to cause rotation of the catheter body assembly. The handle includes internal handle components that interface with the catheter body assembly. The internal handle components provide at least four interface locations spaced axially along the catheter body assembly. A tissue-removing element is mounted on the distal end portion of the catheter body assembly. The tissue-removing element is configured to remove the tissue as the tissue-removing element is rotated by the catheter body assembly within the body lumen.

In another aspect, a handle of a tissue-removing catheter for removing tissue in a body lumen is operable to cause rotation of a catheter body assembly of the tissue-removing catheter. The handle comprises a housing and internal components within the housing configured to interface with the catheter body assembly. The internal handle components provide at least four interface locations spaced axially along the catheter body assembly.

In yet another aspect, a tissue-removing catheter for removing tissue in a body lumen generally comprises a catheter body assembly including an elongate body having an axis and proximal and distal end portions spaced apart from one another along the axis. The elongate body is sized and shaped to be received in the body lumen. A liner assembly is received within the elongate body and defines a guidewire lumen. The liner assembly isolates an interior of the guidewire lumen from the elongate body such that rotational and torsional forces are not transferred from the elongate body to the interior of the guidewire lumen when the elongate body is rotated during operation of the tissue-removing catheter. A handle is mounted to the proximal end portion of the catheter body assembly and is operable to cause rotation of the elongate body. The handle includes internal handle components that interface with the liner assembly and elongate body to stabilize and align the liner assembly and elongate body to center the liner assembly within the elongate body for facilitating the isolation of the interior of the guidewire lumen of the liner assembly from the elongate body.

BRIEF DESCRIPTION OF THE DRAWINGS

FIG. 19 is an exploded section of the drive assembly showing the drive coil received therein;

FIG. 20 is a partially exploded section of the drive assembly showing the drive coil received therein and a lock attached to a tube insert;

FIG. 21 is a section of the drive assembly showing the drive coil received therein and the tube insert and lock attached to a gear insert;

Corresponding reference characters indicate corresponding parts throughout the drawings.

DETAILED DESCRIPTION

Figure 1:
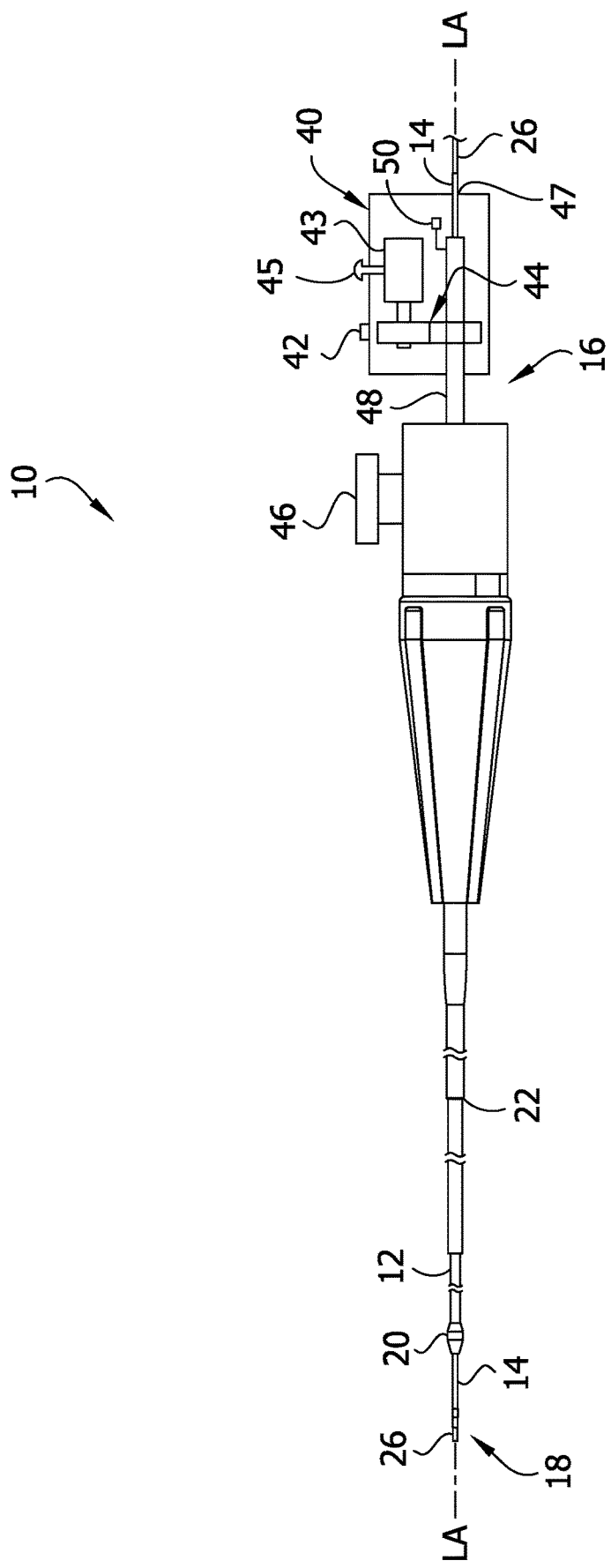
FIG. 1 is a schematic illustration of a catheter of the present disclosure.

Referring to the drawings, and in particular FIG. 1, a rotational tissue-removing catheter for removing tissue in a body lumen is generally indicated at reference number 10. The illustrated catheter 10 is a rotational atherectomy device suitable for removing (e.g., abrading, cutting, excising, ablating, etc.) occlusive tissue (e.g., embolic tissue, plaque tissue, atheroma, thrombolytic tissue, stenotic tissue, hyperplastic tissue, neoplastic tissue, etc.) from a vessel wall (e.g., coronary arterial wall, etc.). The catheter 10 may be used to facilitate percutaneous coronary angioplasty (PTCA) or the subsequent delivery of a stent. Features of the disclosed embodiments may also be suitable for treating chronic total occlusion (CTO) of blood vessels, and stenoses of other body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Removal of such material can thus be beneficial to maintain patency of the body lumen.

The catheter 10 is sized for being received in a blood vessel of a subject. Thus, the catheter 10 may have a maximum size of 3, 4, 5, 6, 7, 8, 9, 10, or 12 French (1, 1.3, 1.7, 2, 2.3, 2.7, 3, 3.3, or 4 mm) and may have a working length of 20, 30, 40, 60, 80, 100, 120, 150, 180 or 210 cm depending of the body lumen. While the remaining discussion is directed toward a catheter for removing tissue in blood vessels, it will be appreciated that the teachings of the present disclosure also apply to other types of tissue-removing catheters, including, but not limited to, catheters for penetrating and/or removing tissue from a variety of occlusive, stenotic, or hyperplastic material in a variety of body lumens.

Figure 2:
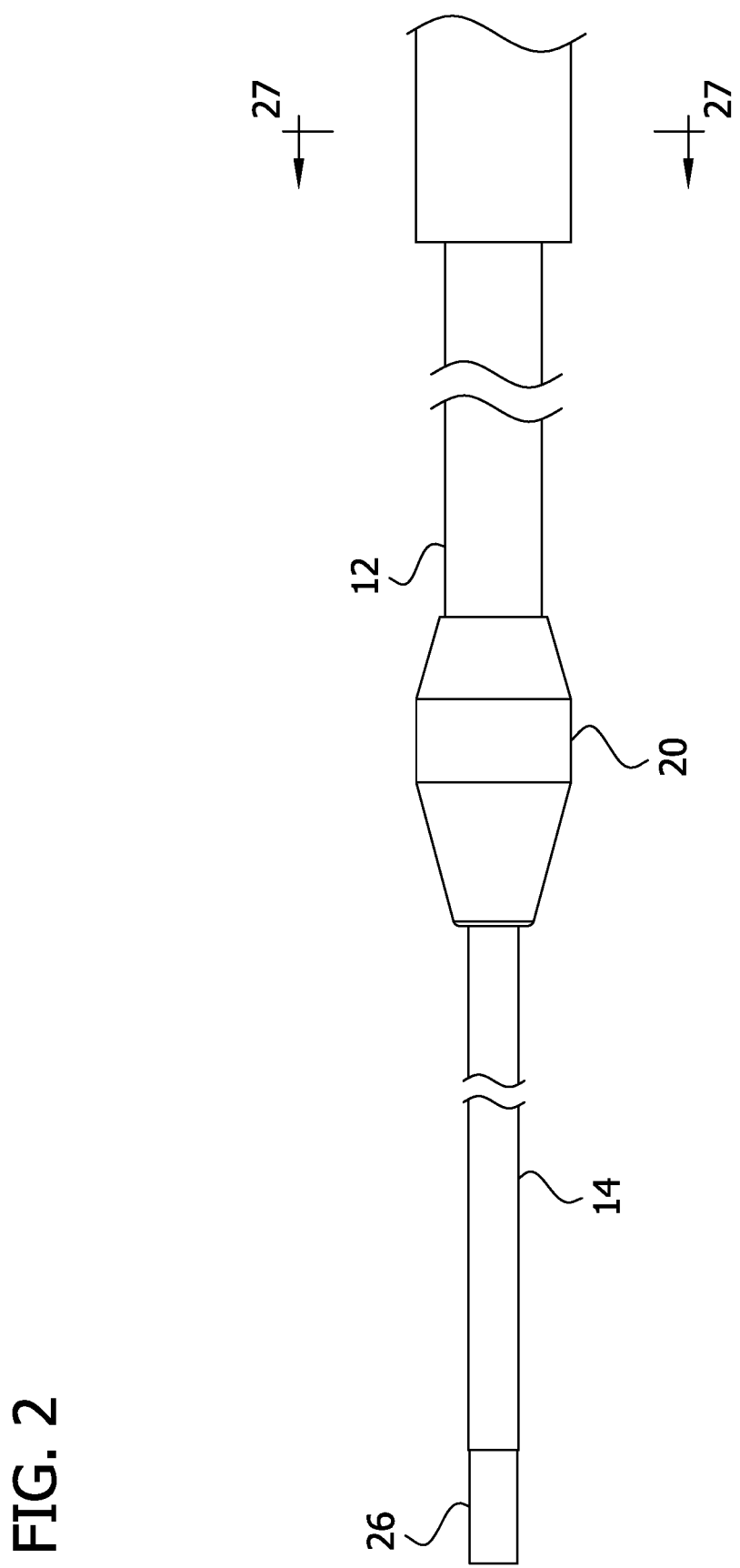
FIG. 2 is an enlarged elevation of a distal end portion of the catheter.
Figure 3:
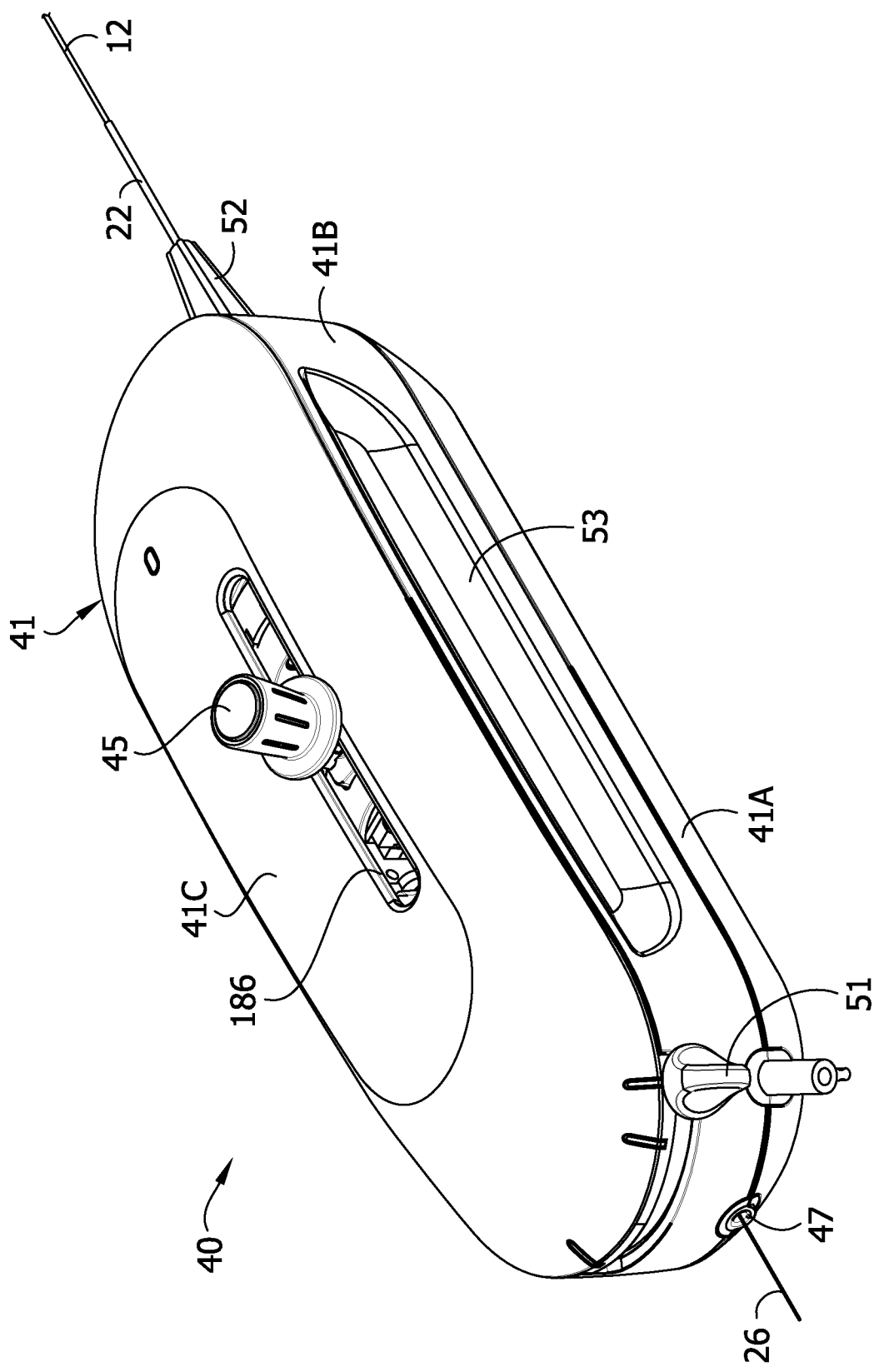
FIG. 3 is a top perspective of a handle of the catheter.
Figure 4:
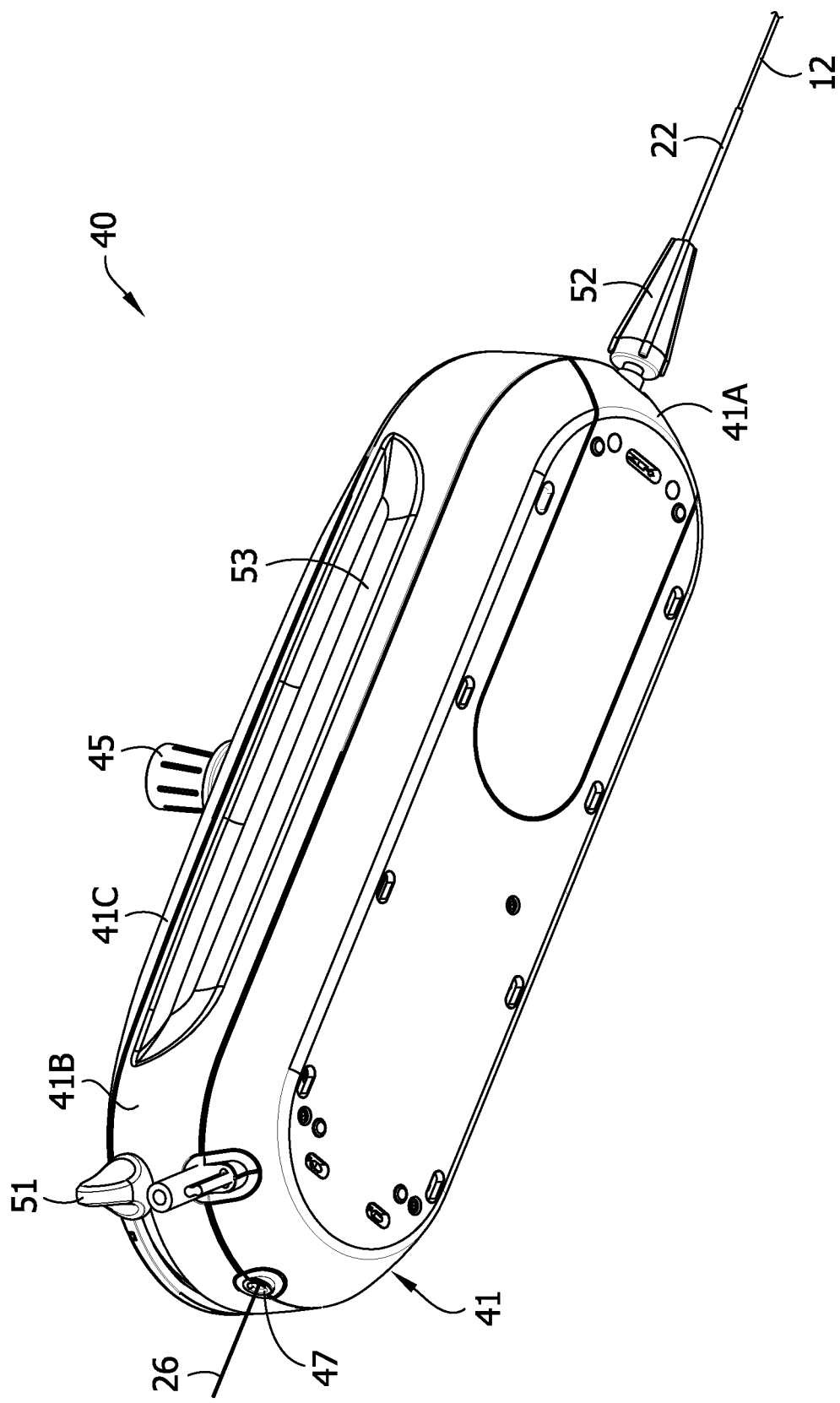
FIG. 4 is a bottom perspective of the handle.
Figure 5A:
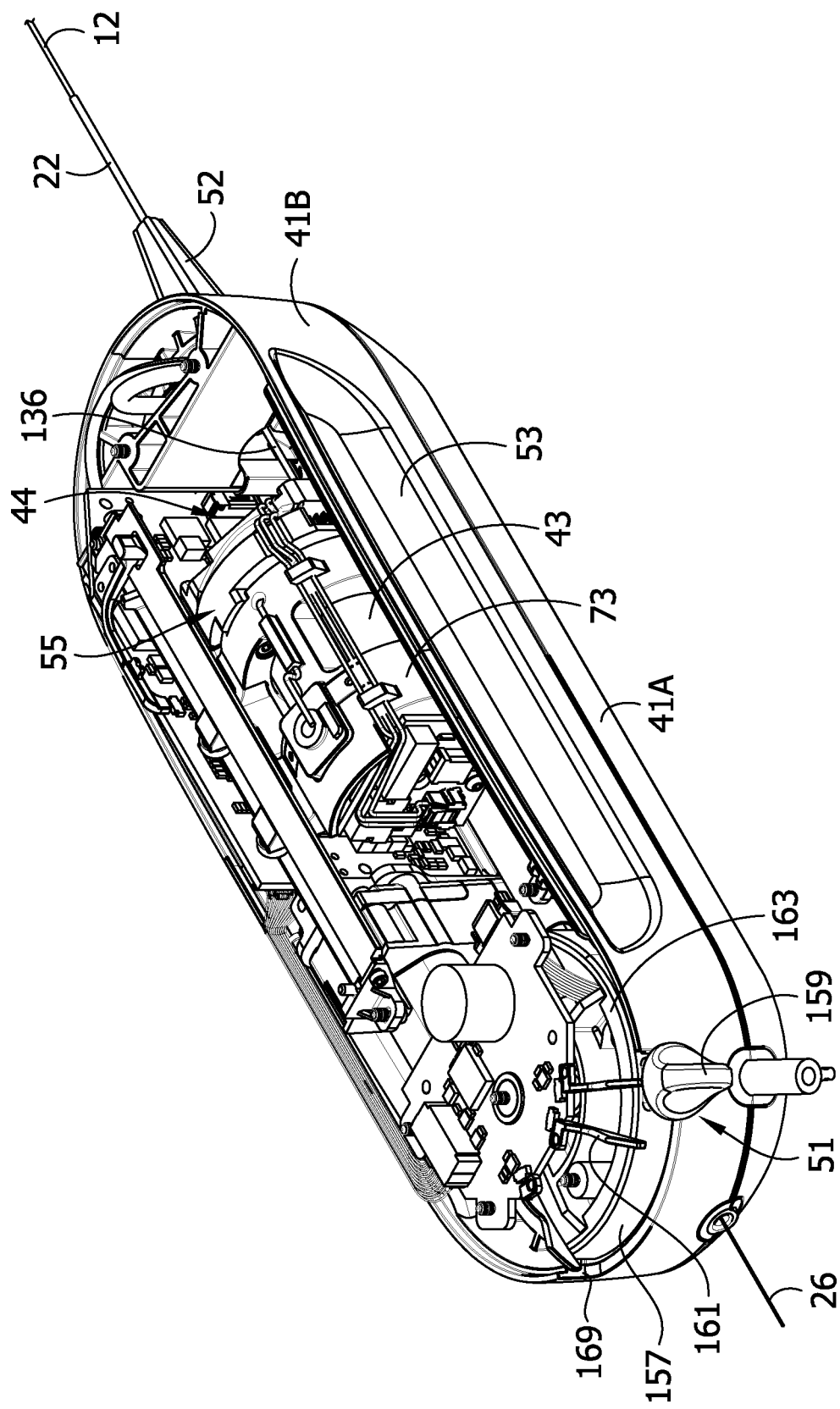
FIG. 5A is a top perspective of the handle with a top housing section removed.
Figure 5B:
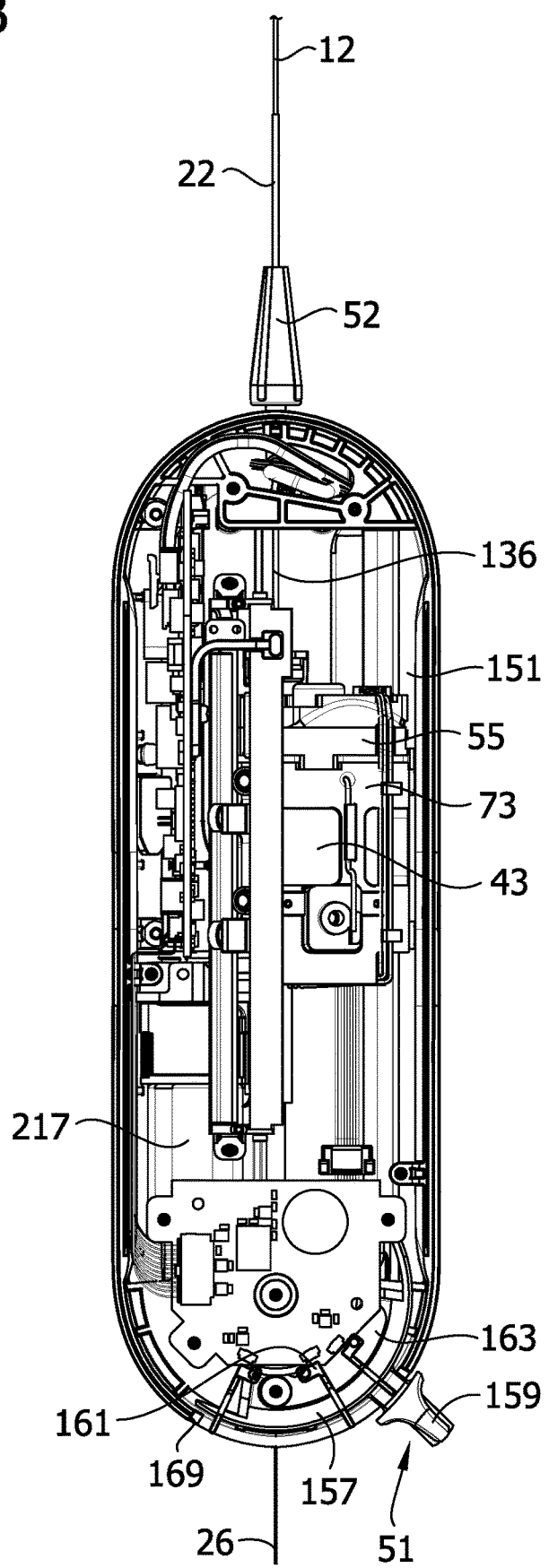
FIG. 5B is a top view of the handle in FIG. 5A.
Figure 6:
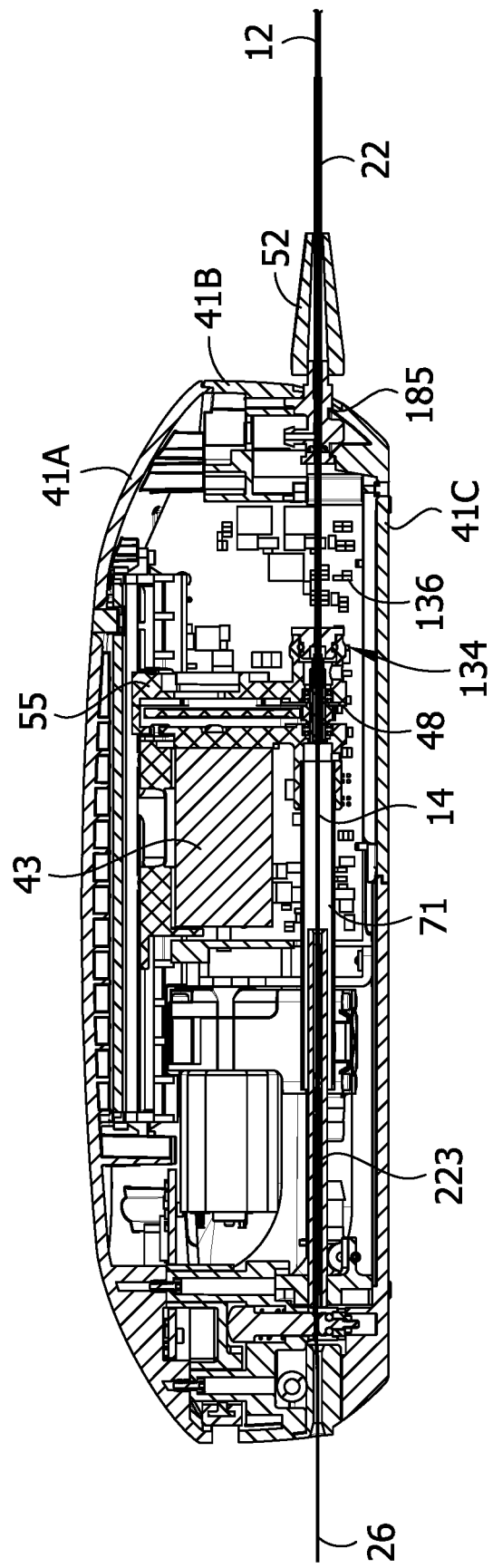
FIG. 6 is a cross section of the handle.

Referring to FIGS. 1 and 2, the catheter 10 comprises an elongate drive coil 12 (broadly, an elongate body) disposed around an elongate inner liner 14. The drive coil 12 and inner liner 14 extend along a longitudinal axis LA of the catheter from a proximal end portion 16 to a distal end portion 18 of the catheter. A tissue-removing element 20 is disposed on a distal end of the drive coil 12 and is configured for rotation to remove tissue from a body lumen as will be explained in greater detail below. An isolation sheath 22 (FIG. 1) is disposed around the drive coil 12. The drive coil 12 and the inner liner 14 are both configured to translate relative to the isolation sheath 22. The catheter 10 is sized and shaped for insertion into a body lumen of a subject. The isolation sheath 22 isolates the body lumen from at least a portion of the drive coil 12 and inner liner 14. The inner liner 14 defines a guidewire lumen 24 (FIG. 27) for slidably receiving a guidewire 26 therein so that the catheter 10 can be advanced through the body lumen by traveling along the guidewire. The guidewire can be a standard 0.014-inch outer diameter, 300 cm length guidewire. In certain embodiments, the inner liner 14 may have a lubricious inner surface for sliding over the guidewire 26 (e.g., a lubricious surface may be provided by a lubricious polymer layer or a lubricious coating). In the illustrated embodiment, the guidewire lumen 24 extends all the way through the length of the inner liner 14 such that the guidewire 26 is extendable along an entire working length of the catheter 10. In one embodiment, the overall working length of the catheter 10 may be between about 135 cm (53 inches) and about 142 cm (56 inches). In use, the guidewire 26 may extend about 40 mm (1.6 inches) past a distal end of the inner liner 14.

Referring to FIGS. 1 and 3-7, the catheter 10 further comprises a handle 40 secured at a proximal end of the isolation sheath 22. The handle 40 comprises a housing 41 that supports the components of the handle. The housing 41 has a generally elongate egg shape and includes as plurality of housing sections secured together to enclose the internal components of the handle 40. In the illustrated embodiment, the housing 41 includes a bottom housing section 41A, a middle housing section 41B secured to the top of the bottom housing section, and a top housing section 41C secured to the top of the middle housing section. The middle housing section 41B has a generally racetrack shape, and the bottom and top housing sections 41A, 41C are generally dome shaped. The bottom housing section 41A has a flat bottom surface for resting the housing 41 on a support surface. A mode selector 51 is mounted generally between the middle housing section 41B and the top housing section 41C and defines a portion of the housing 41. As will be explained in greater detail below, the mode selector 51 is configured to selectively place the catheter 10 in a plurality of modes and to lock the guide wire in place in at least one of the modes. The middle housing section 41B has recessed areas 53 on each side to provide a gripping area for the housing 41. In one embodiment, the bottom housing section 41A is removable from the middle housing section 41B to provide access to the components of the handle 40 in the interior of the housing 41 by a user. It will be understood that the housing 41 can have other shapes and configurations without departing from the scope of the disclosure.

Figure 16:
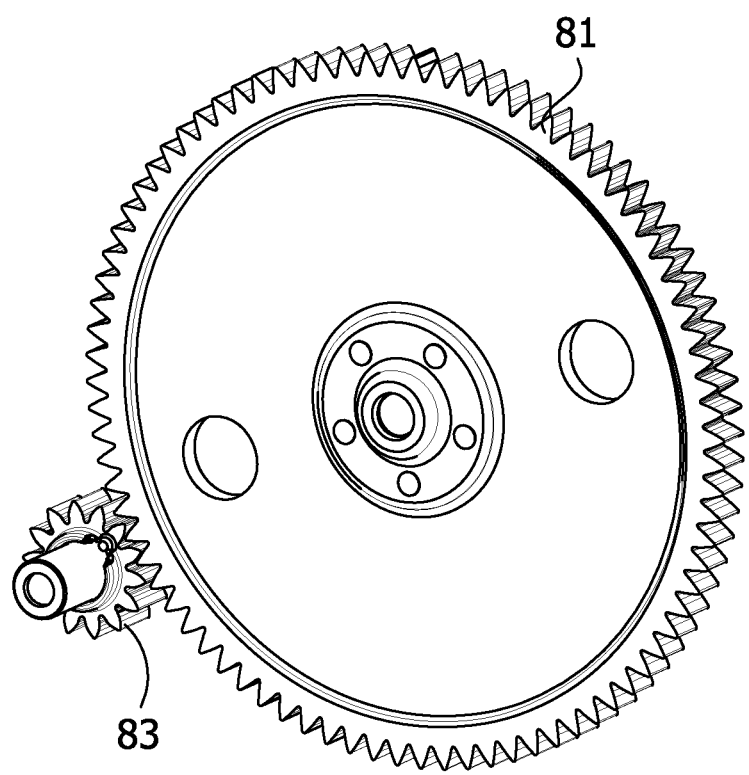
FIG. 16 is a perspective of gears of the gear assembly.
Figure 17:
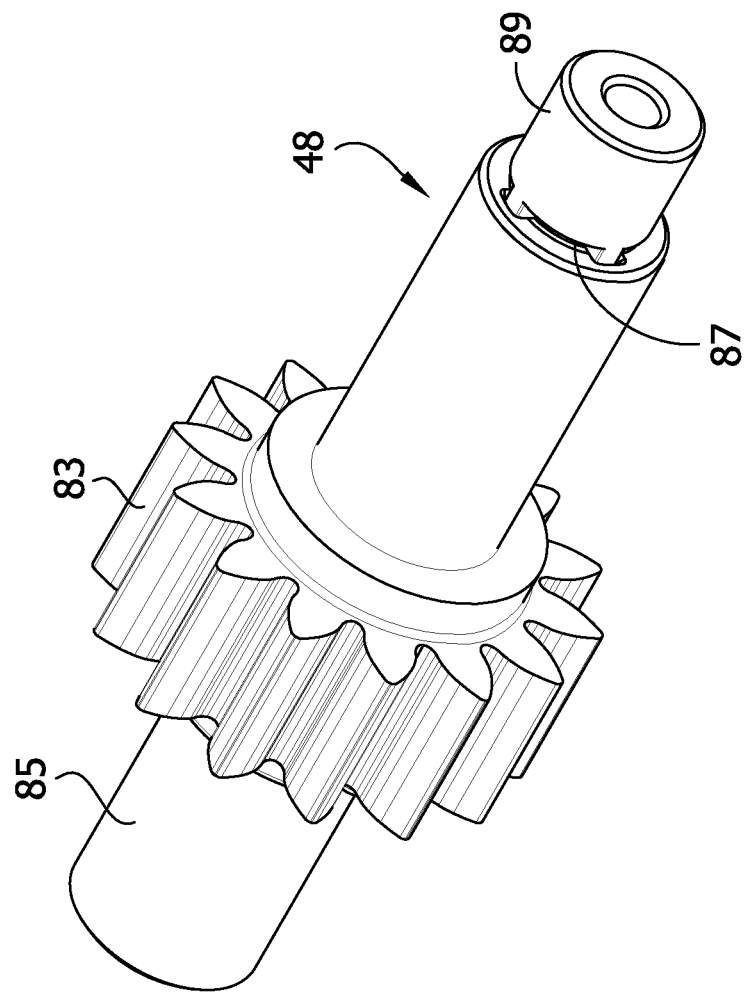
FIG. 17 is a perspective of a driven gear and a drive assembly in the handle.
Figure 18:
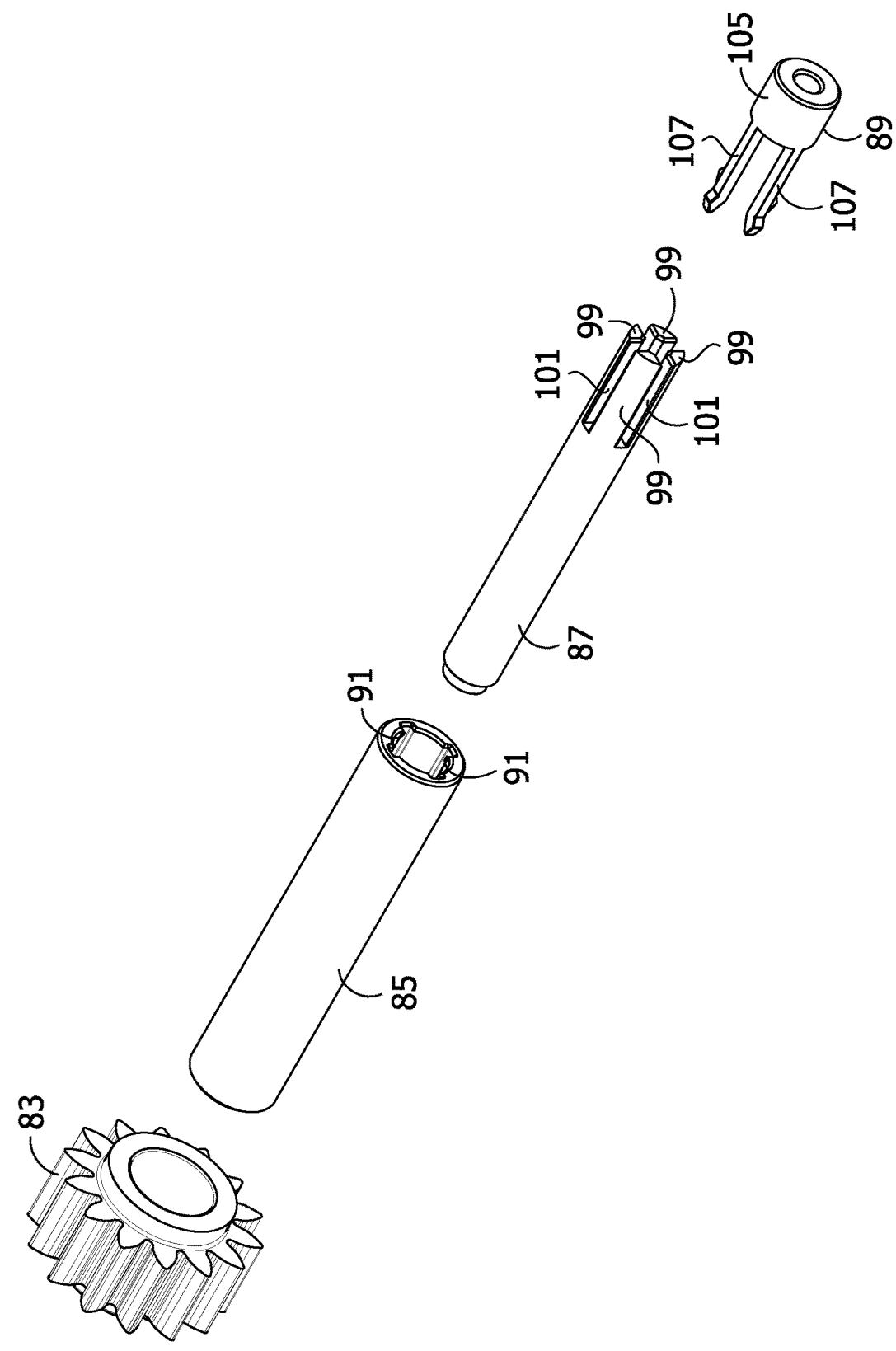
FIG. 18 is an exploded view of the driven gear and drive assembly in FIG. 17.

Referring to FIGS. 1, 3, 5A-11, and 13-16, the housing 41 supports an actuator 42 (e.g., a lever, a button, a dial, a switch, or other device) configured for selectively actuating a motor 43 disposed in the handle to drive rotation of the drive coil 12, and a tissue-removing element 20 mounted at the distal end of the drive coil. The motor 43 is configured to rotate the drive coil 12 and tissue-removing element 20 at speeds of greater than about 80,000 RPM. The motor 43 is coupled to the drive coil 12 by a gear assembly 44 and drive assembly 48 supported within the housing 41. The gear assembly 44 comprises a gearbox housing 55 that mounts and at least partially encloses a pair of gears for transferring the rotation of a shaft of the motor 43 to the drive coil 12. The gearbox housing 55 includes a main housing section 61 and a front housing section 63. The front housing section 63 is secured to the main housing section 61 by a plurality of fasteners 65. Clips 67 further secures the front housing section 63 to the main housing section 61. In one embodiment, the main housing section 61 and front housing section 63 may have a keyed engagement that locates the housing sections with respect to each other and prevents angular rotation of the housing sections relative to each other. For example, the keyed engagement may comprise a plurality of projections and recessed surfaces on each of the housing sections 61, 63 whereby a projection on the main housing section is received at a recessed surface on the front housing section, and a projection of the front housing section is received at a recessed surface on the main housing section. To this effect, the projections on one of the housing sections 61, 63 would be located adjacent to a projection on the other of the housing sections generally preventing one housing section from being rotated relative to the other housing section. The main housing section 61 includes a sleeve portion 69 on a proximal side of the main housing section that receives an end of a buckle tube 71. The main housing section 61 also attaches to a carriage or advancer frame 73 via fasteners 75 for moving the motor 43 and gear assembly 44 within the housing 41. Further, attaching the gearbox housing 55 to the distal end of the advancer frame 73 secures the motor 43 in the advancer frame so that the motor moves along with the advancer frame. The front hosing section 63 has a sleeve portion 77 on a distal side of the front housing section that receives washers (not shown) for disposal around the drive assembly 48. A driver gear 81 is attached to the motor shaft (not shown) such that the driver gear rotates with the motor shaft when the motor 43 is activated. A driven gear 83 (FIG. 16) is in mesh with the driver gear 81 so that rotation of the driver gear causes the driven gear to rotate in the opposite direction. The drive assembly 48 attaches the driven gear 83 to the drive coil 12 so that the rotation of the driven gear causes the drive coil to rotate. A controller 50 may be provided in the handle 40. The controller 50 may be programmed to control operation of the catheter.

It is understood that other suitable actuators, including but not limited to touchscreen actuators, wireless control actuators, automated actuators directed by a controller, etc., may be suitable to selectively actuate the motor in other embodiments. In some embodiments, a power supply may come from a battery (not shown) contained within the handle 40. The battery can provide the current source for the guidewire detection circuit. In other embodiments, the power supply may come from an external source.

Referring to FIGS. 17-22C, the drive assembly 48 comprises a gear insert 85 received in the driven gear 83, a tube insert 87 received in the gear insert, and a lock 89 attached to a distal end of the tube insert. In one embodiment, the gear insert 85 is press fit into the driven gear 83. The gear insert 85 comprises a cylindrical member having a uniform outer diameter extending along a length of the cylindrical member and circumferentially around the cylindrical member. An inner surface of the cylindrical member includes a plurality of circumferentially spaced channels 91 that extend along the length of the cylindrical member and thereby define an inner diameter of the cylindrical member that is non-uniform. The channels 91 extend from the distal end of the cylindrical member to an intermediate location between the distal and proximal ends of the cylindrical member. At the end of the channels 91 is an annular recess 93. The inner surface of the cylindrical member tapers at the proximal end forming an annular shoulder 95 and a reduced inner diameter at the proximal end. The gear insert 85 may be formed from any suitable material including without limitation, stainless steel and Peek. In the illustrated embodiment, the gear insert 85 is formed separately from the driven gear 83. However, the gear insert 85 could be formed integrally with the driven gear 83.

The tube insert 87 comprises a tubular member having a reduced outer diameter proximal end margin forming a shoulder 97 near the proximal end of the tube insert. A plurality of circumferentially spaced projections 99 extend along a distal end margin of tube insert 87. In the illustrated embodiment, there are four projections 99 each having a triangular cross-section. Another number of projections 99 could be used without departing from the scope of the disclosure. The projections 99 define circumferentially spaced gaps 101 between the projections. The outer diameter of the tube insert 87 is sized so that it can be received in the gear insert 85. When the tube insert 87 is inserted into the gear insert 85 the shoulder 97 on the tube insert engages the shoulder 95 in the gear insert to provide a stop for locating the tube insert in the gear insert. This hard stop holds the tube insert 87 in place in the gear insert 85 when the drive coil 12 and drive assembly 48 are placed in compression. The tube insert 87 also defines a passage extending longitudinally through the tube insert and which is sized to receive the drive coil 12. The drive coil 12 is fixedly attached to the tube insert 87 such as by welding. The tube insert 87 may be formed from any suitable material including without limitation, stainless steel. The gear insert 85 and tube insert 87 may together be broadly considered a gear extension. The gear extension may include both or only one of the gear insert 85 and tube insert 87.

The lock 89 comprises a tubular portion 105 and a plurality of fingers 107 projecting from a proximal end of the tubular portion. In the illustrated embodiment, there are four fingers 107. However, another number of fingers 107 could be used without departing from the scope of the disclosure. Each of the finger 107 has an elongate portion 109 and a hook portion 111 projecting laterally from the elongate portion away from a central axis of the lock 89. Prior to inserting the tube insert 87 into the gear insert 85, the lock 89 is engaged with the tube insert by inserting the fingers 107 in the gaps 101 in the tube insert (FIG. 20). Therefore, when the tube insert 87 is inserted into the gear insert 85, the fingers 107 will flex inward and ride along the channels 91 in the gear insert until they reach the annular recess 93 at the end of the channels where the fingers are then permitted to flex outward such that the hook portions 111 snap into the recess to secure the lock 89 in the gear insert. Thus, the lock 89 couples the drive coil 12 to the gear assembly 44 in the handle 40. This configuration provides overlap of the lock 89 with the gear insert 85 and the tube insert 87 which facilitates a better transfer of rotation to the drive coil 12 and allows the drive assembly 48 to better withstand the torque applied to the drive assembly. The connection between the lock 89 and the gear insert 85 also holds the drive assembly 48 together when the drive coil 12 and drive assembly 48 are placed in tension. The tubular portion 105 of the lock 89 also defines a passage sized to receive the drive coil 12. The lock 89 may be formed from any suitable material including without limitation, stainless steel and Peek. The construction of the drive assembly 48 also allows the drive assembly to be connected to the gear assembly 44 by inserting the drive assembly through the distal end of the gear assembly. This prevents the need for access to the proximal end of the handle 40 or for additional parts required in the assembly of a conventional auto chuck mechanism. In the illustrated embodiment, an annular recess 93 is shown in the gear insert 85. However, the gear insert 85 could include a plurality of discrete receptacles at the ends of the channels 91 for receiving the hook portions 111 of the lock 89.

Figure 22A:
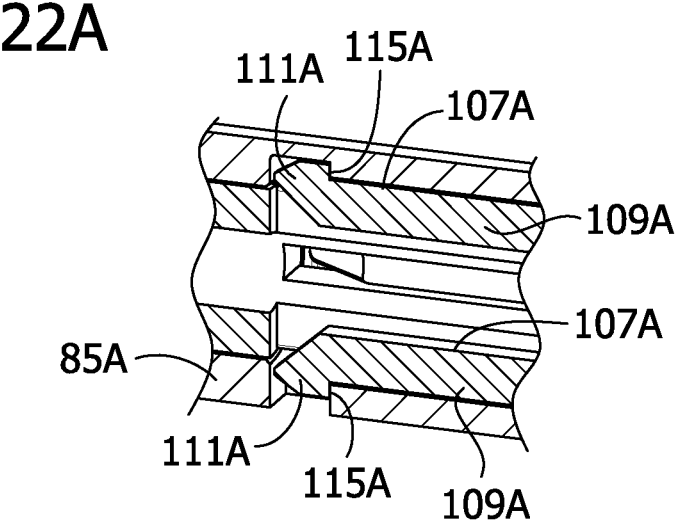
FIG. 22A is an enlarged fragmentary perspective of a drive assembly of another embodiment.
Figure 22B:
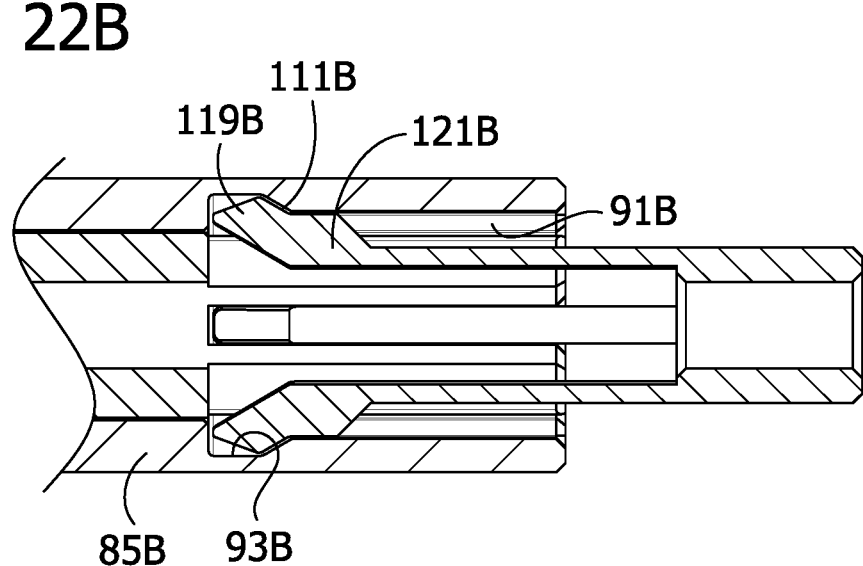
FIG. 22B is a fragmentary section of a drive assembly of another embodiment.
Figure 22C:
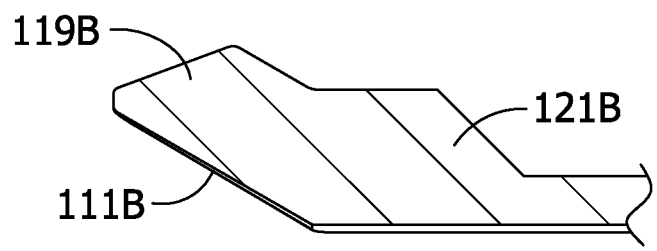
FIG. 22C is a fragmentary section of a portion of a lock of the drive assembly in FIG. 22B.
Figure 23:
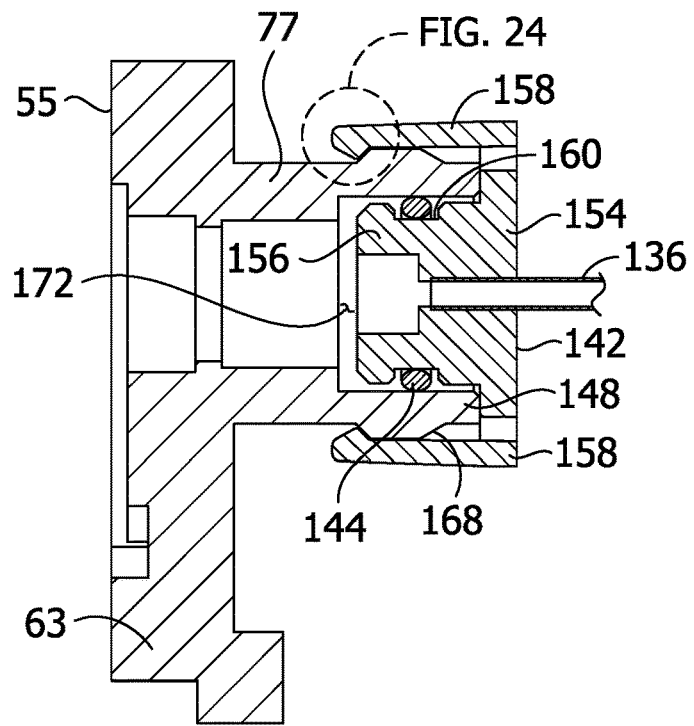
FIG. 23 is a section of a travel sheath interface assembly in the handle.
Figure 24:
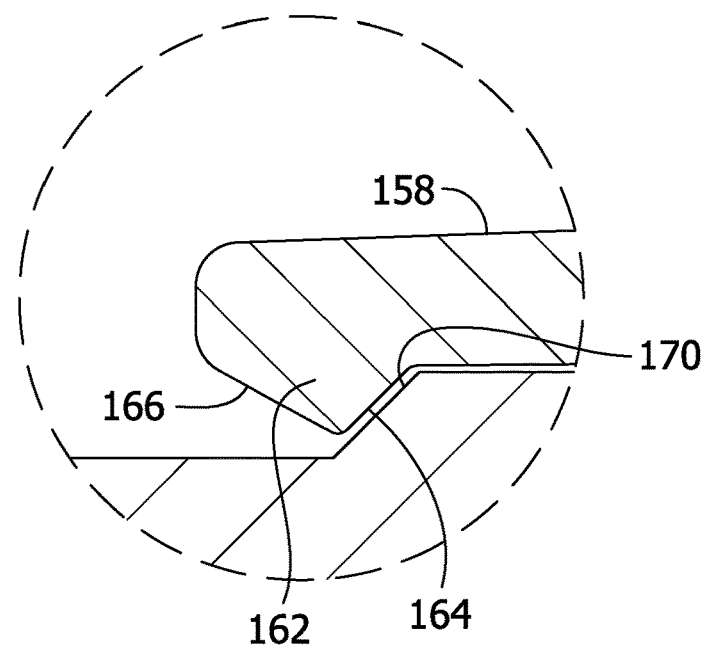
FIG. 24 is an enlarged fragmentary section of FIG. 23.
Figure 25:
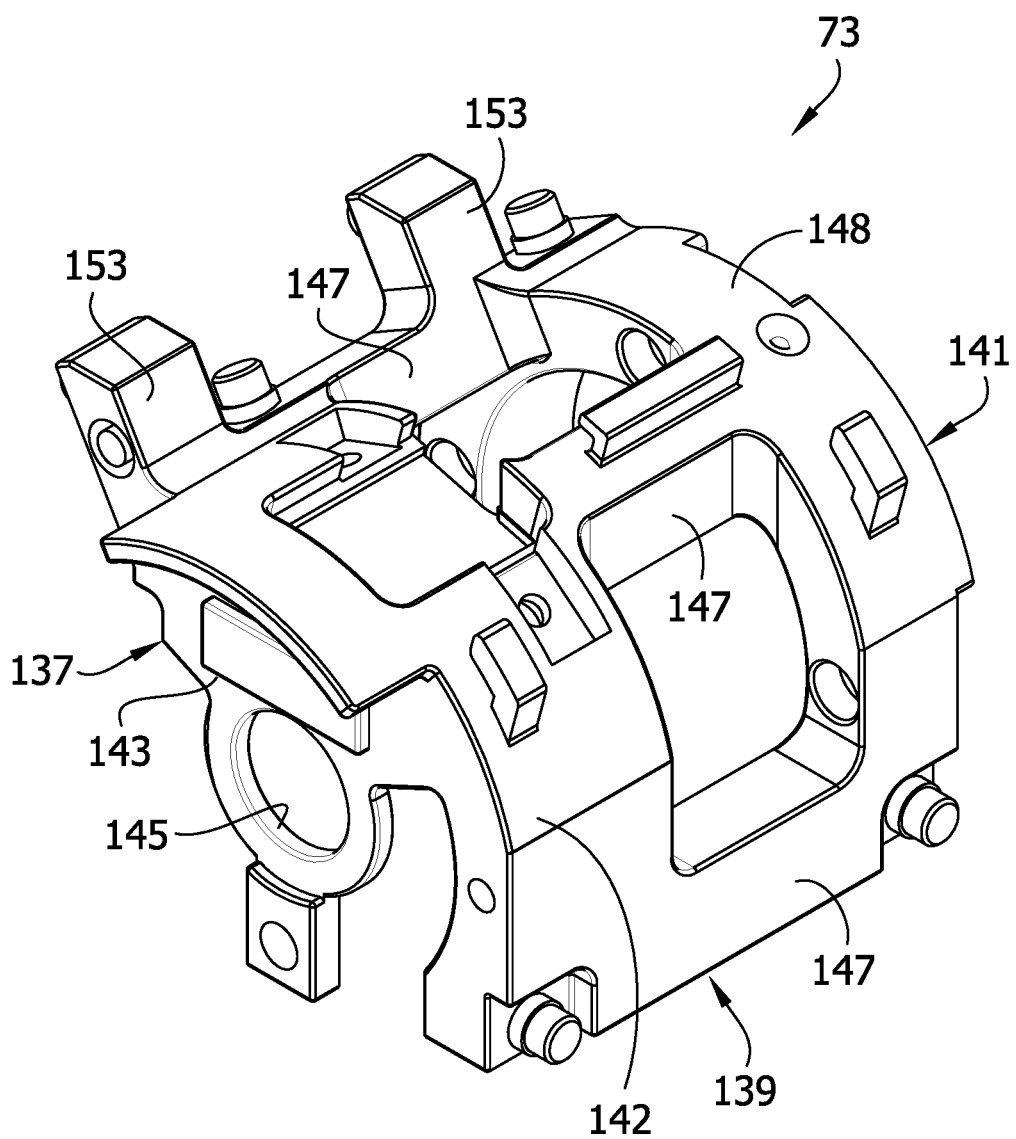
FIG. 25 is a perspective of an advancer frame in the handle.

In one embodiment (FIG. 21), the hook portion 111 projects from the elongate portion 109 such that a gear insert engagement surface 115 of the hook portion extends at an obtuse angle from the elongate portion. In this embodiment, the lock 89 may be detached from the gear insert 85 by applying a sufficient pulling force on the tubular portion 105 to withdraw the fingers 107 from the gear insert. During use, however, the angled face utilizes the pull force transmitted from the drive coil 12 through the tube insert 87 to the lock 89 to provide extra strength to the lock's snap feature to achieve the pull force requirement. In another embodiment (FIG. 22A), a gear insert engagement surface 115A extends orthogonally from the elongate portion 109A of finger 107A. In this embodiment, recesses 93A in the gear insert 85A may be open at the outer surface of the gear insert to allow a tool to be inserted into the receptacle to release the hook portion 111A from the receptacle. A wall 117A of the recess 93A in the gear inert 85A is configured to match the gear insert engagement surface 115A of the fingers 107A so that a sound locking connection is made between the lock 89A and the gear insert 85A. In FIGS. 22B and 22C, a hook portion 111B has a first section 119 that is configured to be received in a recess 93B in the gear insert 85B, and a second section 121B configured to engage the channel 91B in the gear insert when the first section is received in the receptacle.

Further, the drive assembly 48 reduces the number of components for interfacing with the drive coil 12 to couple the handle 40 to the catheter body. The drive assembly 48 also enables assembly and disassembly of the drive assembly by only requiring access to the distal end of the gear shaft through the gearbox 55. This means the handle 40 can be closed to protect the internal components, such as the internal electronics. Additionally, the design of the drive assembly 48 facilitates decoupling of the catheter body components from the handle 40. Thus, the handle 40 can be recouple with another catheter body and/or any reworking tasks can be performed on the handle. Therefore, the handle 40 does not have to be discarded with the catheter body after use.

Figure 14:
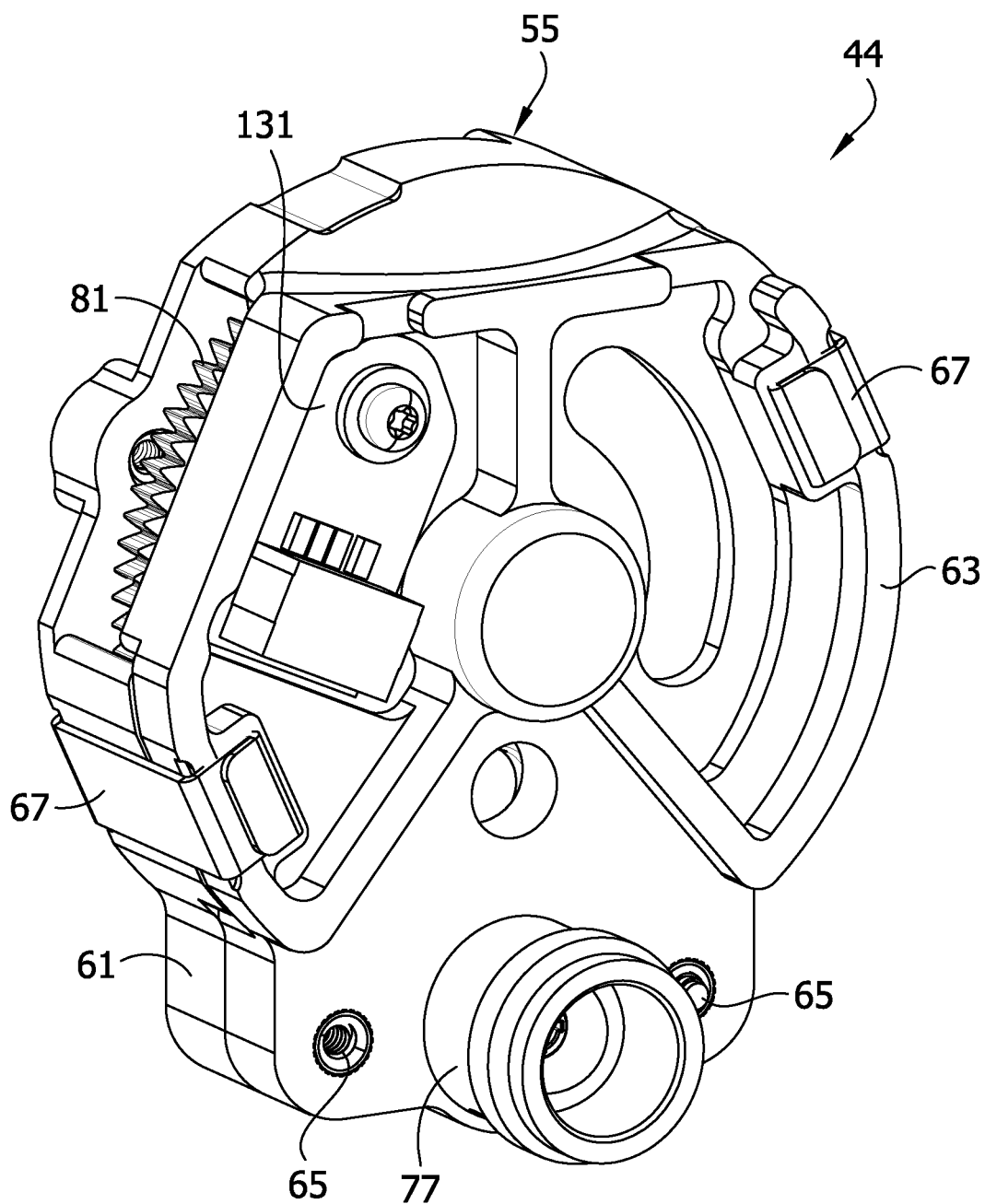
FIG. 14 is a front perspective of the gear assembly.
Figure 15:
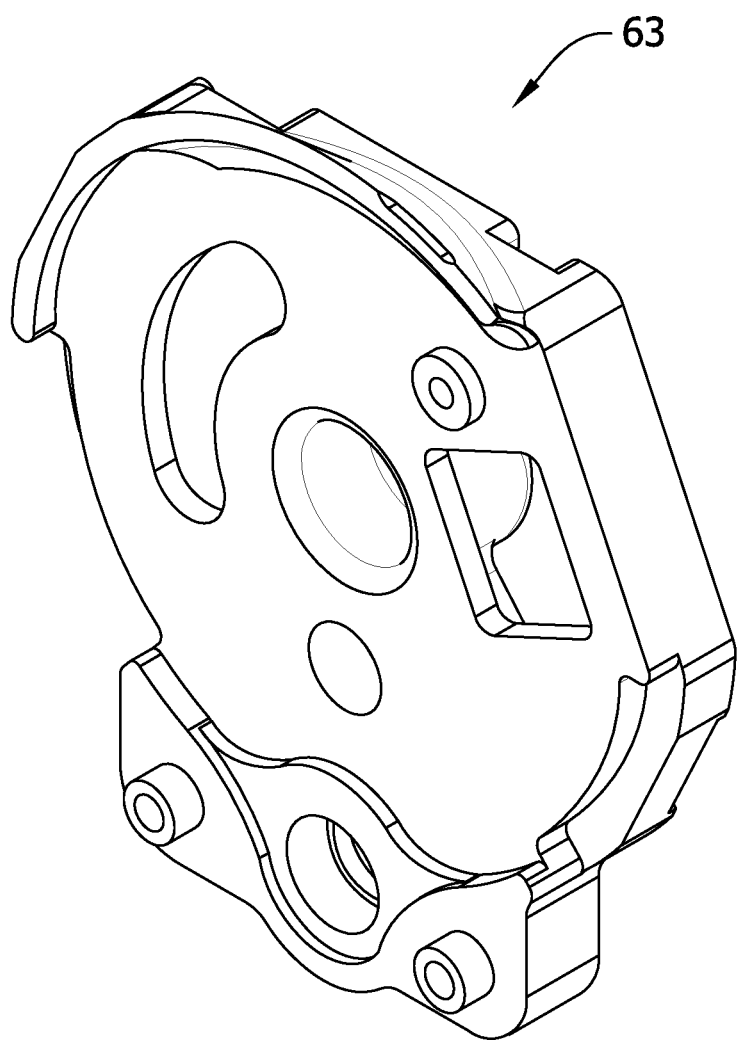
FIG. 15 is a perspective of a front housing section of the gear assembly.

Referring to FIG. 14, a sensor 131 may be mounted to the gearbox housing 55 and configured to detect rotation of the driver gear 81. For example, the sensor 131 may emit a signal toward a surface of the driver gear 81 to detect the rotation of the driver gear. Gear rotation can be used to determine the operability of the motor 43.

Referring to FIGS. 6, 7, 10B-12, 23, and 24, a travel sheath interface assembly 134 is mounted on the distal side of the front housing section 63 of the gearbox housing 55 and secures a travel sheath 136 in the handle 40. The travel sheath interface assembly 134 comprises a travel sheath connector 142 attached to a distal end of the sleeve portion 77 of the front housing section 63 of the gearbox housing 55, and a seal (e.g., o-ring) 144 received between the sleeve portion and the travel sheath connector. The travel sheath connector 142 is snap fit onto the sleeve portion 77 of the front housing section 63 of the gearbox housing 55. The travel sheath connector 142 includes a plate portion 154, an insert portion 156 extending proximally from a center of the plate portion, and a pair of arms 158 at the periphery of the plate portion that also extend proximally from the plate portion. The insert portion 156 defines an annular groove 160 that receives the seal 144. Each arm 158 has a hook 162 at its free end. The arms 158 extends along sides of the sleeve portion 77, and the hooks 162 clip around the side of the sleeve portion to attach the travel sheath connector 142 to the sleeve portion by a snap fit engagement. The hooks 162 project laterally inward from a longitudinal extension of the arms 158 such that a gearbox retention surface 164 of the hooks extends at about a 45-degree angle to a longitudinal axis of the arm. This facilitates removal of the travel sheath connector 142 from the sleeve portion 77 with a sufficient distal puling force. A ramp surface 166 on each arm 158 extends at about a 30-degree angle to the longitudinal axis of the arm to facilitate attachment of the travel sheath connector 142 to the sleeve portion 77. The ramp surfaces 166 are configured ride up a first sloped surface 168 on the sleeve portion 77. The gearbox retention surfaces 164 slide down a second sloped surface 170 on the sleeve portion to clip the travel sheath connector 142 onto the sleeve portion. With the travel sheath connector 142 attached to the sleeve portion 77, the o-ring 144 provides a seal to the gearbox. A passage 172 extends through the travel sheath interface assembly 134 and is defined by aligned axial holes in the sleeve portion 77 of the front housing section 63 of the gearbox housing 55 and travel sheath connector 142. The travel sheath 136 is fixedly received in the axial hole in the travel sheath connector 142 to attach the travel sheath to the travel sheath interface assembly 134. The travel sheath 136 is sized to receive the drive coil 12 within an interior of the travel sheath and extends from the travel sheath interface assembly 134 to isolation sheath interface assembly 185. The travel sheath assembly 134, including the travel sheath 136, aligns and stabilizes the drive coil 12 such that the extension of the drive coil is maintained along an axis during operation of the catheter 10. The travel sheath 136 may be considered part of the travel sheath assembly 134.

Referring to FIGS. 1, 5B, 8, and 25, a slide or advancer 45 is positioned on the handle 40 and is operatively coupled to the drive coil 12 for movement of the drive coil relative to the handle to advance and retract the drive coil and tissue-removing element 20. The housing 41 of the handle 40 may define a slot 186 which limits the movement of the slide 45 relative to the handle. Thus, the length of the slot determines the amount of relative movement between the drive coil 12 and the handle 40. In one embodiment, the slot has a length of about 70 mm (2.8 inches). The slide 45 is operatively attached to the advancer frame 73 so that movement of the slide causes movement of the advancer frame. The advancer frame 73 comprises an arch shaped body including a rear section 137, a middle section 139, and a front section 141. The rear section 137 include an arcuate portion 142 that extends from a first side of the frame 73 generally to an opposite second side of the frame and plate portion 143 having an opening 145 formed therein. In the illustrated embodiment, the opening 145 is round for receiving an end of the motor 43. The middle section 139 includes a plurality of circumferentially spaced body portions 147 defining open spaces between the body portions. The front section 141 includes an arcuate portion 148 that extends from the first side of the frame 73 to the second side. The arch shape body of the frame 73 is configured to slidingly receive the cylindrically shaped motor 43 such that the motor extends from the front section 141 to the rear section 137 with the end of the motor held inside the opening 145 in the rear section. A first pair of bearings 149 (FIG. 8) are mounted at the bottom of the rear and front sections 137, 141, respectively, on the first side of the frame 73. The bearings 149 are seated on a ledge 151 (FIG. 5B) on the middle housing section 41B so that the bearings can slide along the ledge to facilitate movement of the frame 73 in the housing 41. A second pair of bearings 151 (FIG. 8) are mounted at the top of the second side of the frame 73 on the middle section 139 and the front section 141, respectively. Arms 153 extend from the rear section 137 and middle section 139 and have bearings 155 mounted thereon. The bearings 155 (FIG. 8) on the arms 73 engage an underside of the top housing section 41C to facilitate movement of the frame 73 in the housing 41.

Referring to FIGS. 3, 5A, 5B, and 8-9B, the mode selector 51 comprises a guide portion 157 that is supported by the housing 41, a lever 159 attached to the guide portion and actuatable to move the guide portion relative to the housing, and a motor switching portion 161 operatively connected to the guide portion for causing the motor 43 to change its operational state based on the position of the guide portion. In the illustrated embodiment, the guide portion 157 sits on a floor 163 of the middle housing section 41B and pivots relative to the middle housing section. Other engagements between the mode selector 51 and the housing 41 that facilitate the same or other forms of movement of the mode selector are also envisioned. In one embodiment, the lever 159 is actuatable to place the motor 43 in a "standby mode" where the motor is deactivated and the guide wire 26 is unlocked so that the guidewire can be moved relative to the catheter 10. In one embodiment, the "standby mode" is initiated by pivoting the lever 159 to engage one of the stops 169 on the housing 41. The lever 159 is further actuatable to place the motor 43 in a "track mode" where the motor is activated to produce a first output and the guide wide 26 is kept unlocked. The first motor output may be a reduced output which generates a pulsed output and/or a relatively slow rotation of the drive coil 12. The "track mode" may be initiated when the catheter 10 is navigating through a particularly tortuous passage. In the illustrated embodiment, the "track mode" is initiated by pivoting the lever 159 to an intermediate position between the stops 169. The lever 159 is also actuatable to place the motor 43 in an "abrade mode" where the motor activated to produce a second output and the guide wire 26 is locked relative to the catheter 10. The second motor output may be an operational output which is increased over the first output so that a relatively high-speed rotation of the drive coil 12 is achieved. In one embodiment, the motor 43 produces a rotation of about 100,000 RPMs. The "abrade mode" may be initiated when the catheter 10 is operating to remove occlusive tissue from a vessel wall. In one embodiment, the "abrade mode" is initiated by pivoting the lever 159 to engage the other of the stops 169 on the housing 41. Movement of the lever 159 to this position will also cause a locking pin 173 to press against the guide wire 26 locking the guide wire in place.

A guidewire lock 49 (FIGS. 8-9B) may be provided in the handle 40 to lock the guidewire 26 in place relative to the handle. The guidewire lock 49 comprises the locking pin 173 retained in the middle housing section 41B and a spring 175 received around the locking pin. A head of the locking pin 173 engages an underside of the guide portion 157 of the mode selector 51. The spring 175 biases the locking pin away from the guidewire 26. The underside of the guide portion 157 includes a first section 179, a ramp section 181 extending from the first section, and a second section 183 extending from the ramp section such that the second section is recessed below the first section. In the illustrated embodiment, the head of the locking pin 173 is positioned to be engaged by the sections 179, 181, 183 on the underside of the guide portion 157 as the mode selector is moved between the different positions. For example, movement of the mode selector 51 to a first position causes the head of the locking pin 173 to oppose the elevated first section 179 allowing the spring 175 to freely press against the head of the locking pin to space the shaft of the locking pin from engaging the guidewire 26, thus permitting the guidewire to move relative to the catheter 10. Movement of the mode selector 51 to a second position causes the head of the locking pin 173 to oppose the recessed second section 183 causing the guide portion 157 to press down on the locking pin 173 against the bias of the spring 175 moving the locking pin downward to frictionally engage the shaft with the guidewire 26 to lock the guidewire 26 in place. In one embodiment, the guidewire lock 49 is engages the guidewire 26 to lock the guidewire in place when the mode selector 51 is moved to place the catheter 10 in the abrade mode.

Referring to FIGS. 29-34, an isolation sheath interface assembly 185 is disposed at the distal end of the handle 40. The assembly 185 comprises an interface housing 187, a seal (e.g., o-ring) 189 received in a proximal end portion 191 of the interface housing, and a retainer 193 attached to the proximal end of the interface housing to retain the seal to the interface housing. The retainer 193 includes a plate portion 195 and a pair of arms 197 that extend distally from the plate portion. Each arm 197 has a hook 199 at its free end. The arms 197 extends along sides of the proximal end portion 191 of the interface housing 187 and the hooks 199 clip around a distal end of the proximal end portion to attach the retainer 193 to the interface housing by a snap fit engagement. With the retainer 193 attached to the interface housing 187, the plate portion 195 engages the seal 189 to hold the seal in place. The interface housing 187 further includes a first tab 201 on a top of the housing that is received in a slot 203 in the middle section 41B of the housing 41, a second tab 205 on a bottom of the housing and received in a slot 207 in the bottom section 41A of the housing, the proximal end portion 191, and a distal end portion 209 that is disposed between the middle and bottom housing sections 41A, 41B. The engagement of the tabs 201, 205 and the distal end portion 209 of the interface housing 187 with the housing 41 mounts the isolation sheath interface assembly 185 to the housing. The distal end portion 209 also extends into a passage in a hub 52 mounted on the proximal end of the isolation sheath 22 to attach the hub to the handle 40. The hub 52 provides a strain relief function at the junction between the distal end of the housing 41 and the catheter components extending from the housing.

The interface housing 187 also defines a longitudinal passage 211 extending from the proximal end of the interface housing to a distal end of the interface housing. The longitudinal passage 211 receives the travel sheath 136 and drive coil 12 at the proximal end of the interface housing, and the drive coil extends entirely through the housing to the distal end of the housing. The seal 189 is also received in the longitudinal passage 211 and extends around the travel sheath 136 to provide a fluid seal against fluid traveling proximally past the seal. The longitudinal passage 211 also receives the isolation sheath 22 at the distal end of the interface housing 187, and the isolation sheath extends to an intermediate location between the proximal and distal ends of the interface housing. A transverse passage 213 extends from the longitudinal passage 211 to a transverse opening 215 in the interface housing 187. The interface housing 187 also defines a perfusion port 46 for delivering fluid (e.g. saline) between the drive coil 12 and the isolation sheath 22. The transverse passage 213 extends through the perfusion port 46 and thus communicates the perfusion fluid to the longitudinal passage 211. Therefore, the transverse passage 213 through port 46 communicates with a space between the isolation sheath 22 and the drive coil 12 for delivering the fluid to the rotating drive coil. In one embodiment, a micro pump 217 (FIGS. 8 an 9A) may be connected to a fluid (e.g., saline) bag for pumping the fluid through tubing to the perfusion port. A proximal port 47 (FIGS. 1, 3, and 4) in the housing 41 allows for passage of the guidewire 26 through the proximal end of the handle 40.

Figure 27:
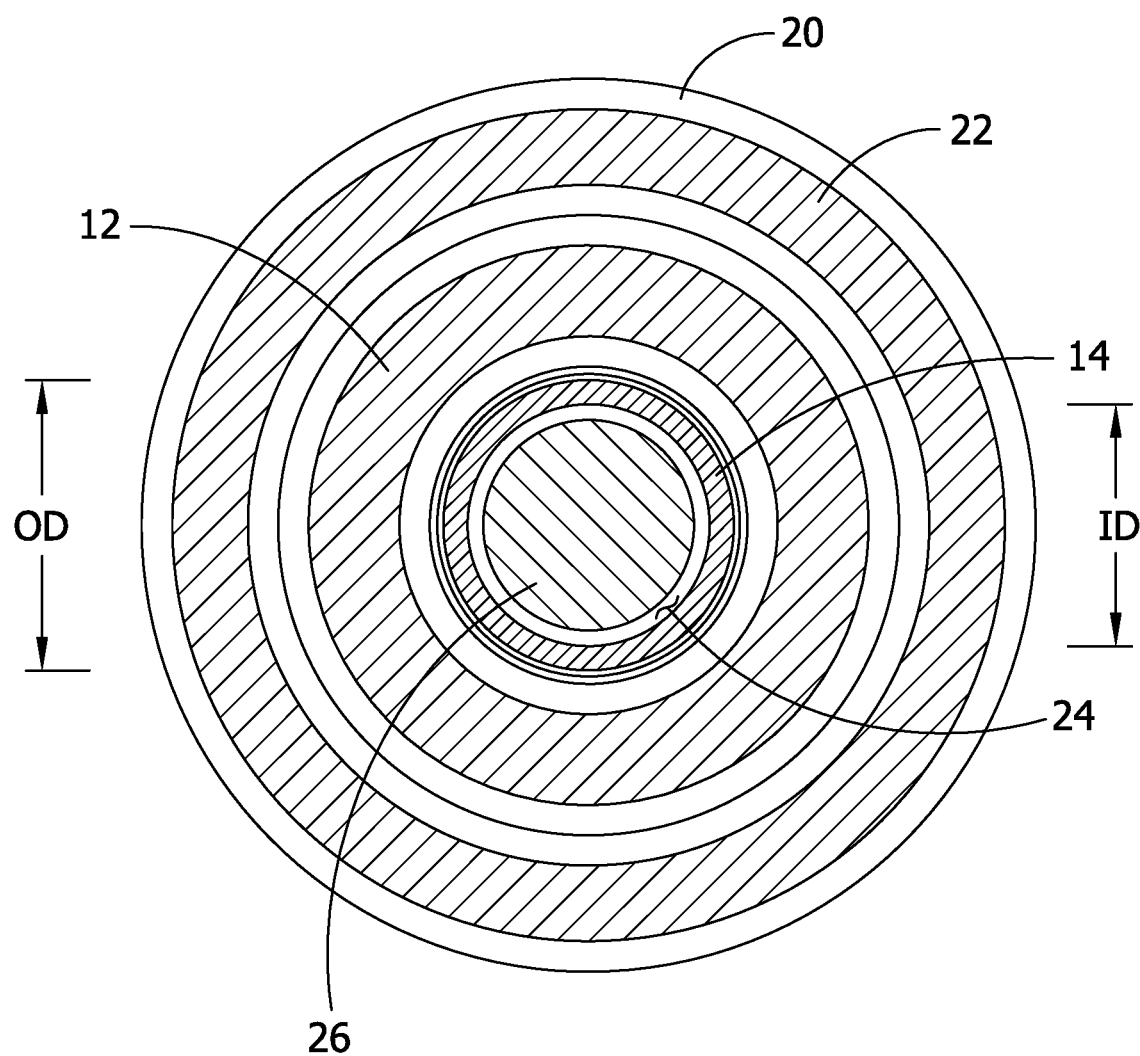
FIG. 27 is a cross section taken through line 27-27 in FIG. 2.
Figure 28:
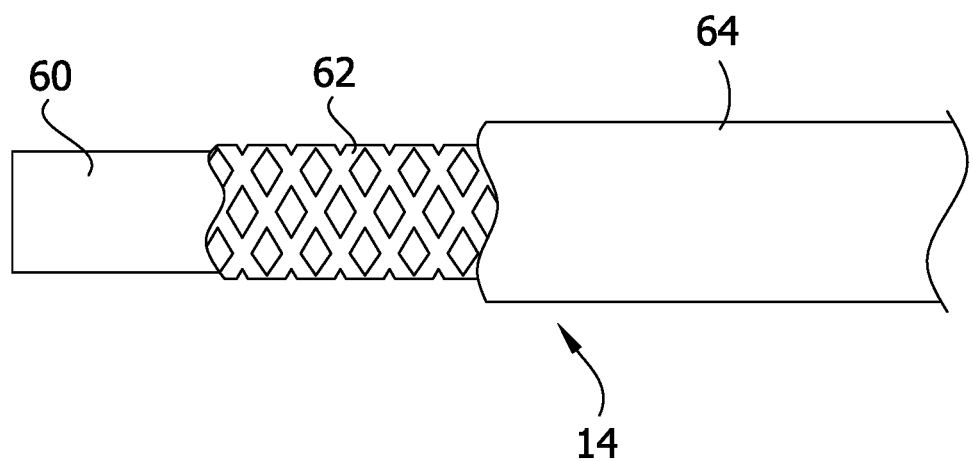
FIG. 28 is a fragmentary elevation of an isolation liner of the catheter with portions broken away to show internal details.
Figure 29:
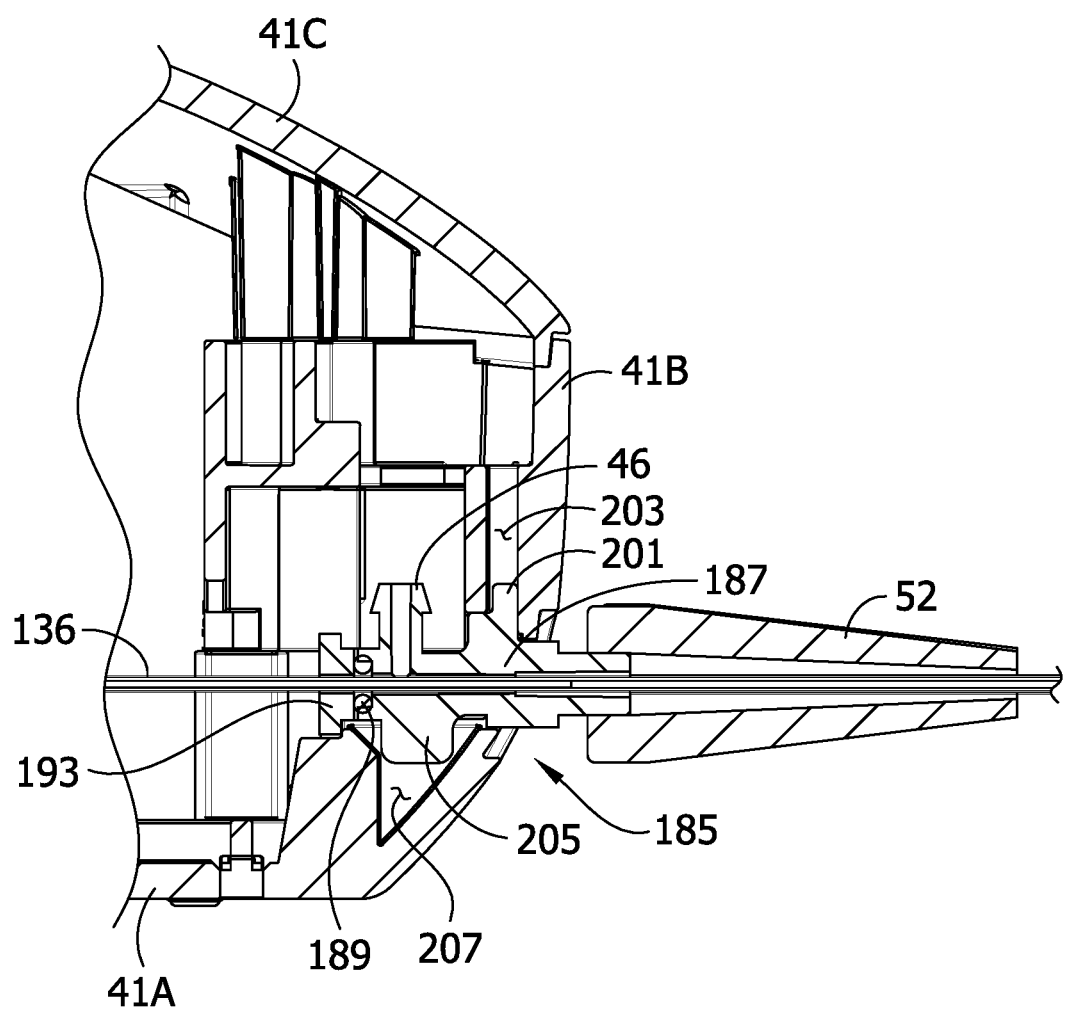
FIG. 29 is cross section of a distal end of the handle.
Figure 30:
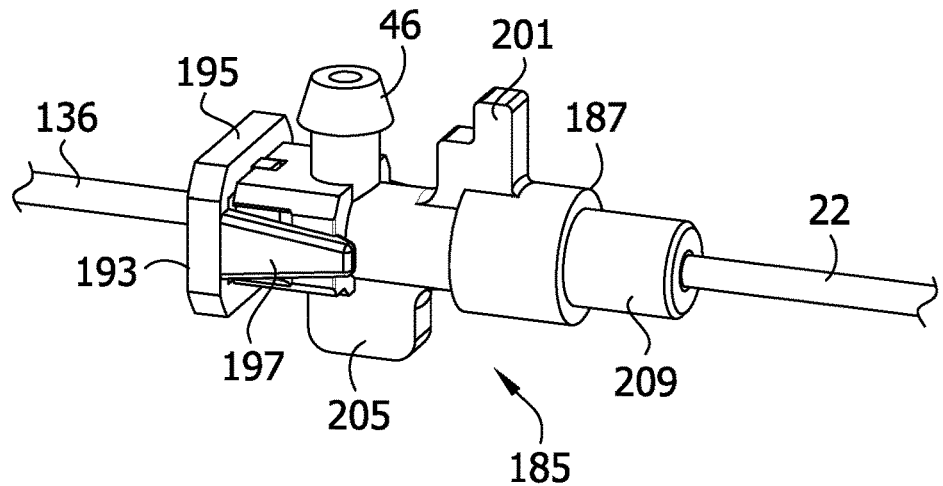
FIG. 30 is a perspective of an isolation sheath interface assembly in the handle.
Figure 31:
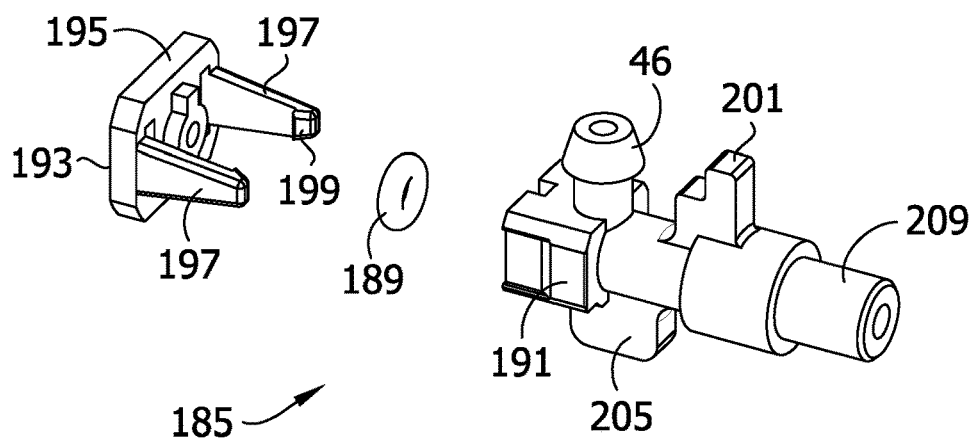
FIG. 31 is an exploded view of the isolation sheath interface assembly.
Figure 32:
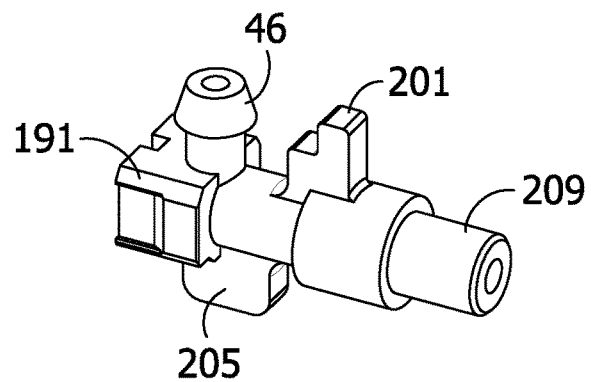
FIG. 32 is a perspective of an interface housing of the isolation sheath interface assembly.
Figure 33:
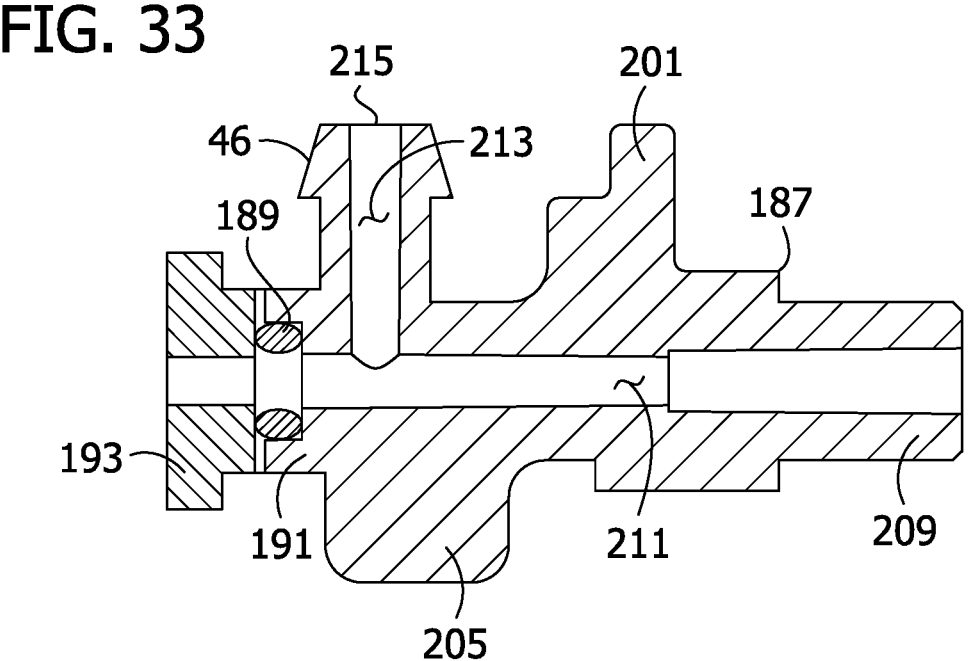
FIG. 33 is a cross section of the isolation sheath interface assembly showing a seal received in the interface housing.
Figure 34:
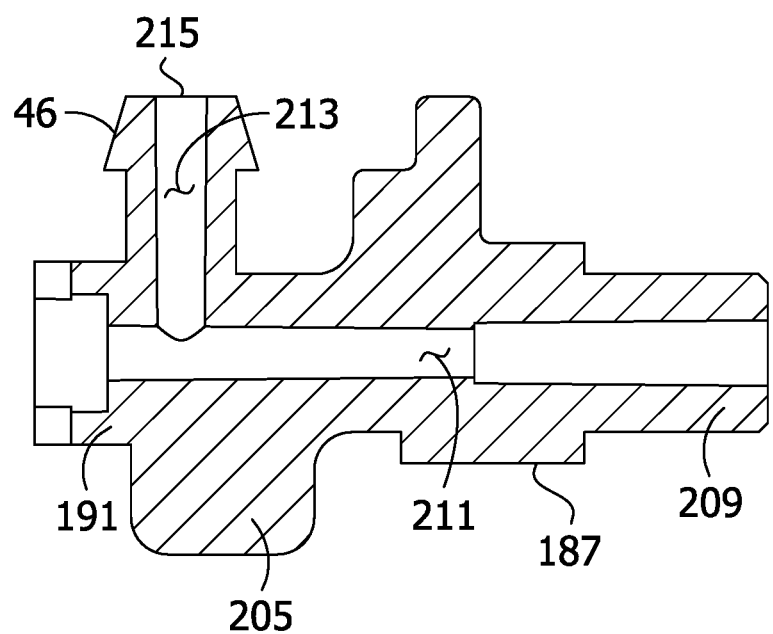
FIG. 34 is a cross section of the interface housing with the seal removed.
Figure 35:
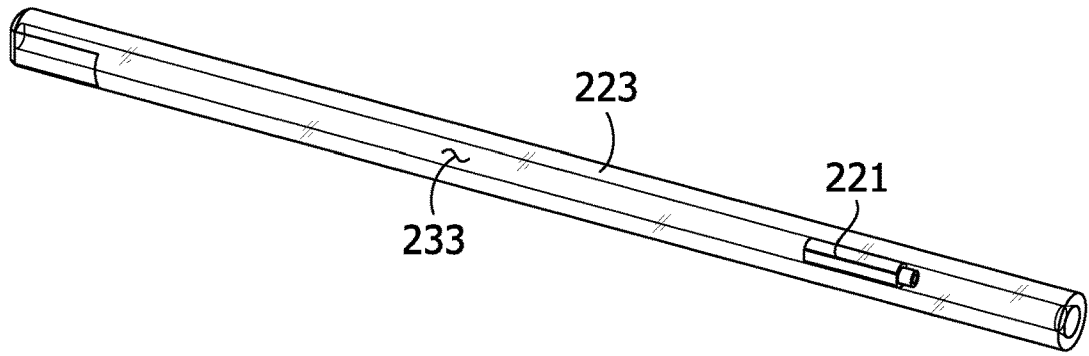
FIG. 35 is a perspective of an isolation liner interface assembly and liner assembly.
Figure 36:
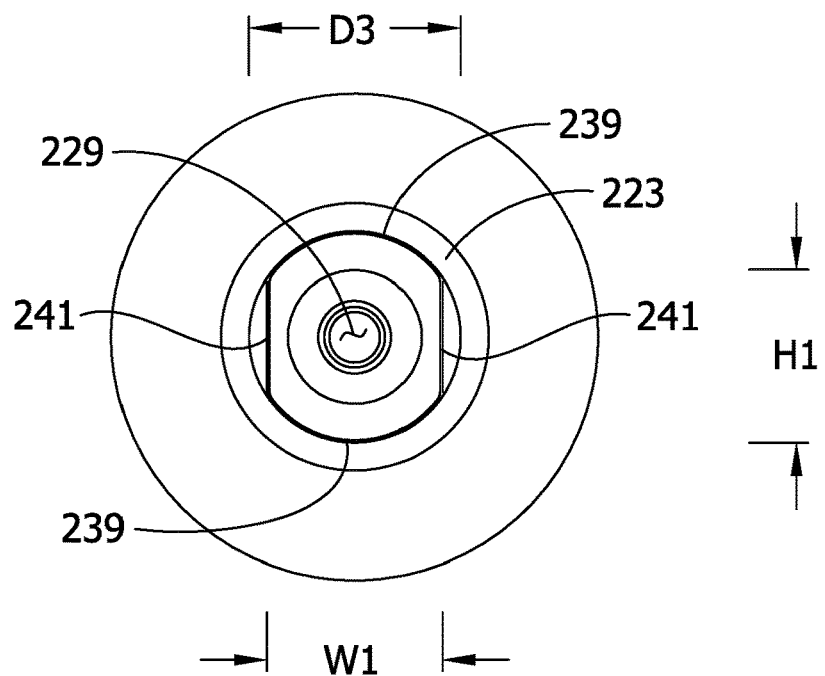
FIG. 36 is an end view of the isolation liner interface assembly and liner assembly.
Figure 37:
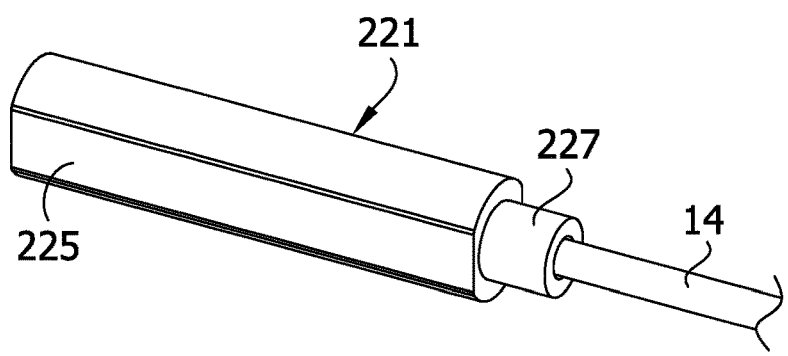
FIG. 37 is a fragmentary perspective of the liner assembly.
Figure 38:
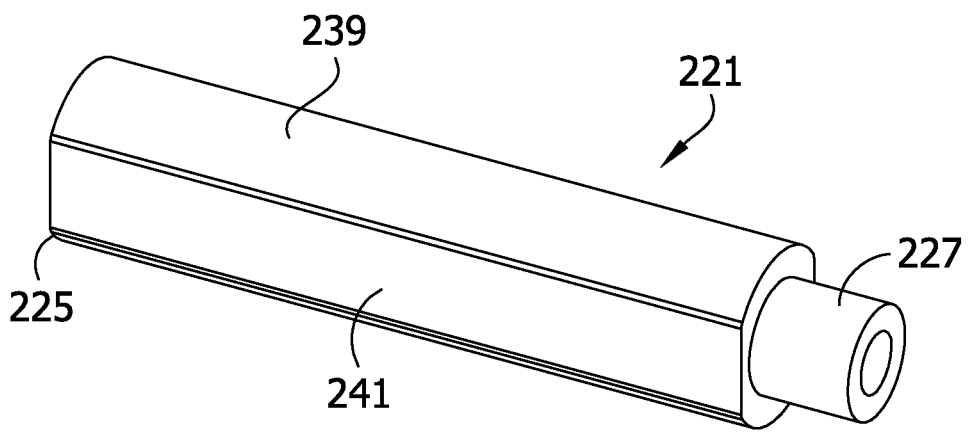
FIG. 38 is a perspective of a liner key of the liner assembly.
Figure 39:
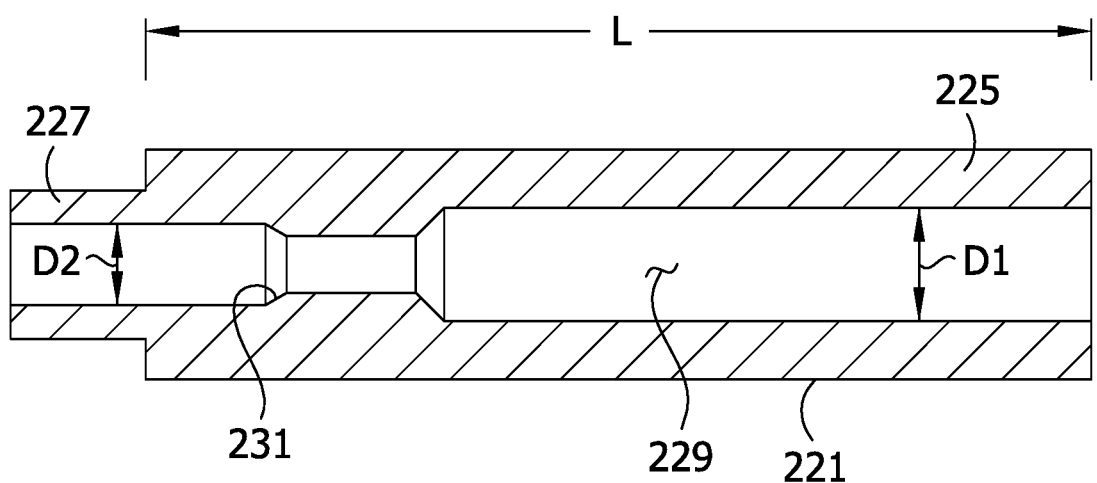
FIG. 39 is a cross section of the liner key.

Referring to FIGS. 1, and 27, the isolation sheath 22 comprises a tubular sleeve configured to isolate and protect a subject's arterial tissue within a body lumen from the rotating drive coil 12. The isolation sheath 22 is fixed to the handle 40 at a proximal end of the sheath and does not rotate. The isolation sheath interface assembly 185 attaches the sheath to the handle 40. The sheath 22 is received in the distal end portion 209 of the interface housing 187 to attach the sheath to the handle. The isolation sheath 22 provides a partial enclosure for the drive coil 12 and inner liner 14 to move within the sheath. The inner diameter of the isolation sheath 22 is sized to provide clearance for the drive coil 12. The space between the isolation sheath 22 and the drive coil 12 allows for the drive coil to rotate within the sheath and provides an area for saline perfusion between the sheath and drive coil. The outer diameter of the isolation sheath 22 is sized to provide clearance with an inner diameter of a guide catheter (not shown) for delivering the catheter 10 to the desired location in the body lumen. In one embodiment, the isolation sheath 22 has an inner diameter of about 0.050 inches (1.27 mm), an outer diameter of about 0.055 inches (1.4 mm), and a length of about 1500 mm (59 inches). The isolation sheath 22 can have other dimensions without departing from the scope of the disclosure. In one embodiment, the isolation sheath 22 is made from Polytetrafluorethylene (PTFE). Alternatively, the isolation sheath 22 may comprise a multi-layer construction. For example, the isolation sheath 22 may comprise an inner layer of perfluoroalkox (PFA), a middle braided wire layer, and an outer layer of Pebax.

Figure 26:
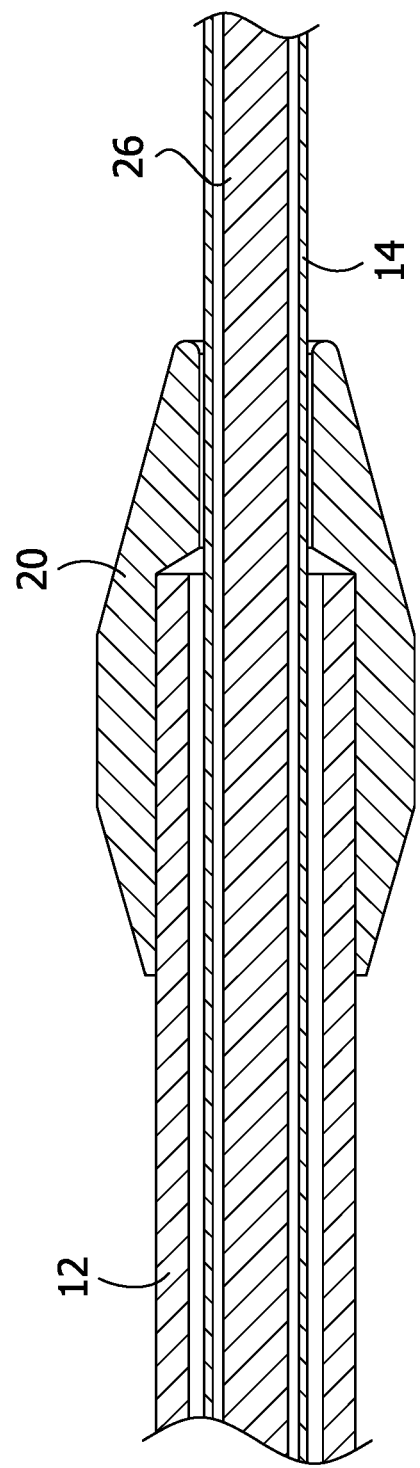
FIG. 26 is an enlarged fragmentary longitudinal cross section of the distal end portion of the catheter in FIG. 2.

Referring to FIGS. 1, 26, and 27, the drive coil 12 may comprise a tubular stainless steel coil configured to transfer rotation and torque from the motor 43 to the tissue-removing element 20. Configuring the drive coil 12 as a coiled structure provides the drive coil with a flexibility that facilitates delivery of the catheter 10 through the body lumen. In addition, the coil configuration allows for the rotation and torque of the drive coil 12 to be applied to the tissue-removing element 20 when the catheter 10 is traversed across a curved path. The stiffness of the drive coil 12 also impacts the ease at which the coil is traversed through the body lumen as well as the coil's ability to effectively transfer torque to the tissue-removing element 20. In one embodiment, the drive coil 12 is relatively stiff such that axial compression and extension of the coil is minimized during movement of the catheter 10 through a body lumen. The coil configuration of the drive coil 12 is also configured to expand its inner diameter when the coil is rotated so that the drive coil remains spaced from the inner liner 14 during operation of the catheter 10. In one embodiment, the drive coil 12 has an inner diameter of about 0.023 inches (0.6 mm) and an outer diameter of about 0.035 inches (0.9 mm). The drive coil 12 may have a single layer construction. For example, the drive coil may comprise a 7 filar (i.e., wire) coil with a lay angle of about 30 degrees. Alternatively, the drive coil 12 could be configured from multiple layers without departing from the scope of the disclosure. For example, the drive coil 12 may comprise a base coil layer and a jacket (e.g., Tecothane™) disposed over the base layer. In one embodiment, the drive coil comprises a 15 filar coil with a lay angle of about 45 degrees. The Tecothane™ jacket may be disposed over the coil. Alternatively, the drive coil 12 may comprise a dual coil layer configuration which also includes an additional jacket layer over the two coil layers. For example, the drive coil may comprise an inner coil layer comprising a 15 filar coil with a lay angle of about 45 degrees, and an outer coil layer comprising a 19 filar coil with a lay angle of about 10 degrees. Drive coils having other configurations are also envisioned.

Referring to FIGS. 1 and 26-28, the inner liner 14 comprises a multiple layer tubular body configured to isolate the guidewire 26 from the drive coil 12 and tissue-removing element 20. The inner liner 14 is extendable through the handle 40 from a position within the handle to a position distal of the handle. In one embodiment, the inner liner 14 is coupled to the components within the handle 40 but is not fixedly attached to the housing 41 to allow translation of the inner liner relative to the housing. The inner liner 14 has an inner diameter that is sized to pass the guidewire 26. The inner liner 14 protects the guide wire from being damaged by the rotation of the drive coil 12 by isolating the guidewire from the rotatable drive coil. The inner liner 14 may also extend past the tissue-removing element 20 to protect the guidewire 26 from the rotating tissue-removing element. Thus, the inner liner 14 is configured to prevent any contact between the guidewire 26 and the rotating components of the catheter 10. Therefore, any metal-to-metal engagement is eliminated by the inner liner 14. This isolation of the drive coil 12 and tissue-removing element 20 from the guidewire 26 also ensures that the rotation of the drive coil and tissue-removing element is not transferred or transmitted to the guidewire. As a result, a standard guidewire 26 can be used with the catheter 10 because the guidewire does not have to be configured to withstand the torsional effects of the rotating components. Additionally, by extending through the tissue-removing element 20 and past the distal end of the tissue-removing element, the inner liner 14 stabilizes the tissue-removing element by providing a centering axis for rotation of the tissue-removing element about the inner liner.

In the illustrated embodiment, the inner liner 14 comprises an inner PTFE layer 60 an intermediate braided layer 62 comprised of stainless steel, and an outer layer 64 of polyimide. The PTFE inner layer 60 provides the inner liner 14 with a lubricous interior which aids in the passing of the guidewire 26 though the inner liner. The braided stainless steel intermediate layer 62 provides rigidity and strength to the inner liner 14 so that the liner can withstand the torsional forces exerted on the inner liner by the drive coil 12. In one embodiment, the intermediate layer 62 is formed from 304 stainless steel. The outer polyimide layer 64 provides wear resistance as well as having a lubricous quality which reduces friction between the inner liner 14 and the drive coil 12. Additionally, a lubricious film, such as silicone, can be added to the inner liner 14 to reduce friction between the inner liner and the drive coil 12. In one embodiment, the inner liner 14 has an inner diameter ID of about 0.016 inches (0.4 mm), an outer diameter OD of about 0.019 inches (0.5 mm), and a length of about 59 inches (1500 mm). The inner diameter ID of the inner liner 14 provides clearance for the standard 0.014-inch guidewire 26. The outer diameter OD of the inner liner 14 provides clearance for the drive coil 12 and tissue-removing element 20. Having a space between the inner liner 14 and the drive coil 12 reduces friction between the two components as well as allows for saline perfusion between the components.

Referring to FIGS. 35-39, a liner key 221 is attached to a proximal end of the liner 14 and is received in a guide tube 223 fixedly mounted in the handle 40. The liner 14 and liner key 221 may be broadly a liner assembly 224. The engagement between the liner key 221 and the guide tube 223 permits the liner key and liner 14 to translate relative to the guide tube but prevents rotation of the liner key and liner relative to the guide tube. The liner key 221 comprises a semi-cylindrical member 225 and an elongate tubular member 227 extending distally from a distal end of the semi-cylindrical member. A channel 229 extends through the liner key 221. The channel 229 forms an inner diameter $D_1$ in the semi-cylindrical member of about 0.8 mm and an inner diameter $D_2$ in the tubular member of about 0.55 mm. In one embodiment, the semi-cylindrical member 225 has a length L of between about 6 mm and about 8 mm. In one embodiment, the semi-cylindrical member 225 has a length L of about 7 mm. The proximal end of the liner 14 is received and retained in the section of the channel 229 in the elongate tubular member 227. The liner 14 can be retained in the liner key 221 by any suitable means, including without limitation, glue, thermal bond, and mechanical bond. The proximal end of the liner 14 seats against a floor 231 in the liner key 221 to locate the liner in the liner key. Thus, the liner key 221 and the liner 14 co-translate with each other. In the illustrated embodiment, the guide tube 223 has a circular passage 223. Alternatively, the guide tube 223 may have a non-circular interior passage defined by top and bottom curved wall sections and a pair of side planar wall sections extending between the top and bottom wall sections.

The semi-cylindrical member 225 comprises a pair of top and bottom curved surfaces 239 and a pair of opposing flat surfaces 241 so that the dimensions of the guide tube and liner key 221 prevent relative rotation. In one embodiment, a width $W_1$ extending between the flat surfaces 241 of the semi-cylindrical member 225 is about 1.4 mm, and height $H_1$ extending between the top and bottom curved surfaces 239 is about 1.7 mm. In one embodiment, a dimeter $D_3$ of the interior passage of the guide tube 223 is about 1.74 mm. Alternatively, in the embodiment where the guide tube includes side planar wall sections, a width of the interior passage 233 of the guide tube 223 may be about 1.5 mm, and a height may be about 1.74 mm. Thus, the interior passage 233 provides sufficient clearance to receive the liner key 221 for axial movement but does not allow rotational movement of the liner key in the guide tube. The configuration of the liner key 221 and guide tube 223 also reduces the friction on the liner 14 during advancement and retraction of the liner. In one embodiment, axial translation of at least about 70 mm is permitted. The liner key 221 configuration also facilitates assembly of the handle 40 by allowing the key to be inserted though the gearbox housing 55.

It is envisioned that the liner key 221 and guide tube 223 can have over configurations for permitting relative translation and preventing relative rotation. For instance, the liner key 221 can be generally rectangular and the guide tube 223 may have a mating rectangular interior passage. Still other configurations are envisioned within the scope of the disclosure. Further, any suitable materials may be used for the liner key 221 and guide tube 223. For example, the liner key 221, can be formed from Peek, Polyoxymethylene (POM), or polycarbonate (PC). The inner liner 14 and liner key 221 may be broadly considered a liner key assembly.

Figure 7:
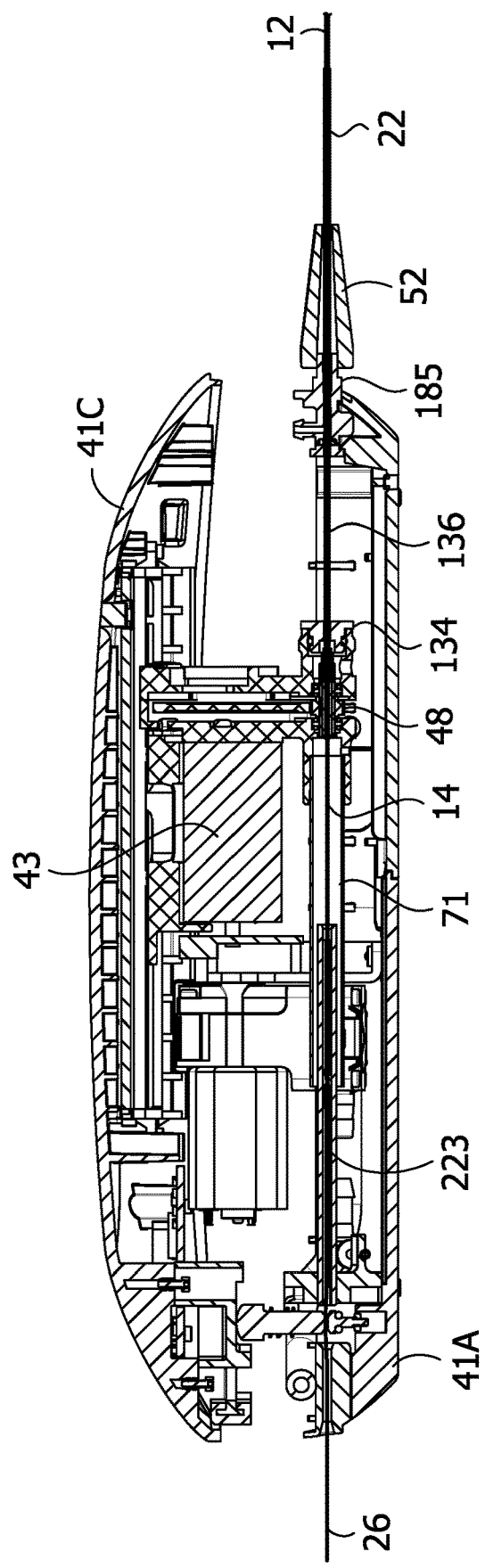
FIG. 7 is a side view of the handle with a middle housing section removed and top and bottom housing sections shown as transparent.
Figure 8:
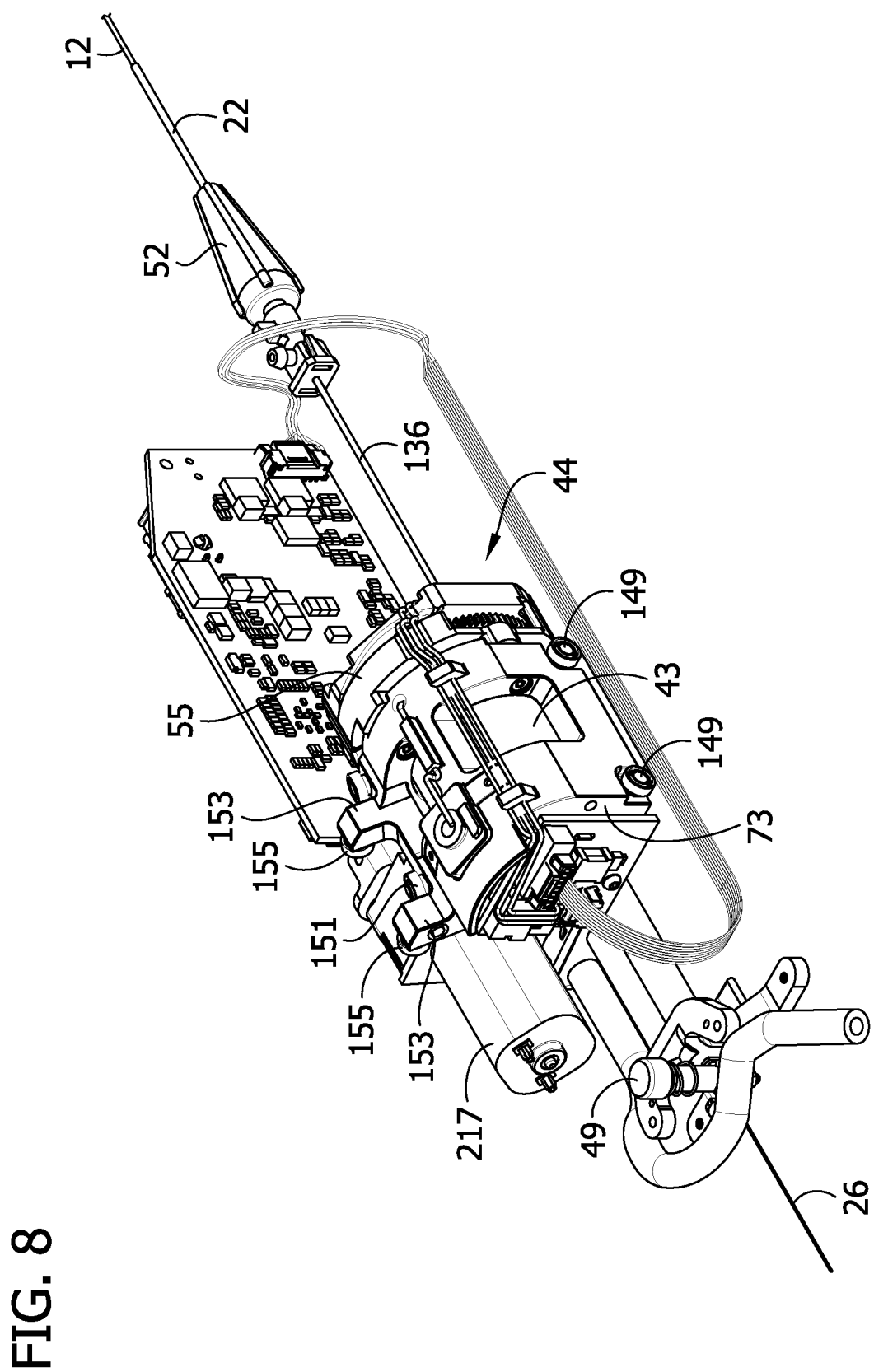
FIG. 8 is a perspective of the handle with the housing sections and some internal components removed.
Figure 9A:
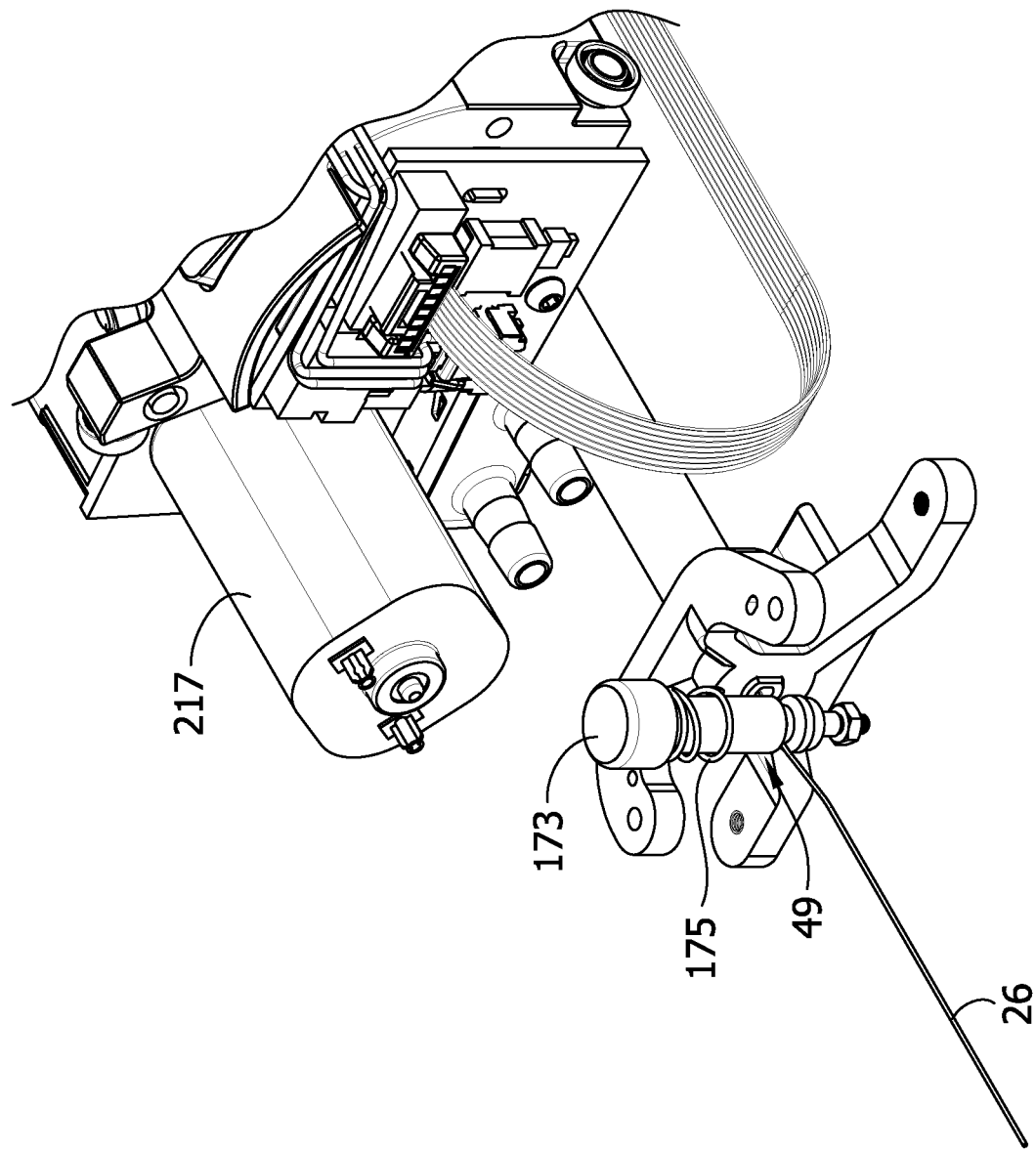
FIG. 9A is an enlarged fragmentary top perspective of the handle with the housing sections and some internal components removed.
Figure 9B:
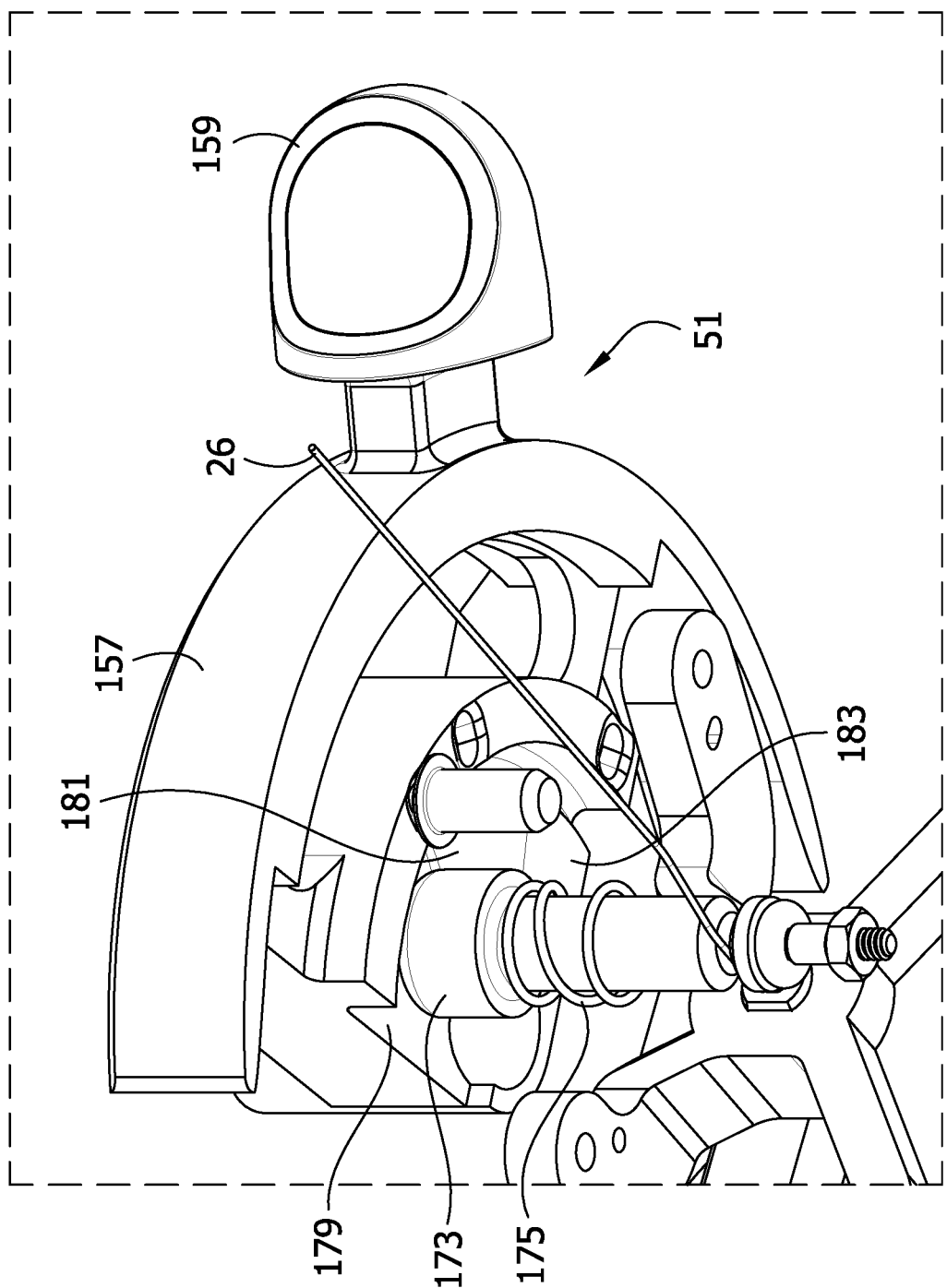
FIG. 9B is an enlarged fragmentary bottom perspective of the handle with the housing sections and some internal components removed.
Figure 10A:
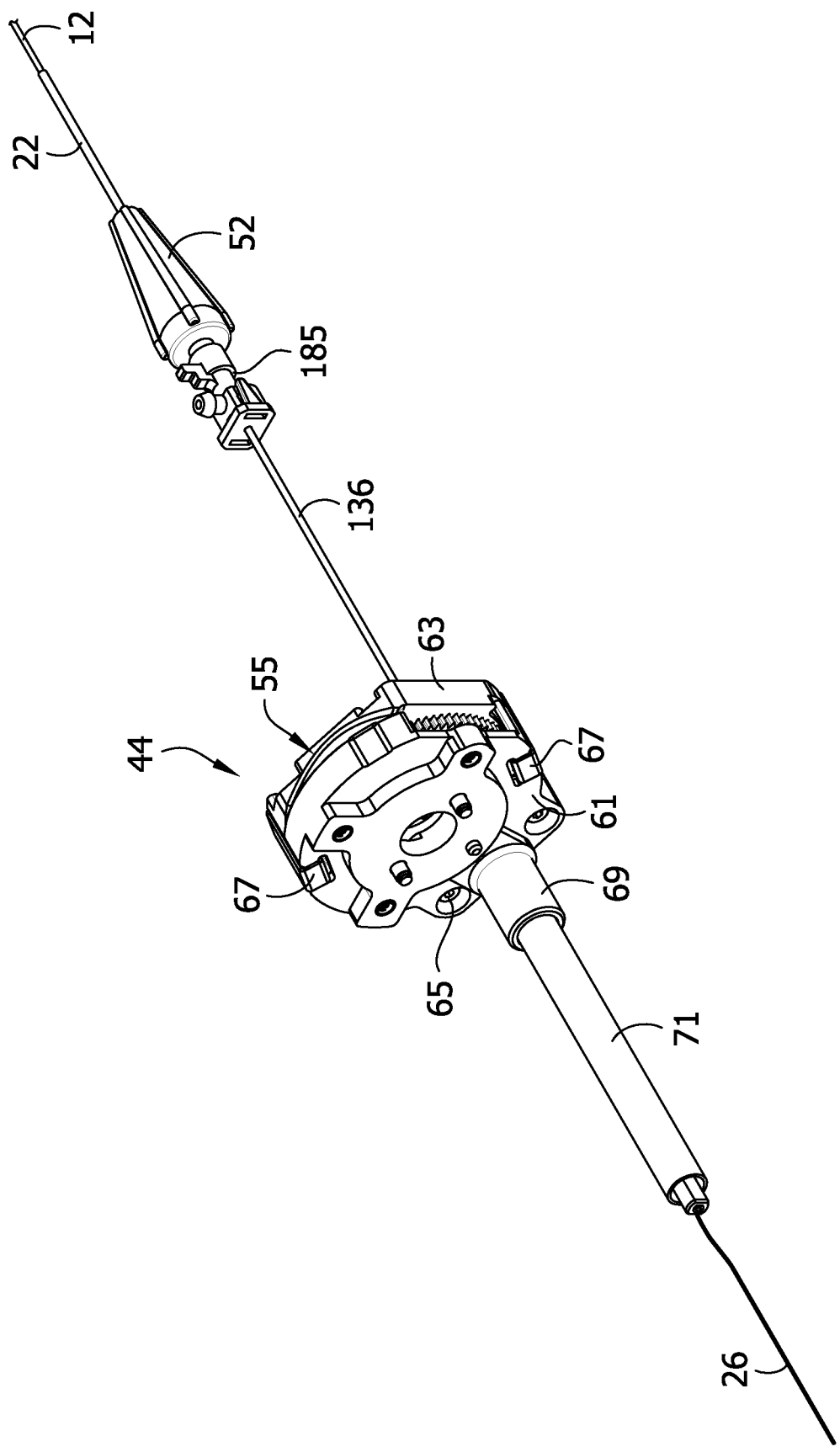
FIG. 10A is a rear perspective of components of the catheter and internal components of the handle.
Figure 10B:
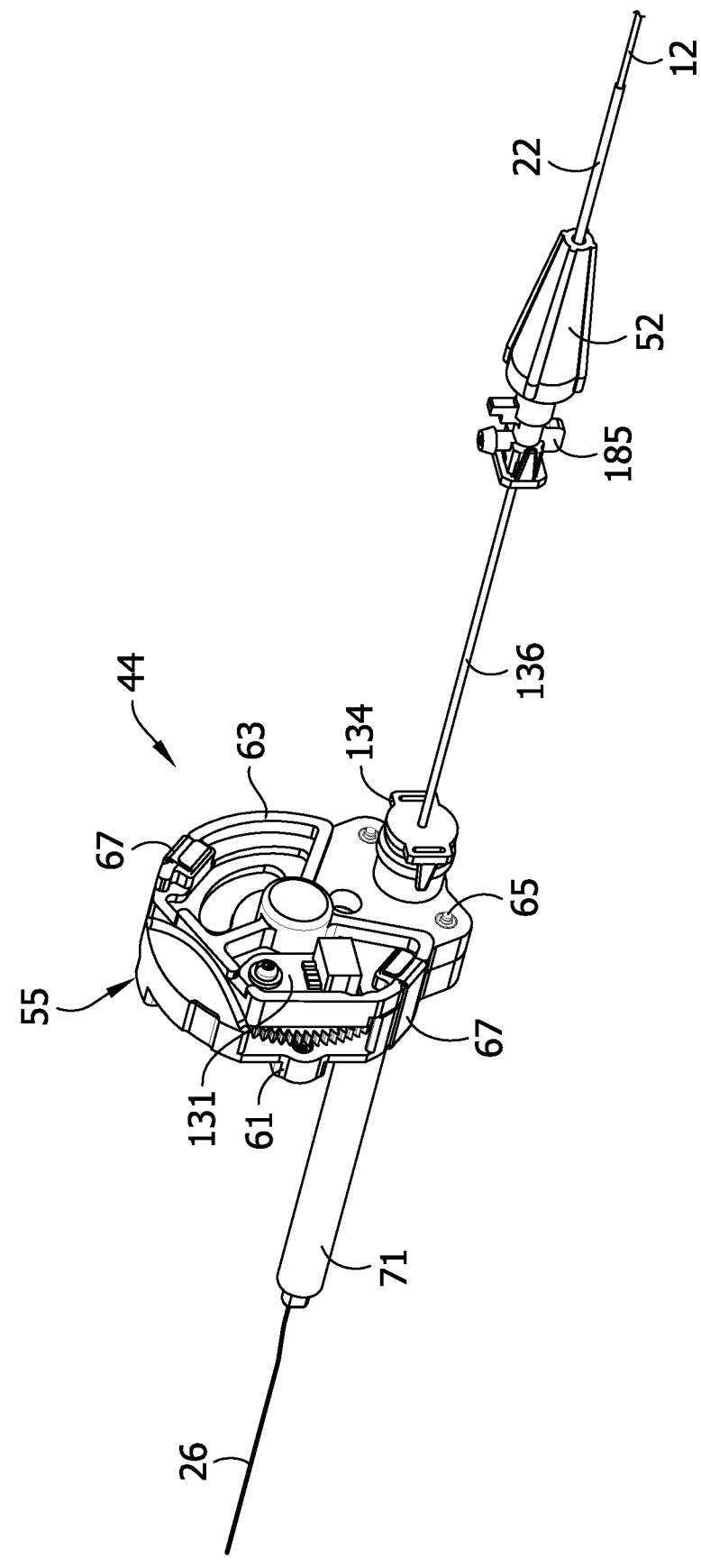
FIG. 10B is a front perspective of components in FIG. 10A.
Figure 11:
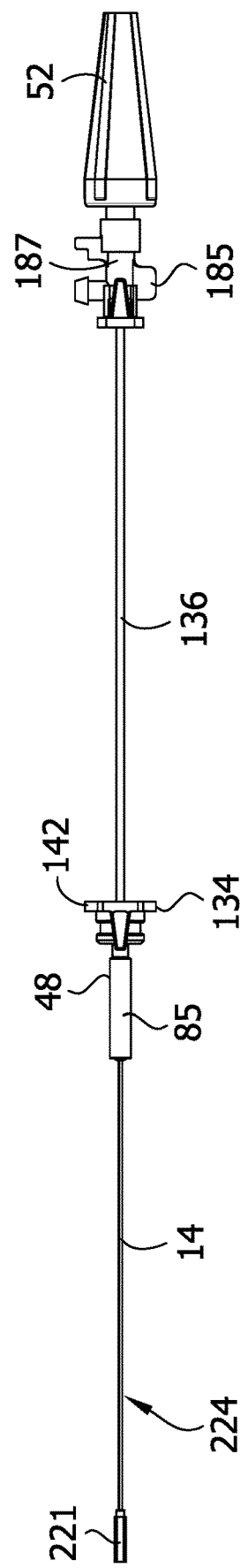
FIG. 11 is a side view of components of the catheter and internal components of the handle.
Figure 12:
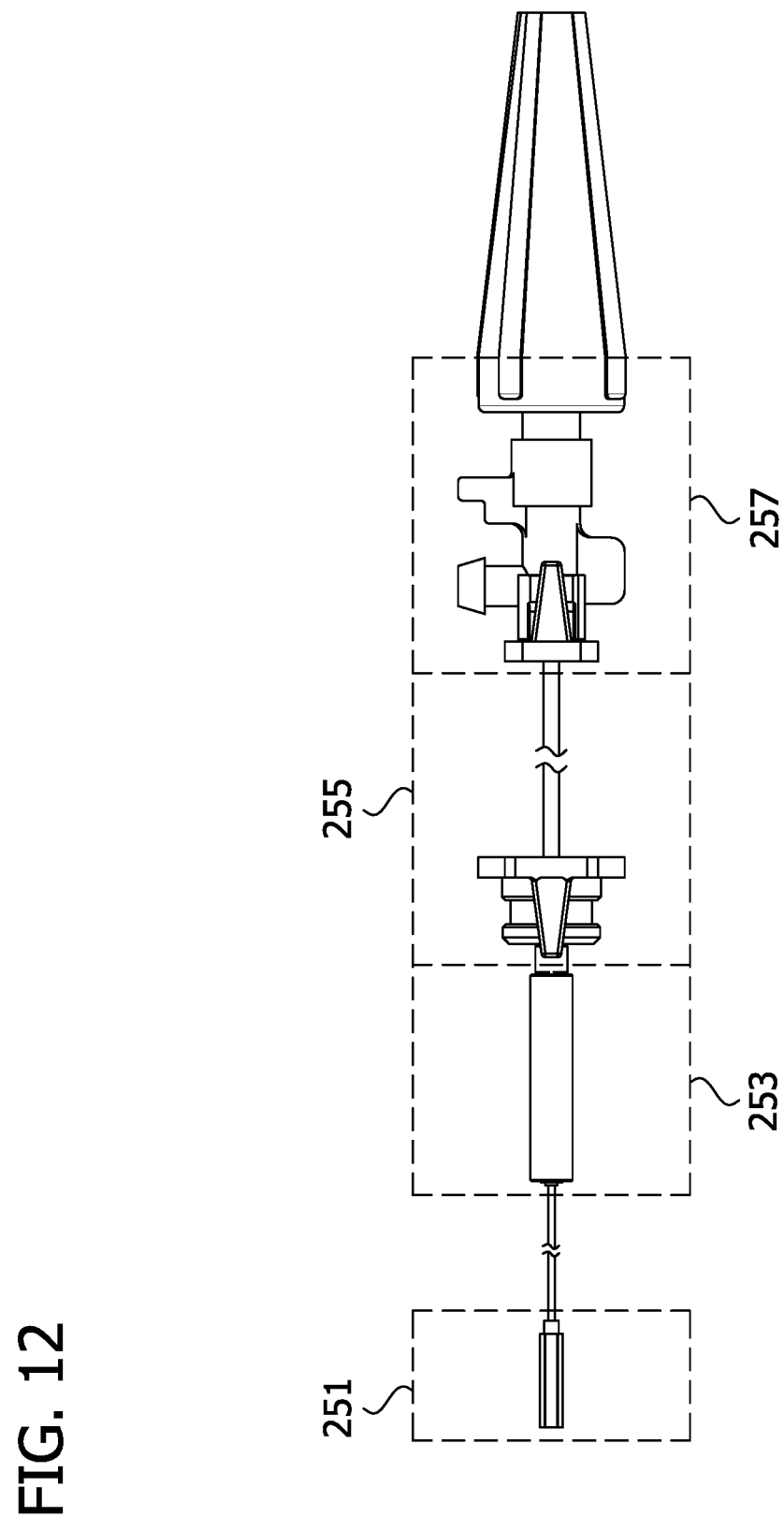
FIG. 12 is another side view of components of the catheter and internal components of the handle.
Figure 13:
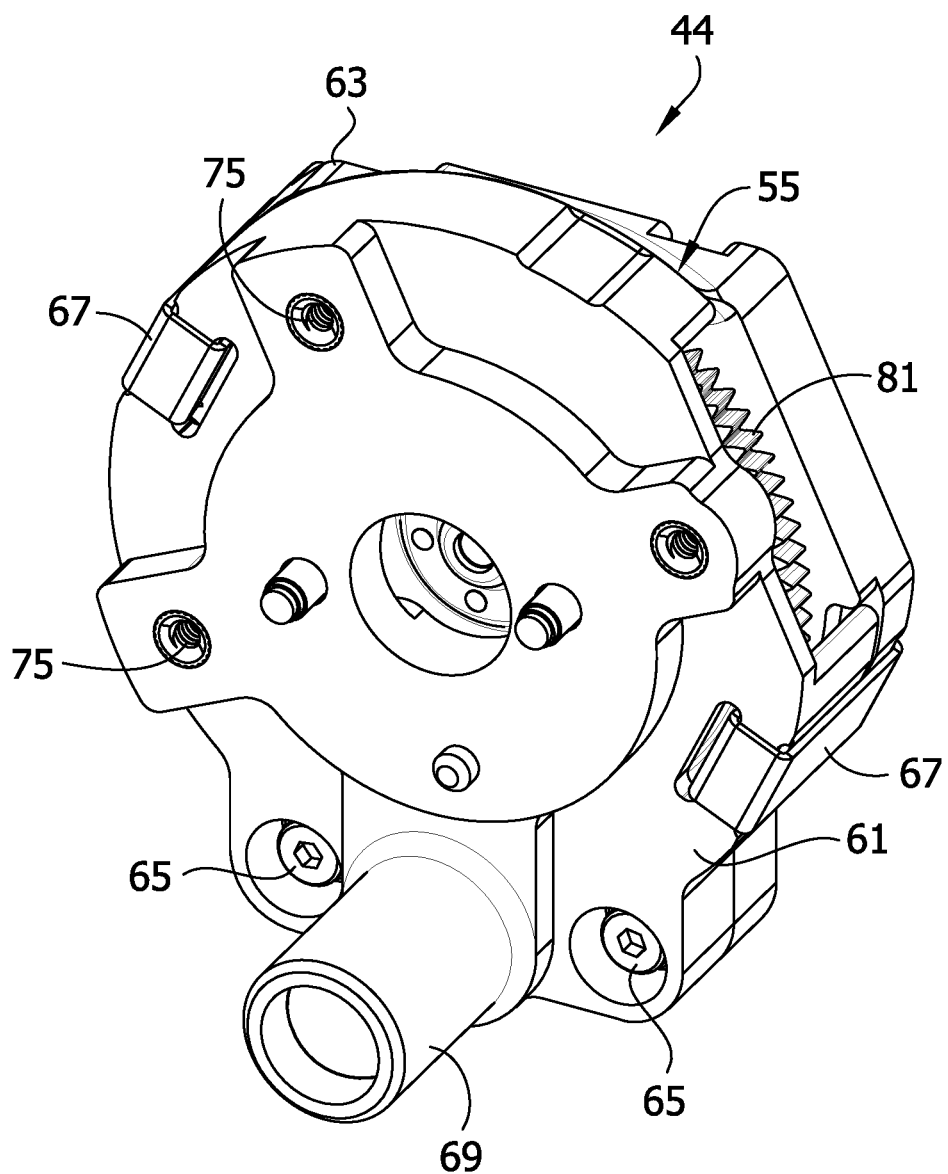
FIG. 13 is a rear perspective of a gear assembly in the handle.

Referring to FIGS. 7, 11, and 12, the handle 40 provides four locations of contact or interface between the internal components of the handle and the longitudinally extending catheter components (broadly, catheter body assembly) that extend through the handle. A first interface 251 occurs between the liner assembly 224 and the guide tube 223. A second interface 253 occurs between the drive coil 12 and the drive assembly 48. A third interface 255 occurs between the drive coil and the travel sheath interface assembly 134. A fourth interface 257 occurs between the isolation sheath 22 and the isolation sheath interface assembly 185. It will be understood that the internal components of the handle 40 may interface with the catheter body assembly at other location.

The interfaces 251, 253, 255, 257 are axially aligned along the longitudinal extension of the catheter components. The interfaces 251, 253, 255, 257 provide alignment and stability to the catheter body assembly as it passes through the handle 40. In particular, the first interface 251 between the liner key assembly 224 and the guide tube 223 aligns and stabilizes the liner 14. This helps to prevent buckling of the liner 14 during movement of the liner 14 in the handle 40. As a result, the extension of the liner 14 is maintained along a linear axis. Further, the second interface 253 stabilizes the drive coil 12 within the housing 40. Thus, the extension of the drive coil 12 during rotation of the drive coil is maintained about a linear axis that is generally parallel to and coincident with the axis of extension of the liner 14. Therefore, the spacing between the drive coil 12 and liner 14 are maintained throughout operation of the catheter 10 so that the liner appropriately shields the guidewire 26 from the rotating drive coil 12. The third interface 255 stabilizes and holds the drive coil 12 in alignment throughout the extension of the drive coil through the travel sheath interface assembly 134. Therefore, the linear extension of the drive coil is maintained along the distal portion of the handle 40. The fourth interface 257 functions to stabilize the drive coil 12 as well as the isolation sheath 22 to maintain alignment of the drive coil with the inner liner 14 during rotation.

Referring to FIGS. 1, 2, and 26, the tissue-removing element 20 extends along the longitudinal axis LA from a proximal end adjacent the distal end portion of the drive coil 12 to an opposite distal end. The tissue-removing element 20 is operatively connected to the motor 43 for being rotated by the motor. When the catheter 10 is inserted into the body lumen and the motor 43 is rotating the tissue-removing element 20, for example in the abrade mode, the tissue-removing element is configured to remove occlusive tissue in the body lumen to separate the tissue from the wall of the body lumen. Any suitable tissue-removing element for removing tissue in the body lumen as it is rotated may be used in one or more embodiments. In one embodiment, the tissue-removing element 20 comprises an abrasive burr configured to abrade tissue in the body lumen when the motor 43 rotates the abrasive burr. The abrasive burr 20 may have an abrasive outer surface formed, for example, by a diamond grit coating, surface etching, or the like. In one embodiment, the tissue-removing element comprises a stainless steel spheroid body with an exterior surface including 5 μm of exposed diamond crystals. The tissue-removing element 20 may also be radiopaque to allow the tissue-removing element to be visible under fluoroscopy. In other embodiments, the tissue-removing element can comprise one or more cutting elements having smooth or serrated cutting edges, a macerator, a thrombectomy wire, etc.

Referring to FIGS. 1 and 2, to remove tissue in the body lumen of a subject, a practitioner inserts the guidewire 26 into the body lumen of the subject, to a location distal of the tissue that is to be removed. Subsequently, the practitioner inserts the proximal end portion of the guidewire 26 through the guidewire lumen 24 of the inner liner 14 and through the handle 40 so that the guidewire extends through the proximal port 47 in the handle. With the catheter 10 loaded onto the guidewire 26, the practitioner advances the catheter along the guidewire until the tissue-removing element 20 is positioned proximal and adjacent the tissue. Initially, the catheter 10 may be placed in the "standby" mode through actuation of the mode selector 51. In this mode, the motor 43 is deactivated and the guide wire 26 is unlocked so that the catheter 10 can be moved relative to the guidewire. As the catheter 10 is being traversed through the body, the mode selector 51 can be moved to the "track mode" where the motor 43 is activated to produce the first output and the guidewire 26 is kept unlocked. The slow rotation of the tissue-removing element 20 at the first output of the motor 43 may be advantage in navigating the catheter 10 through tortuous pathways. When the tissue-removing element 20 is positioned proximal and adjacent the tissue, the mode selector 51 can be operated to place the catheter 10 in the "abrade mode" to operate the motor 43 at the second output to rotate the drive coil 12 and the tissue-removing element mounted on the drive coil at a higher rate for use in abrading (or otherwise removing) the tissue in the body lumen. This will also lock the guidewire 26 in place. While the tissue-removing element 20 is rotating, the practitioner may selectively move the drive coil 12 distally along the guidewire 26 to abrade the tissue and, for example, increase the size of the passage through the body lumen. The practitioner may also move the drive coil 12 proximally along the guidewire 26, and may repetitively move the component in distal and proximal directions to obtain a back-and-forth motion of the tissue-removing element 20 across the tissue. During the abrading process, the inner liner 14 isolates the guidewire 26 from the rotating drive coil 12 and tissue-removing element 20 to protect the guidewire from being damaged by the rotating components. As such, the inner liner 14 is configured to withstand the torsional and frictional effects of the rotating drive coil 12 and tissue-removing element 20 without transferring those effects to the guidewire 26. When the practitioner is finished using the catheter 10, the catheter can be withdrawn from the body lumen and unloaded from the guidewire 26 by sliding the catheter proximally along the guidewire. The guidewire 26 used for the abrading process may remain in the body lumen for use in a subsequent procedure.

Referring to FIGS. 40-74, a handle of another embodiment is generally indicated at 40'. The handle 40' is similar to the handle 40 of the previous embodiment and operates generally in the same manner as handle 40. For example, the handle 40' also provides four points of contact or interface between the internal components of the handle and the longitudinally extending catheter body assembly 10 that extends through the handle. Thus, the handle 40' provides alignment and stability to the catheter body assembly 10 as it passes through the handle 40. However, the specific configuration of the internal components of the housing 40' differ from the internal components of housing in some respects. The details of the internal components of the housing 40' are discussed below.

Figure 40:
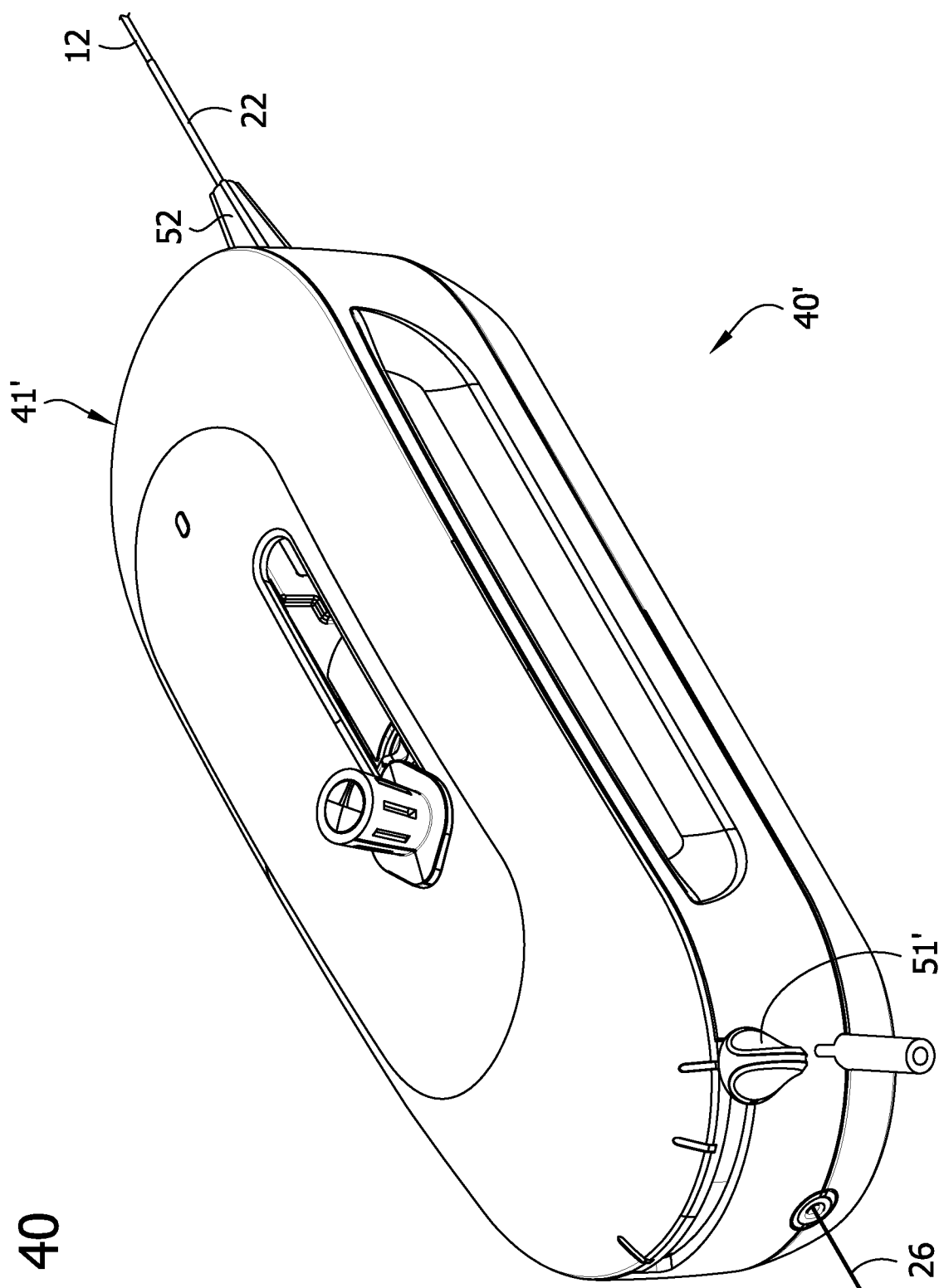
FIG. 40 is a top perspective of a handle of another embodiment.
Figure 41:
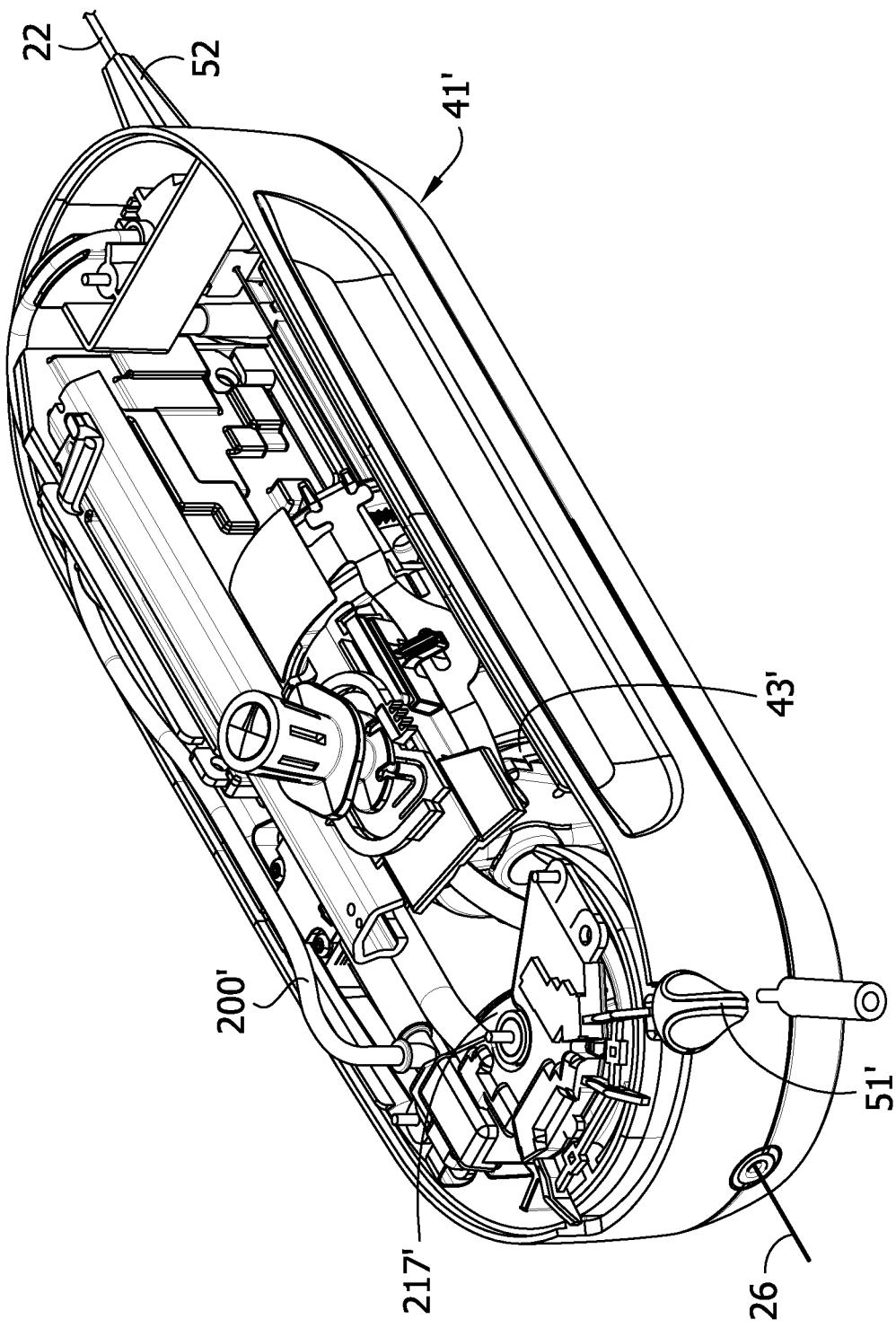
FIG. 41 is a top perspective of the handle of FIG. 40 with a top housing section removed.
Figure 42:
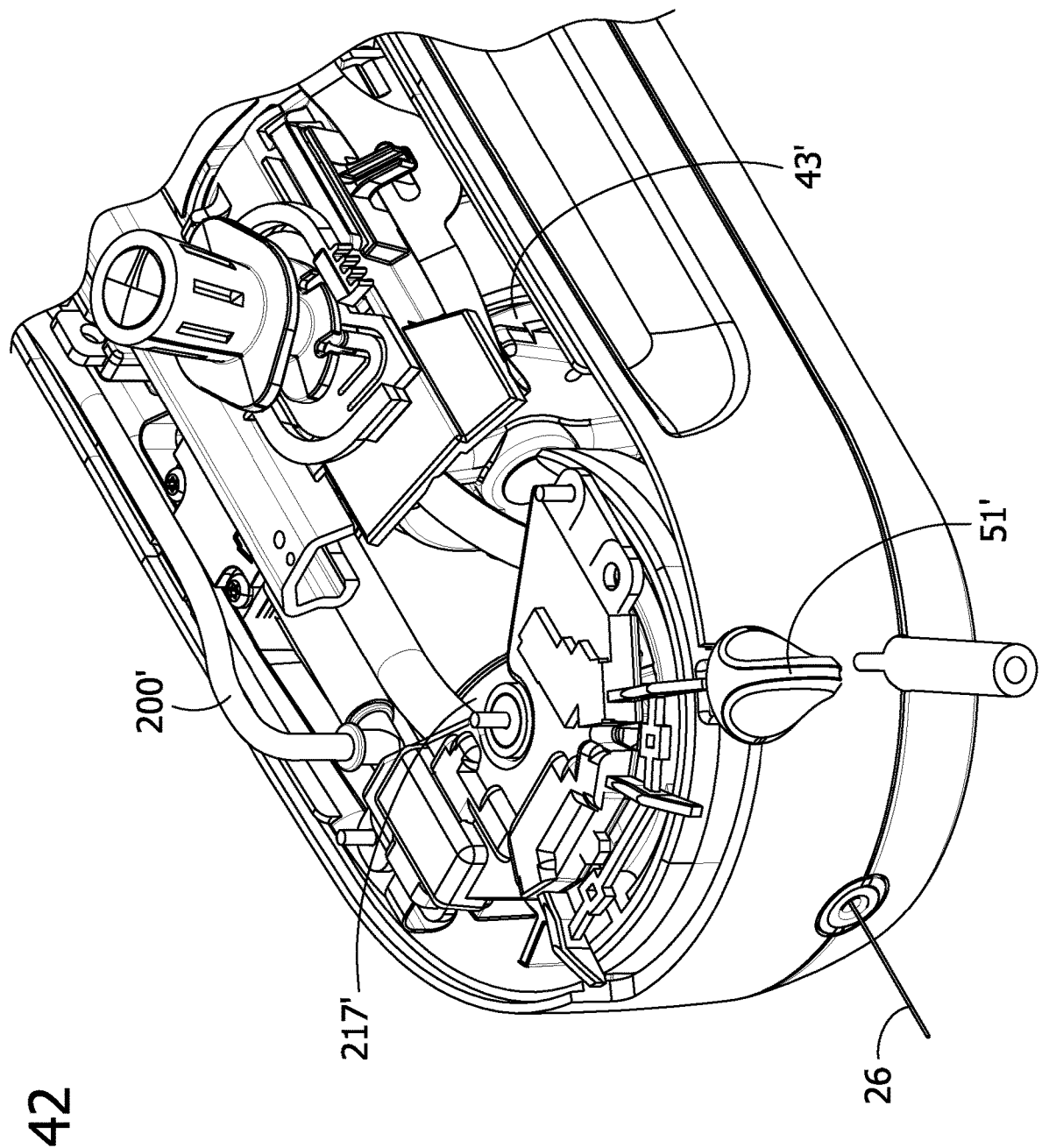
FIG. 42 is fragmentary perspective of the handle of FIG. 41.
Figure 43:
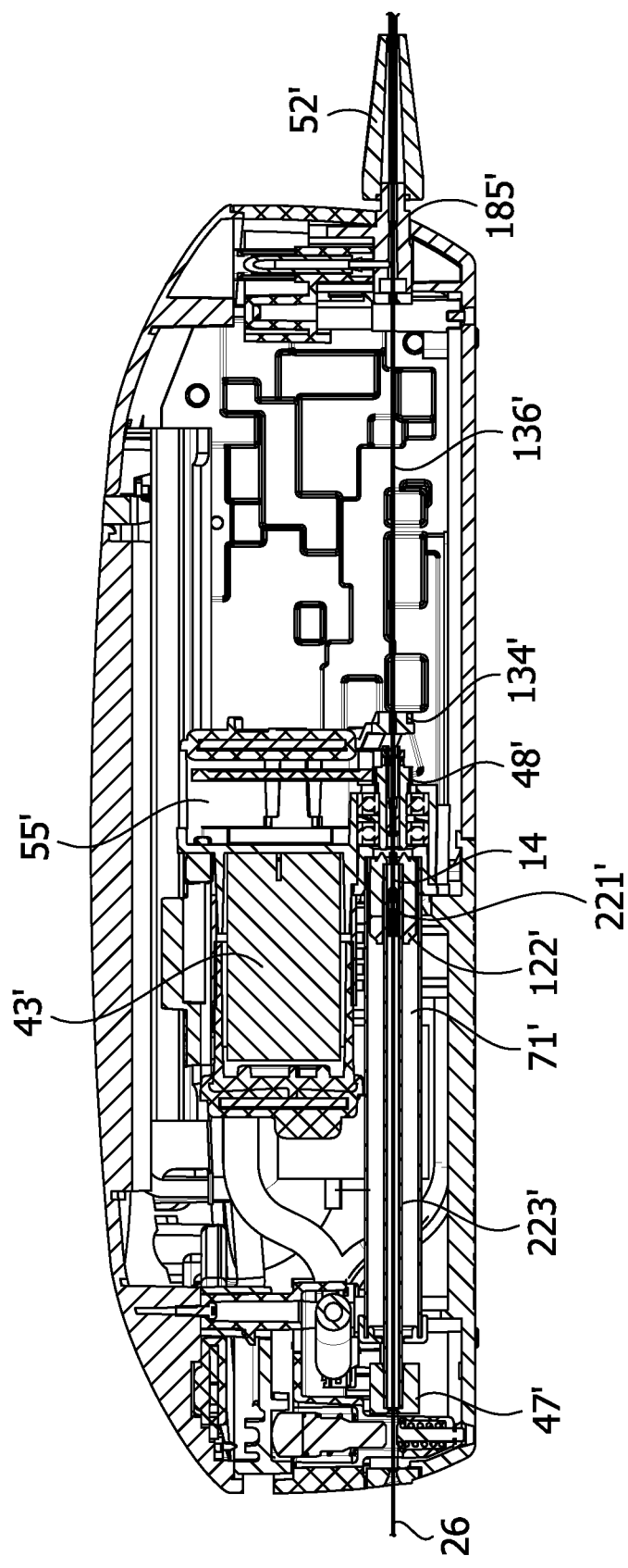
FIG. 43 is a cross section of the handle of FIG. 40.
Figure 44:
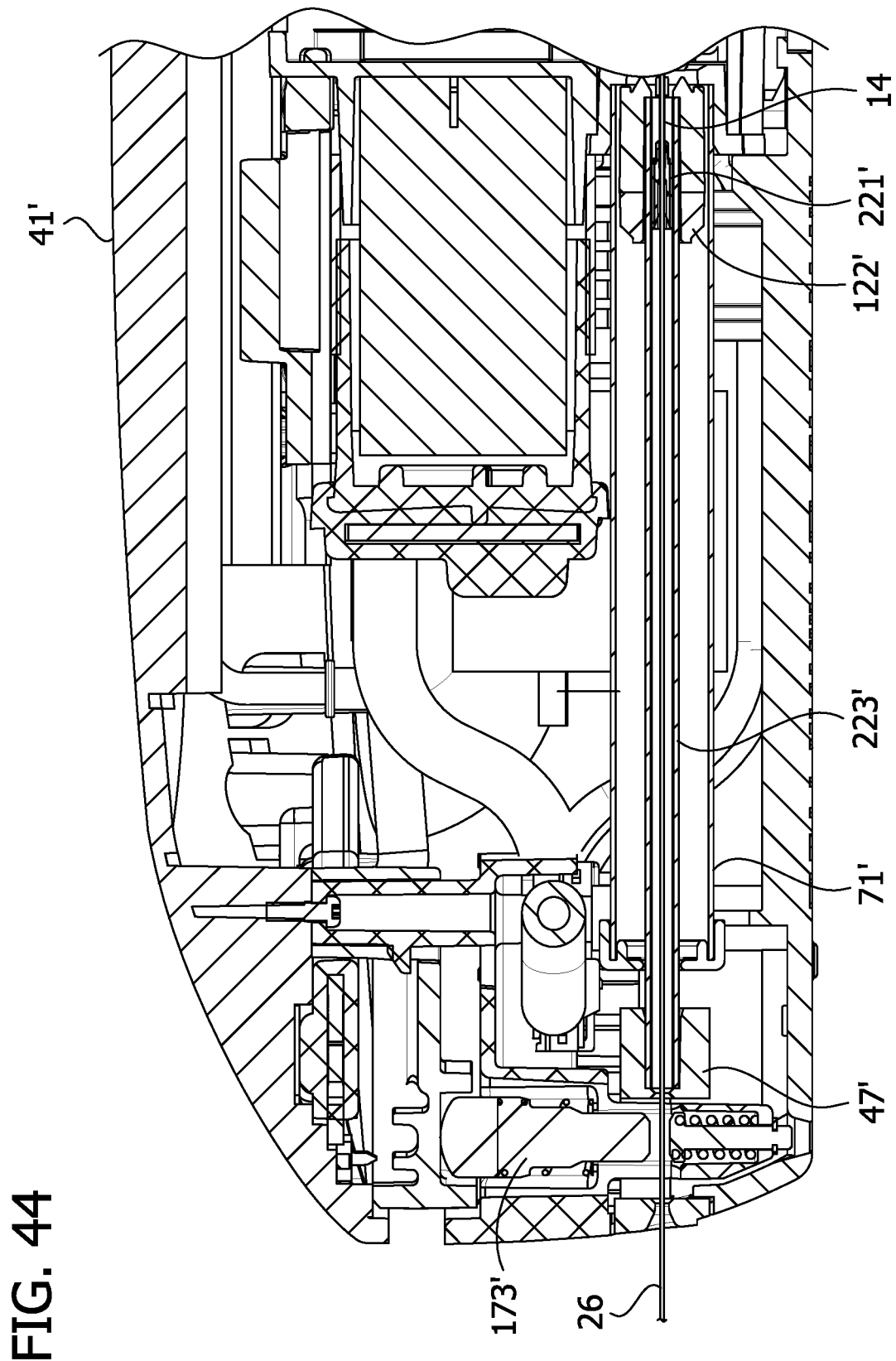
FIG. 44 is an enlarged fragmentary view of the handle of FIG. 43.
Figure 45:
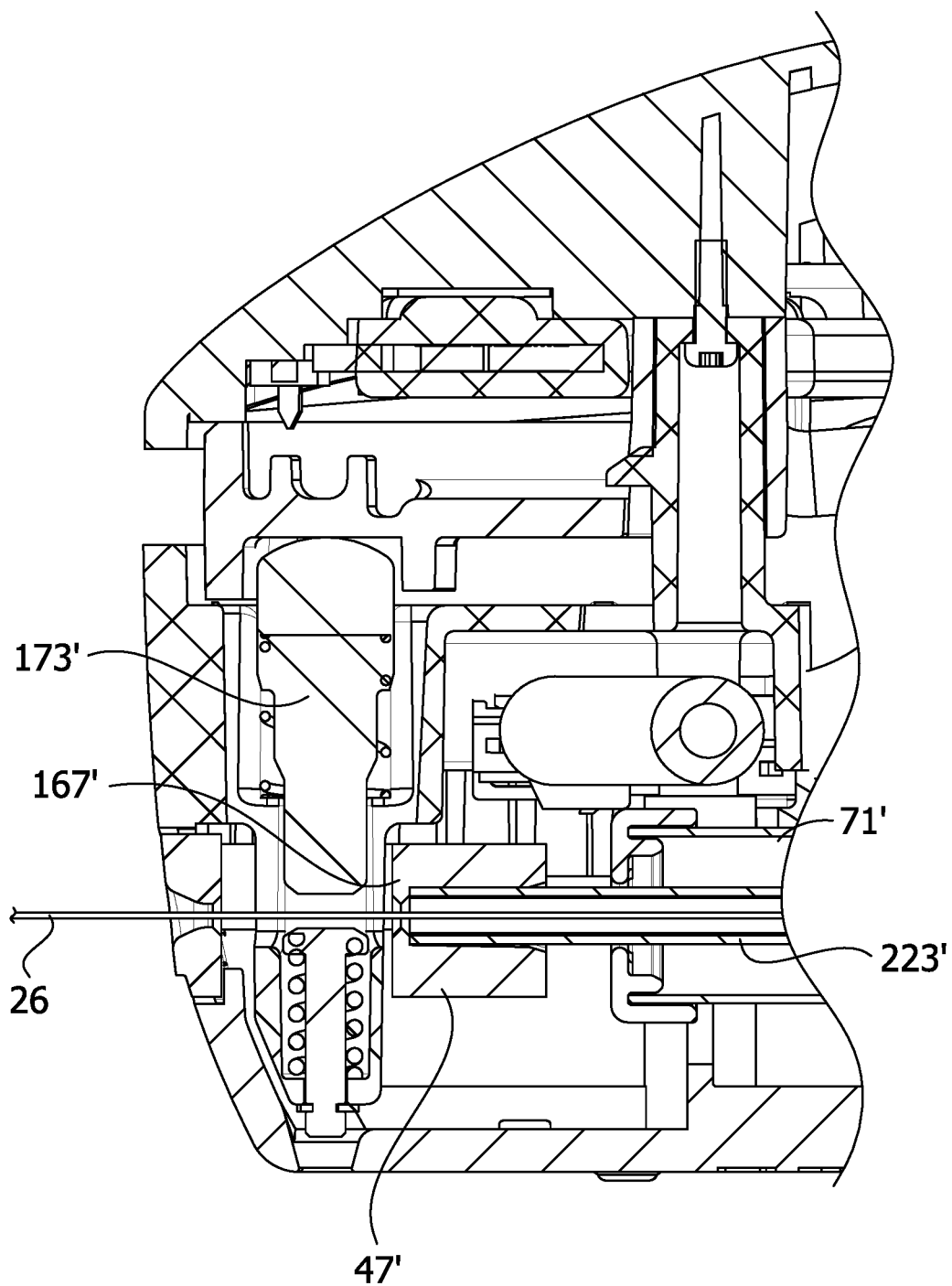
FIG. 45 is an enlarged fragmentary view of the handle of FIG. 44.
Figure 46:
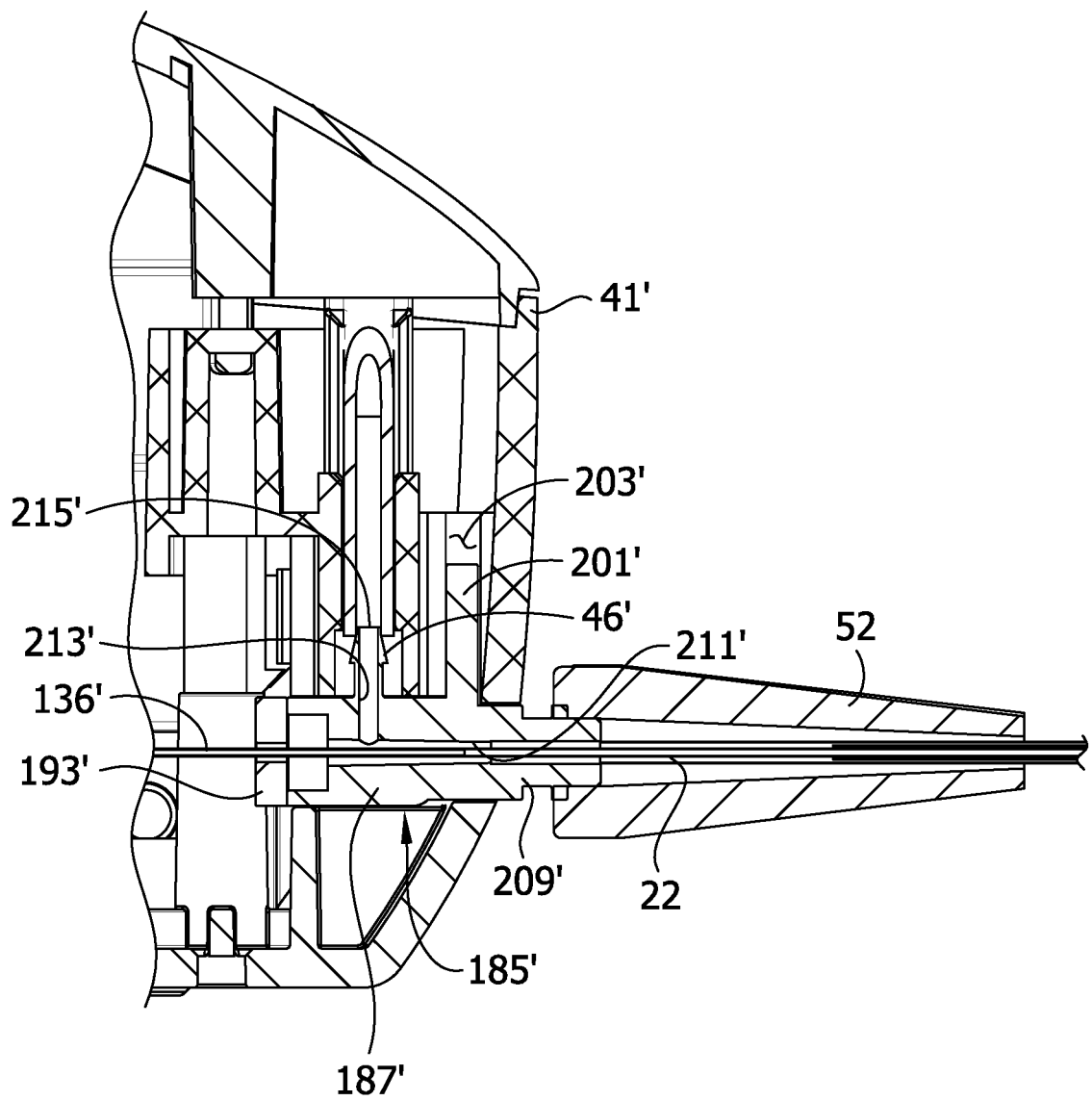
FIG. 46 is an enlarged fragmentary view of the handle of FIG. 43.

Referring to FIGS. 40-42, the handle 40' comprises a housing 41' that supports the components of the handle and includes as plurality of housing sections secured together to enclose the internal components of the handle. A mode selector 51' is mounted in the housing 41' and defines a portion of the housing. As in the earlier embodiment, the mode selector 51' is configured to selectively place the catheter 10 in a plurality of modes and lock the guide wire in place.

Figure 66:
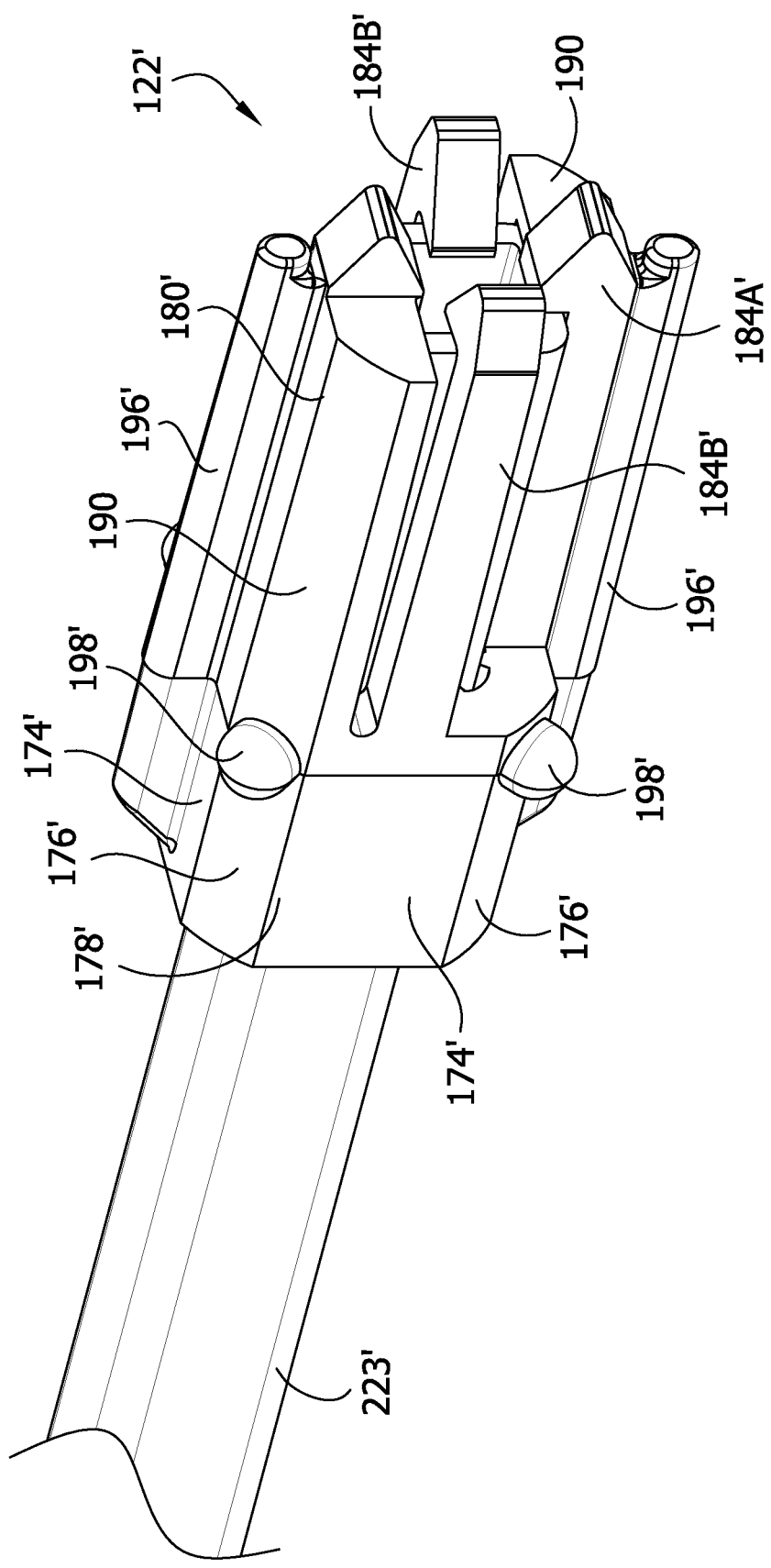
FIG. 66 is a fragmentary perspective of a guide tube and distal end stop.
Figure 67:
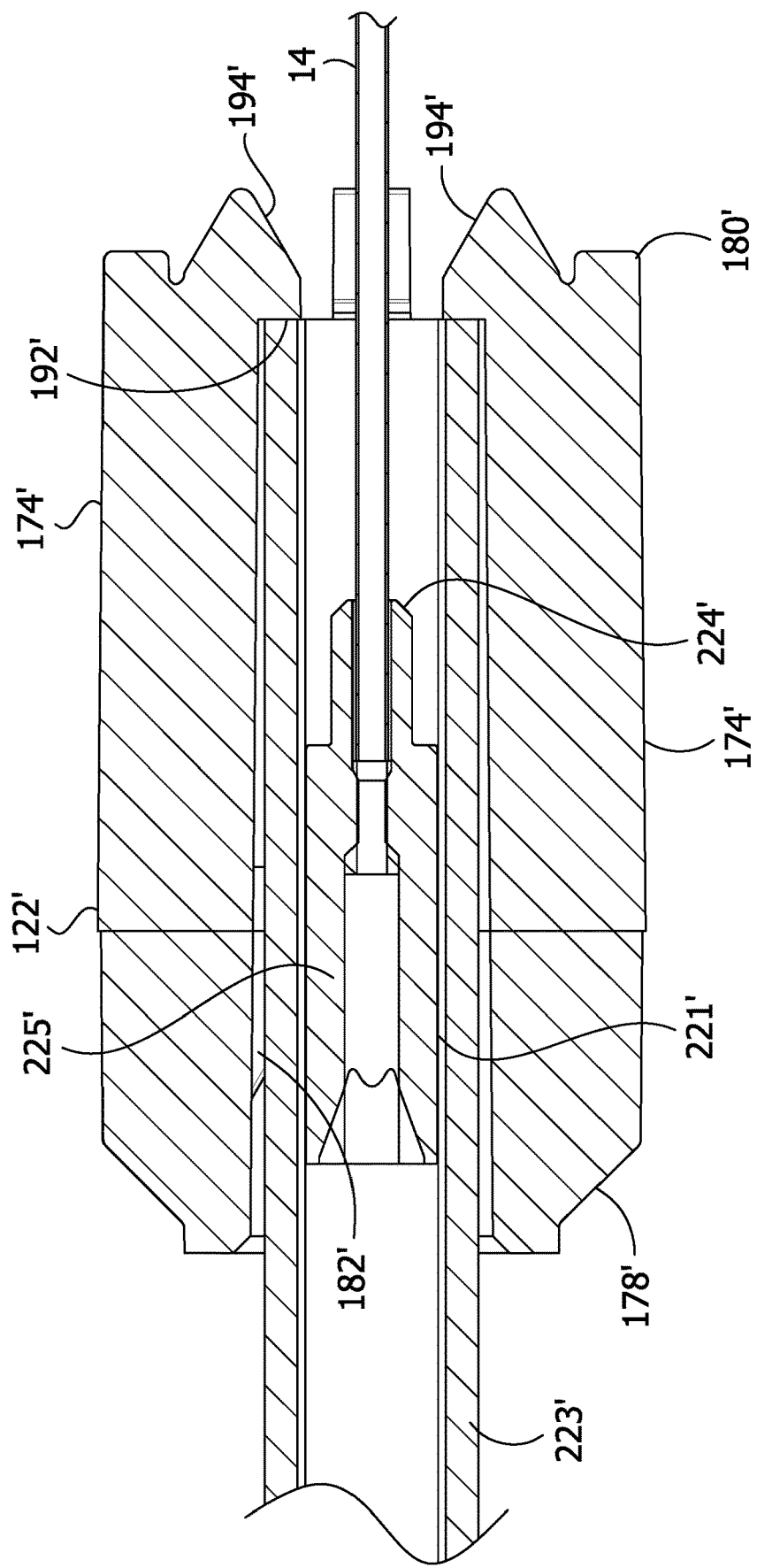
FIG. 67 is a fragmentary section of the guide tube and distal end stop showing the liner assembly received therein.
Figure 68:
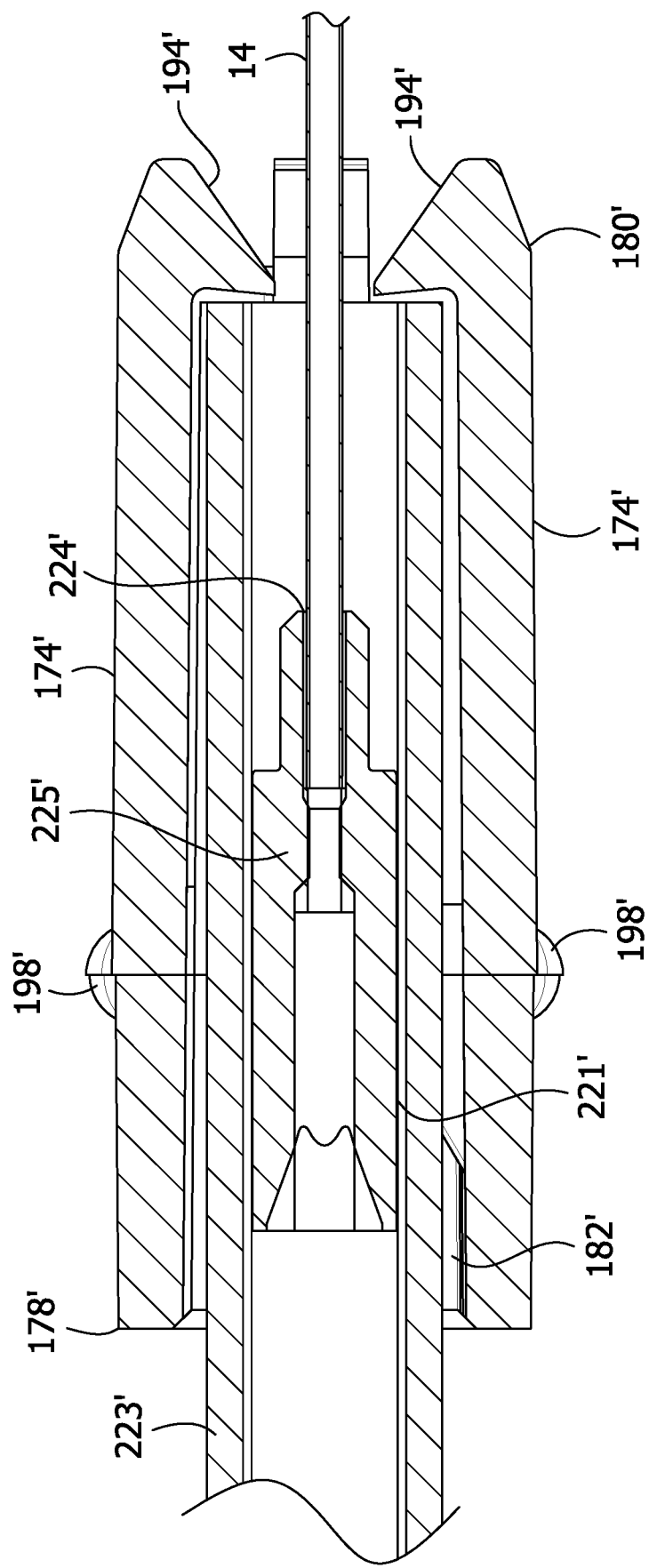
FIG. 68 is another fragmentary section of the guide tube and distal end stop showing the liner assembly received therein.
Figure 69A:
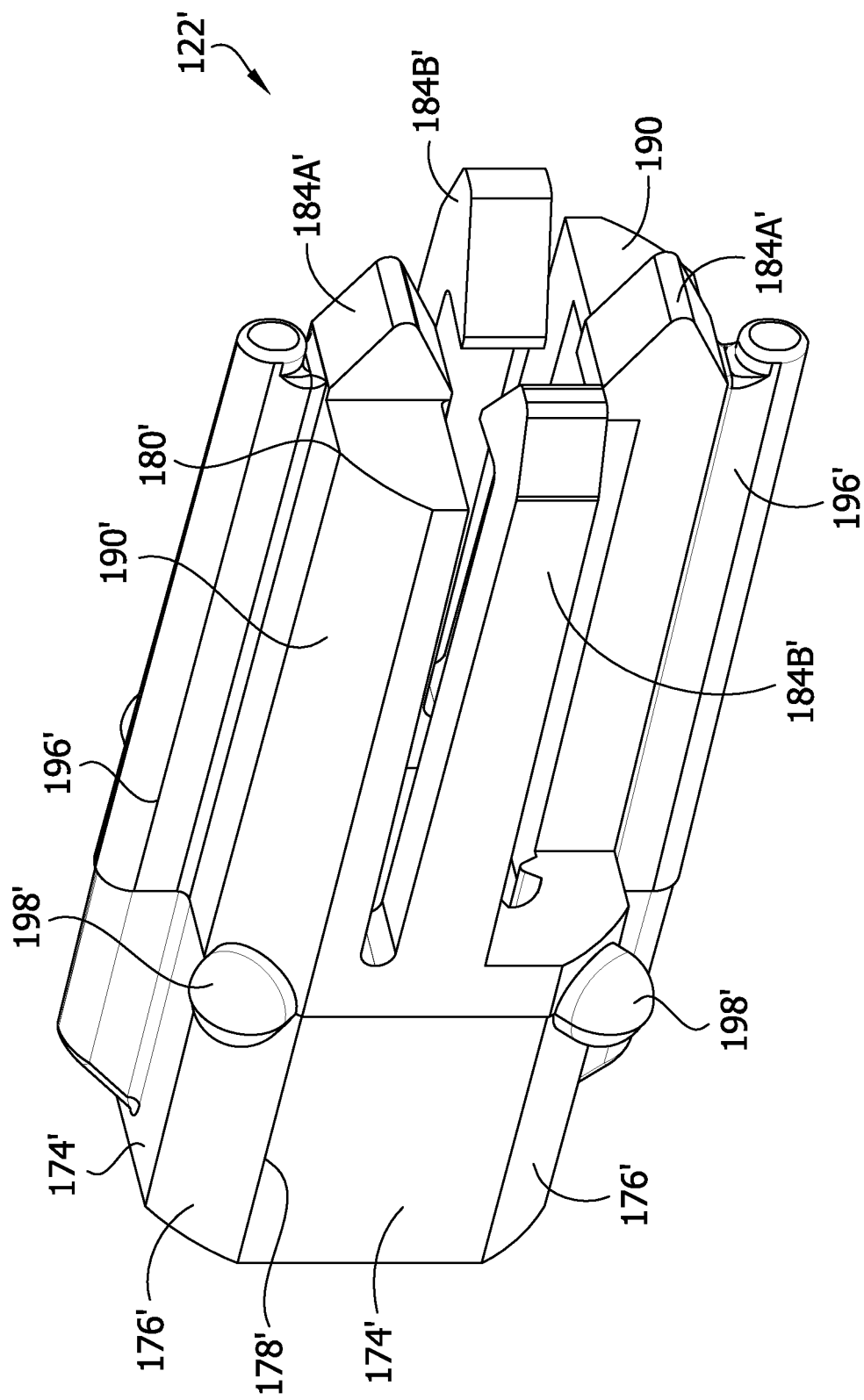
FIG. 69A is a front perspective of the distal end stop.
Figure 69B:
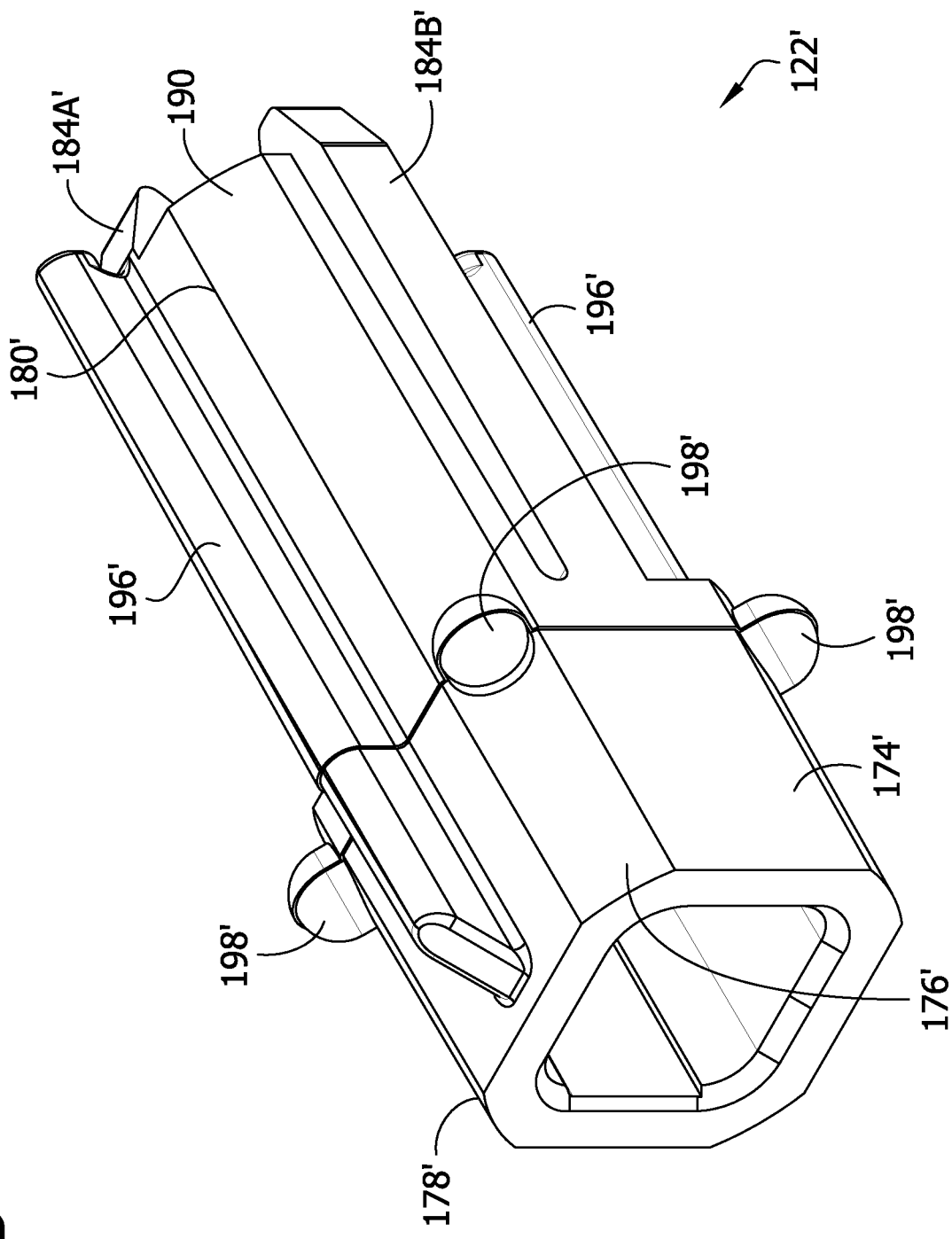
FIG. 69B is a rear perspective of the distal end stop.
Figure 70:
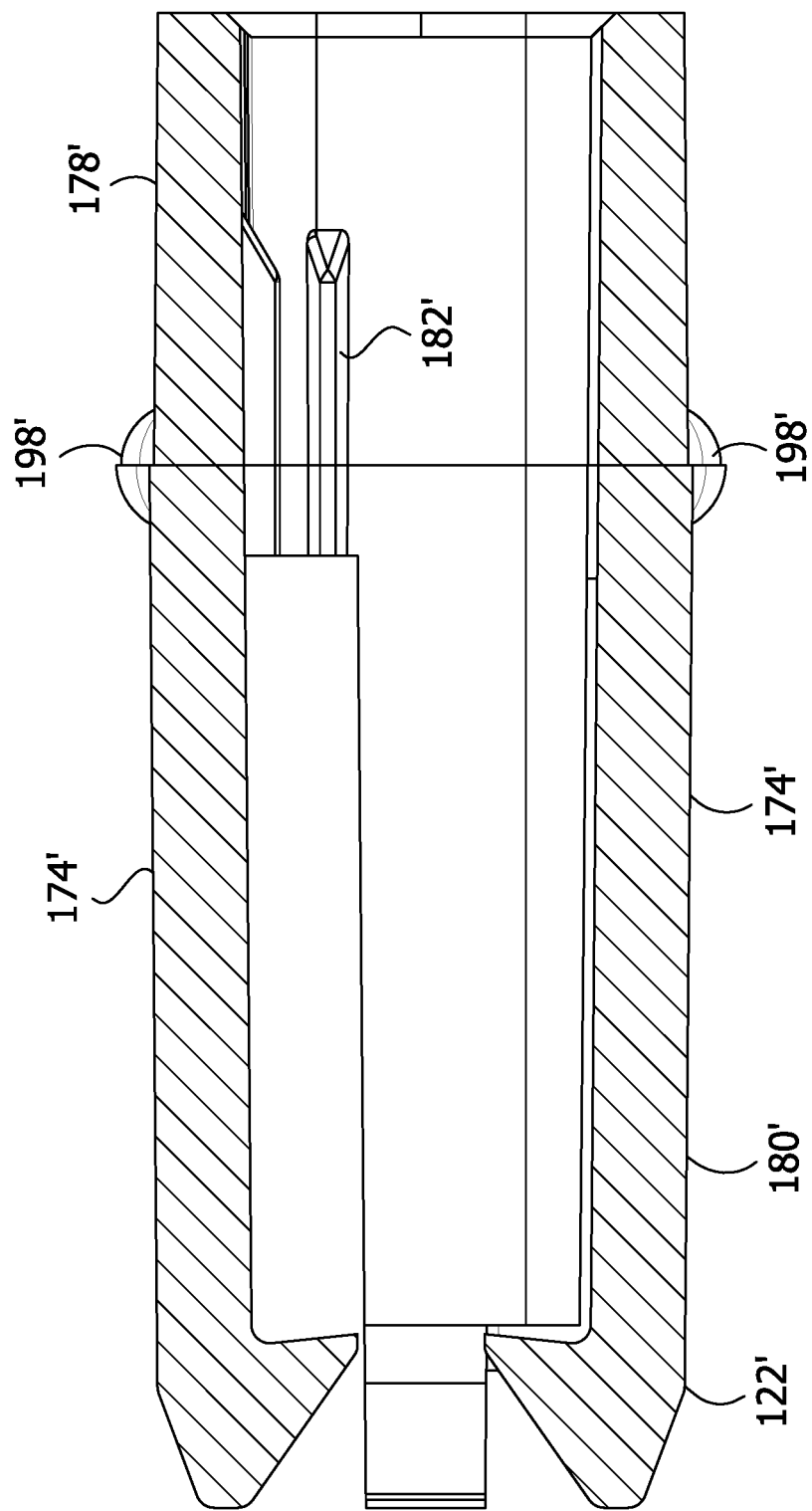
FIG. 70 is a section of the distal end stop.
Figure 71:
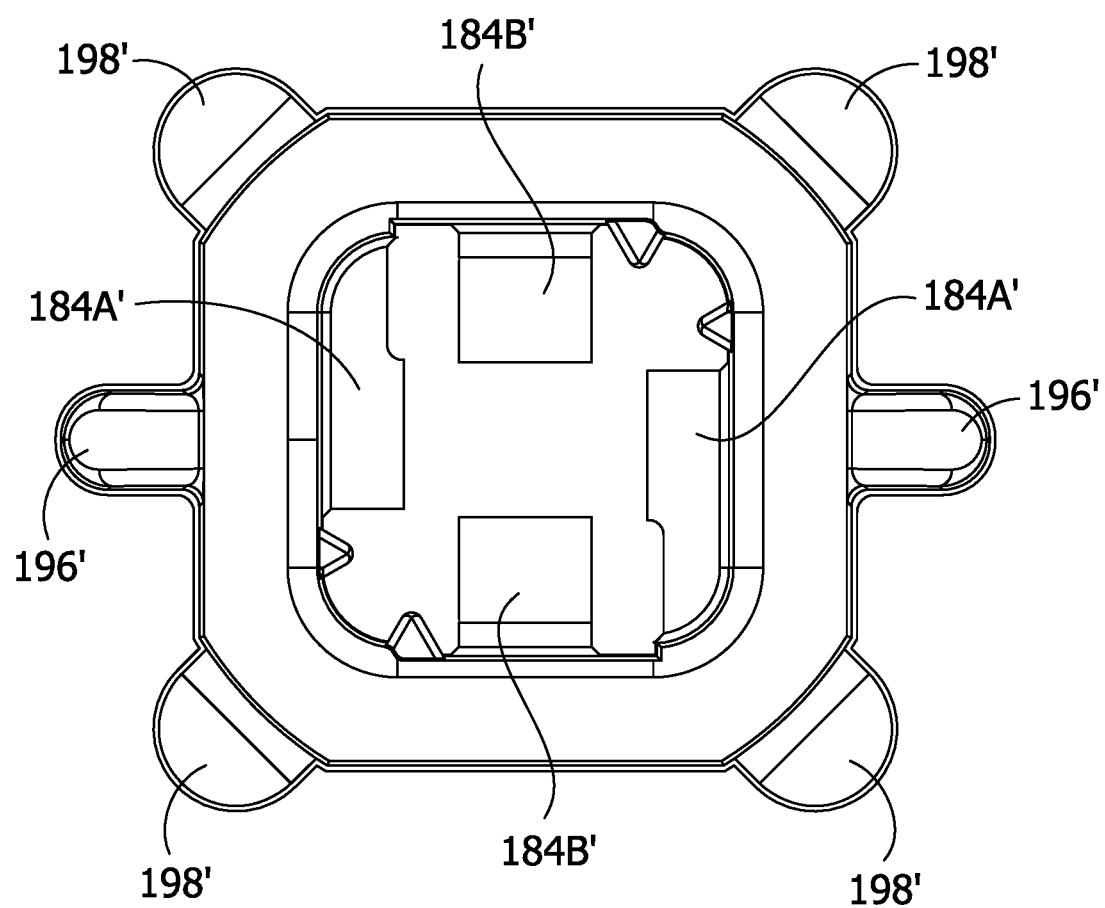
FIG. 71 is a left side view of the distal end stop.
Figure 72:
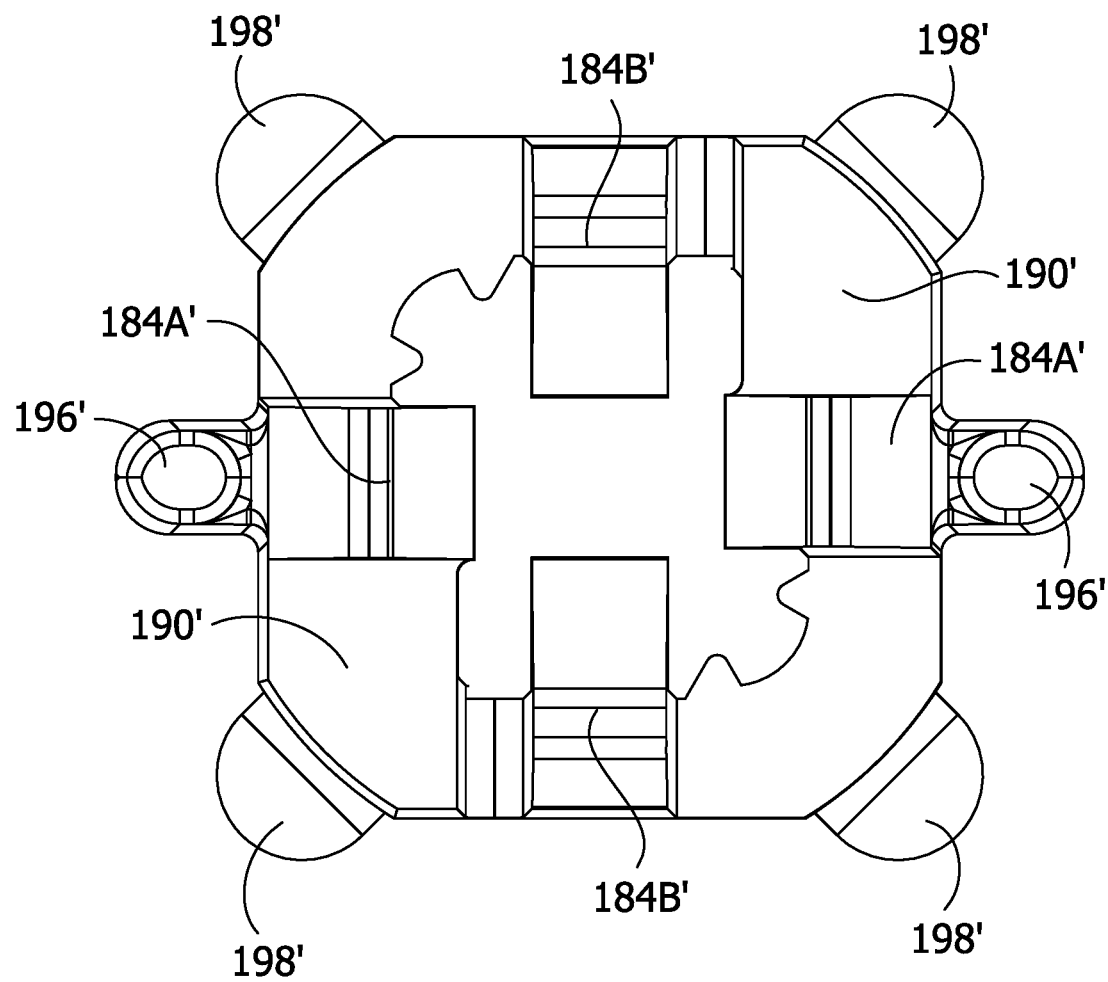
FIG. 72 is a right side view of the distal end stop.
Figure 73:
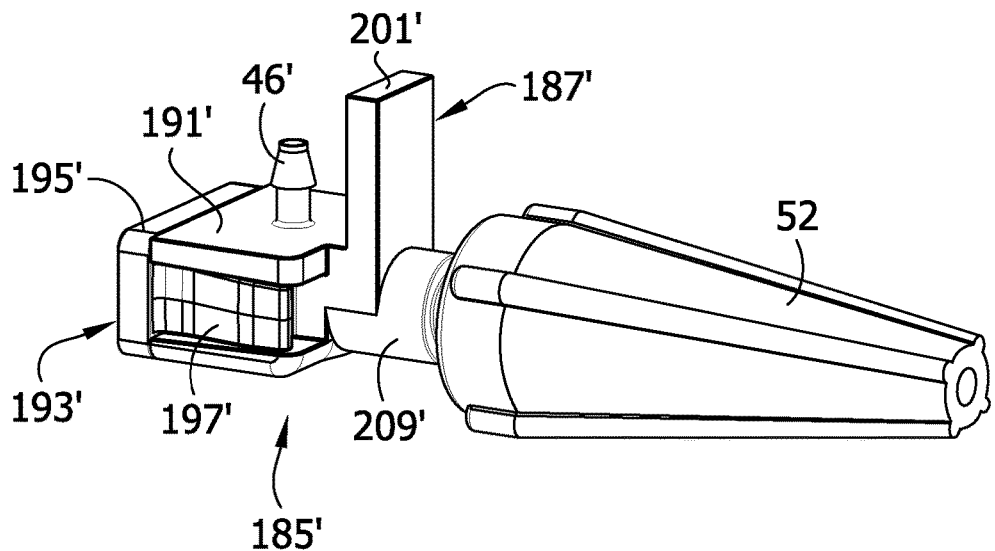
FIG. 73 is a perspective of an isolation sheath interface assembly of the handle of FIG. 40.
Figure 74:
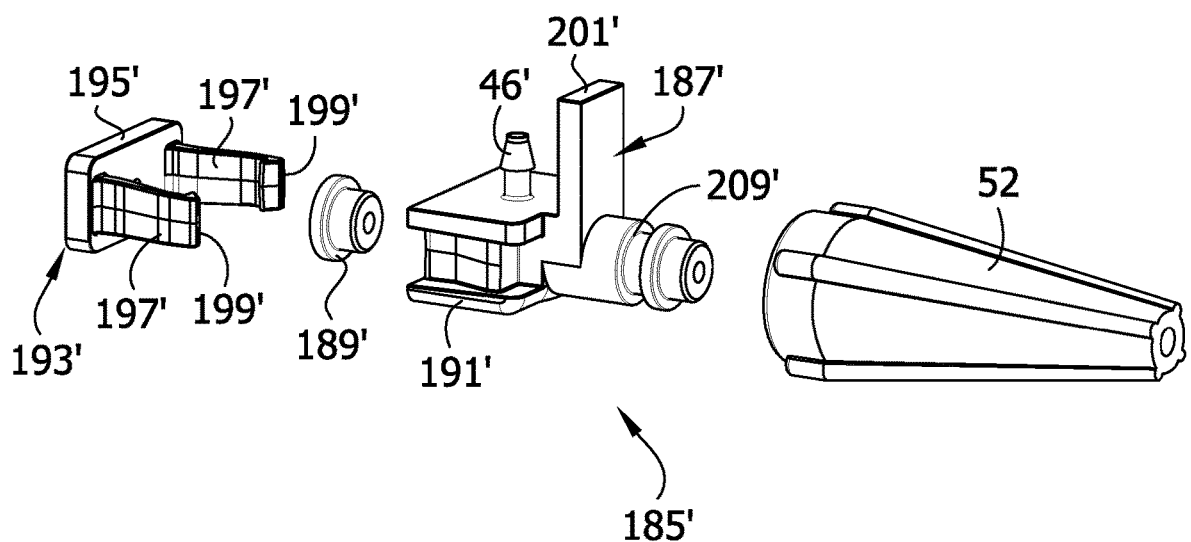
FIG. 74 is an exploded view of the isolation sheath interface assembly of FIG. 73.

Referring to FIGS. 43-50 and 52, motor 43' is coupled to the drive coil 12 by a gear assembly 44' and drive assembly 48' supported within the housing 41'. The gear assembly 44 comprises a gearbox housing 55' that mounts and at least partially encloses a pair of gears for transferring the rotation of a shaft 124' of the motor 43' to the drive coil 12. The gearbox housing 55' includes a rear housing section 61' and front housing section 63' formed integrally with the rear housing section such that the gearbox housing comprises a single housing structure. The rear housing section 61' includes a motor sleeve 120' on a proximal side of the rear housing section that receives a distal end portion of the motor 43', and a tube sleeve portion 69' on the proximal side of the rear housing section that receives a distal end portion of a buckle tube 71' and a distal end stop 122' on guide tube 223' (FIG. 66). The rear housing section 61 also attaches to a carriage or advancer frame 73' via fasteners 75 for moving the motor 43' and gear assembly 44' within the housing 41'. The front housing section 63' has a distal sleeve portion 77' (FIG. 55) that receives a portion of drive assembly 48'. A driver gear 81' is attached to motor shaft 124' (FIG. 49) such that the driver gear rotates with the motor shaft when the motor 43' is activated. In one embodiment, the driver gear 81' is press fit on to the motor shaft 124'. A driven gear 83 (FIG. 55) is in mesh with the driver gear 81 so that rotation of the driver gear causes the driven gear to rotate in the opposite direction. The drive assembly 48' attaches the driven gear 83' to the drive coil 12 so that the rotation of the driven gear causes the drive coil to rotate.

Referring to FIGS. 57-63, the drive assembly 48' comprises a gear insert 85' (broadly, a gear extension) extending through the driven gear 83', and a lock 89' received in a distal end of the gear insert. In one embodiment, the gear insert 85' is press fit into the driven gear 83'. Alternatively, the gear insert 85' may be formed integrally with the driven gear 83'. The gear insert 85' has a proximal portion 130' extending through the driven gear 83' and proximally from the driven gear, and a distal portion 132' extending distally from the driven gear. The proximal portion 130 comprise a cylindrical member having a uniform outer diameter extending along its length. An inner space 134' (FIG. 60) of the proximal portion 130 has a generally rectangular cross section. The distal portion 132' comprise a hollow rectangular projection defining four planar sides. Openings 135' in each of the sides communicate with an interior of the distal portion 132'. Ramp surfaces 138' on an interior side of the four sides extend from a distal end of the distal portion 132' to respective axial surfaces 140' in the distal portion. The openings 135' extend through the axial surfaces 140'. The gear insert 85' may be formed from any suitable material including without limitation, stainless steel and Peek.

The lock 89' comprises a base portion 105', a pair of arms 106' projecting from a distal end of the base portion, and fingers 107' projecting laterally from a distal end of the arms. The base portion 105' has a generally rectangular cross section. In the illustrated embodiment, there are two arms 106' with each arm having two fingers 107' extending therefrom. However, another number of arms 106' and fingers 107' could be used without departing from the scope of the disclosure. Each of the fingers 107' has an elongate portion 109' and a hook portion 111' projecting laterally from the elongate portion away from a central axis of the lock 89'. In the illustrated embodiment, the hook portions 111' projection orthogonally from the elongate portions 109'. The hook portions 111' on each arm 106' extend in opposite directions. Ramps 112' (broadly, catches) extend laterally outward from the arms 106' between the fingers 107'. The lock 89' may be formed from any suitable material including without limitation, stainless steel.

The base portion 105' of the lock 89' is inserted into the distal portion 132' of the gear insert 85' and into the interior space 134' to secure the lock to the gear insert. As the lock 89' is inserted into the gear insert 85', the ramps 112' on the lock will engage the ramp surfaces 138' in the gear insert causing the arms 106' to flex inward allowing the lock to be further inserted into the gear insert until the ramps are received in respective openings 135' in the gear insert. Distal end surfaces of the ramps 112' oppose edges of the openings 135' preventing the lock from being pulled back out of the gear insert 85'. With the lock 89' fully inserted, the hook portions 111' of the fingers 107 oppose the distal end of the gear insert 85'. The engagement between the hook portions 111' and the distal end of the gear insert 85' holds the lock 89' in place in the gear insert 85' when the drive coil 12 and drive assembly 48' are placed in compression. The connection between the ramps 112' on the lock 89' and the gear insert 85' holds the drive assembly 48' together when the drive coil 12 and drive assembly are placed in tension. While ramps 112' are shown in the illustrated embodiment, it is envisioned that catches having other configurations could be used. For example, projections without a sloped ramp surface such as rectangular projections could be used. Still other catch configurations are envisioned within the scope of the disclosure. Bearings 146' (FIGS. 54 and 55) are disposed around the proximal portion 130' of the gear insert 85'. The bearings 146' provide additional stabilization of the rotating gear assembly 48'. A projection 150' (broadly, a weld feature) on a proximal end of base portion 105' provides a surface for welding the lock 89' to the drive coil 12.

Similar to the previous embodiment, this configuration provides overlap of the lock 89' with the gear insert 85' which facilitates a better transfer of rotation to the drive coil 12 and allows the drive assembly 48' to better withstand the torque applied to the drive assembly. The connection between the lock 89' and the gear insert 85' also holds the drive assembly 48' together when the drive coil 12 and drive assembly are placed in tension. Further, the rectangular cross section of the interior space 134' of the gear insert 85' receives the rectangular base portion 105' of the lock 89' which is welded to the drive coil 12. Thus, the engagement between the lock 89' and the gear insert 85' prevents relative rotation of the components which provides for a better transfer of torque from the driven gear 83' to the drive coil 12. In one embodiment, the lock 89' is formed from stainless steel. However, other suitable materials may be used without departing from the scope of the disclosure.

Additionally, the drive assembly 48' even further reduces the number of components for interfacing with the drive coil 12 to couple the handle 40' to the catheter body. The drive assembly 48' also enables assembly and disassembly of the drive assembly by only requiring access to the distal end of the gear shaft through the gearbox housing 55'.

Figure 64:
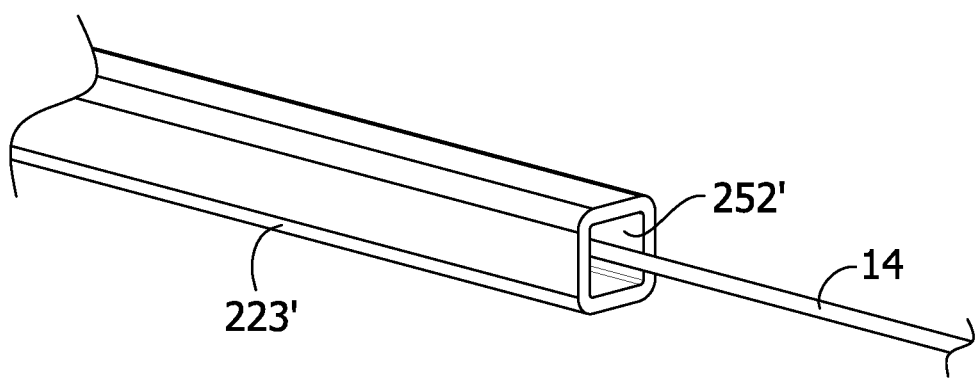
FIG. 64 is a fragmentary perspective of a guide tube and liner assembly received in the guide tube.
Figure 65:
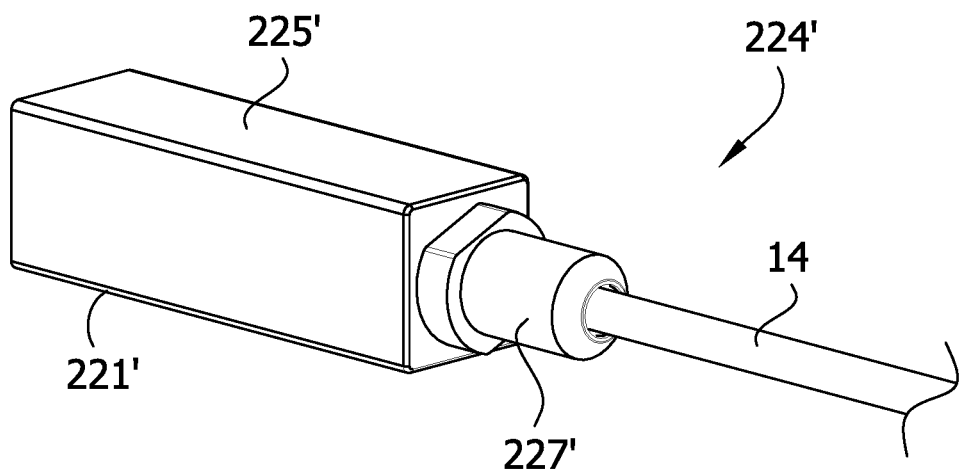
FIG. 65 is a fragmentary perspective of the inner liner assembly.

Referring to FIGS. 64 and 65, a liner key 221' is attached to a proximal end of the liner 14 and is received in guide tube 223' fixedly mounted in the handle 40. Just as in the previous embodiment, the engagement between the liner key 221' and the guide tube 223' permits the liner key and liner 14 to translate relative to the guide tube but prevents rotation of the liner key and liner relative to the guide tube. The liner key 221' comprises a rectangular member 225' and an elongate tubular member 227' extending distally from a distal end of the rectangular member. The proximal end of the liner 14 is received and retained in the elongate tubular member 227'. The liner 14 can be retained in the liner key 221 by any suitable means, including without limitation, glue, thermal bond, and mechanical bond. Thus, the liner key 221' and the liner 14 co-translate with each other. In the illustrated embodiment, the guide tube 223' has a rectangular passage 252' so that the dimensions of the guide tube and liner key 221' prevent relative rotation. The configuration of the liner key 221' and guide tube 223' also reduces the friction on the liner 14 during advancement and retraction of the liner. Alternatively, the guide tube 223' may have a generally circular interior passage. The liner key 221' configuration also facilitates assembly of the handle 40' by allowing the key to be inserted though the gearbox housing 55'. It is envisioned that the liner key 221' and guide tube 223' can have other configurations for permitting relative translation and preventing relative rotation. Further, any suitable materials may be used for the liner key 221' and guide tube 223'. For example, the liner key 221, can be formed from Peek, Polyoxymethylene (POM), or polycarbonate (PC). The inner liner 14 and liner key 221' may be broadly considered a liner assembly 224'.

Figure 47:
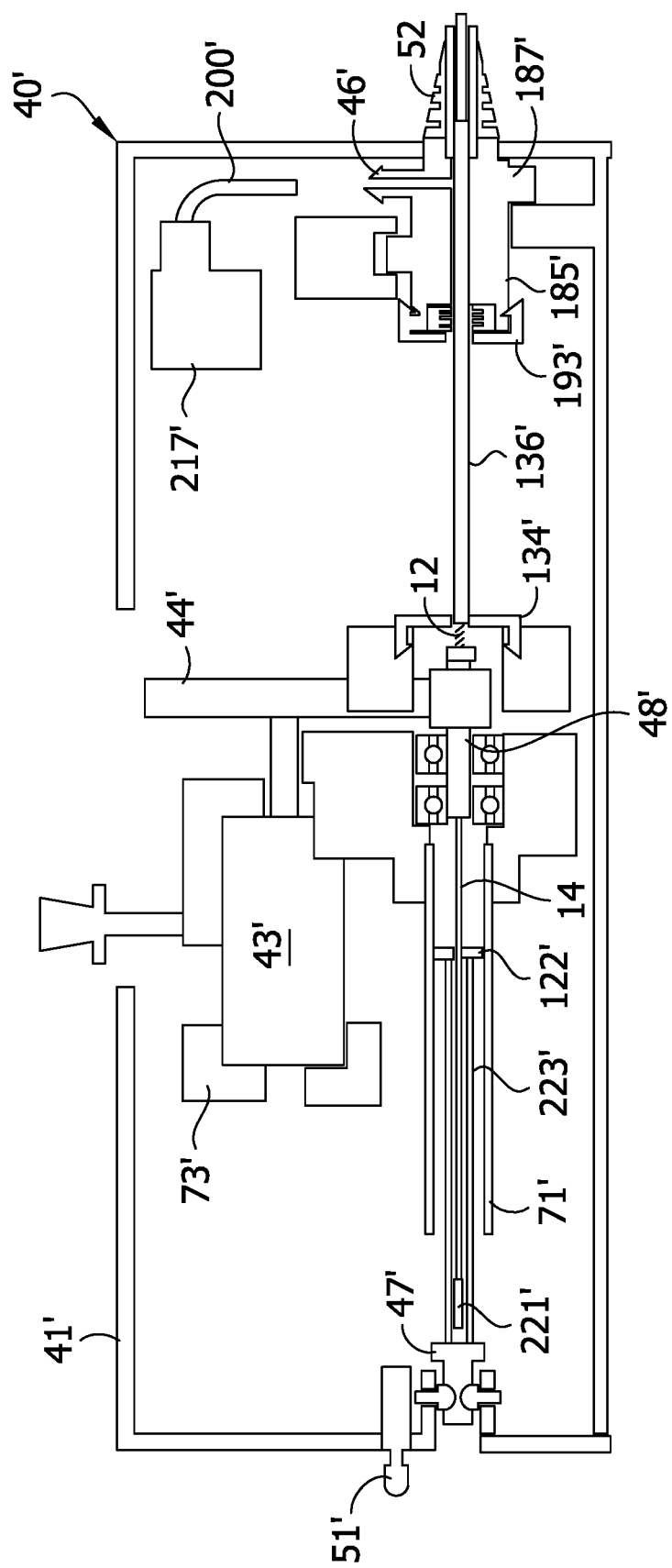
FIG. 47 is a schematic illustration of the catheter of FIG. 40.
Figure 48:
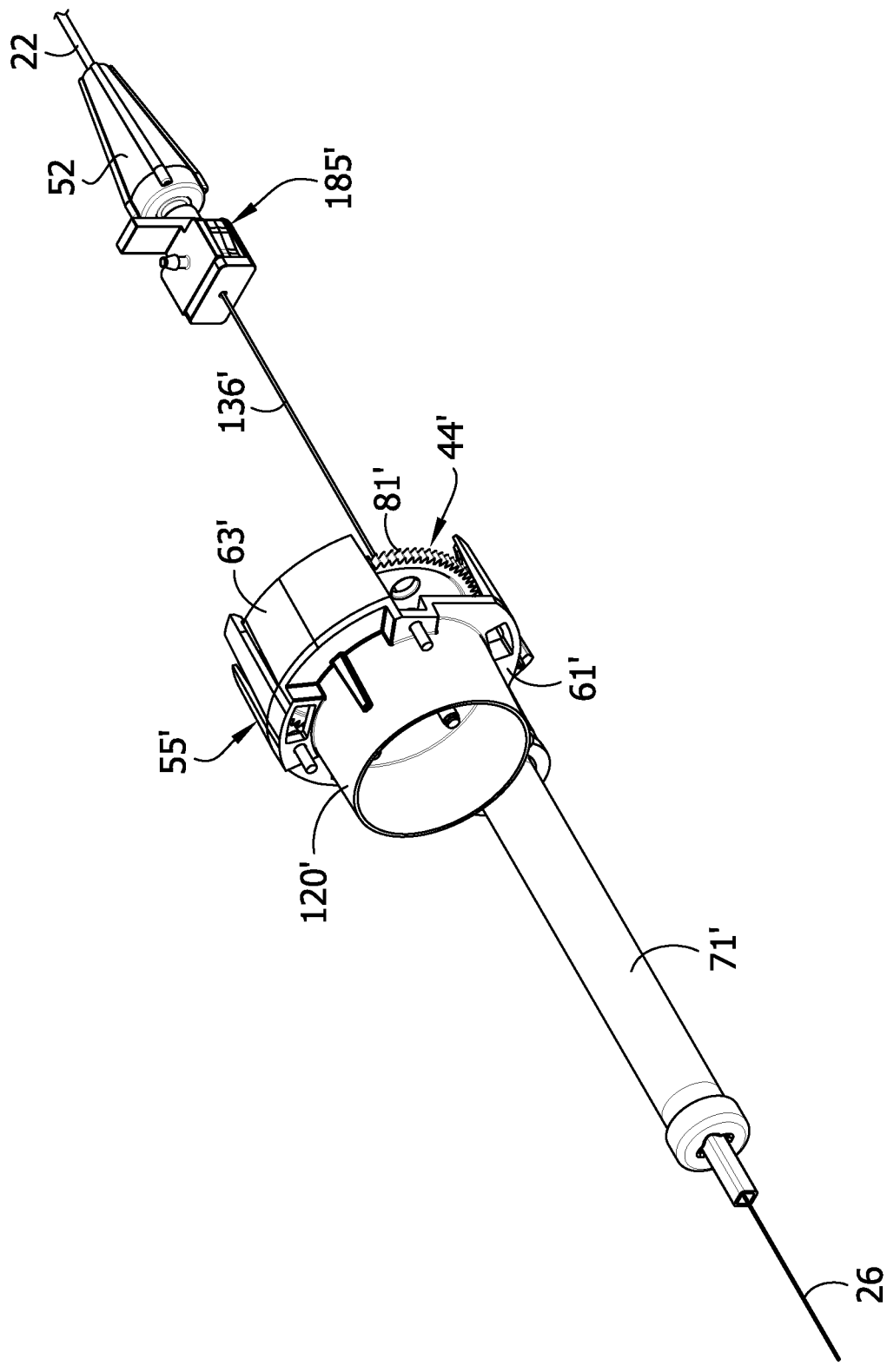
FIG. 48 is a rear perspective of components of the handle and a catheter assembly extending through the handle.
Figure 49:
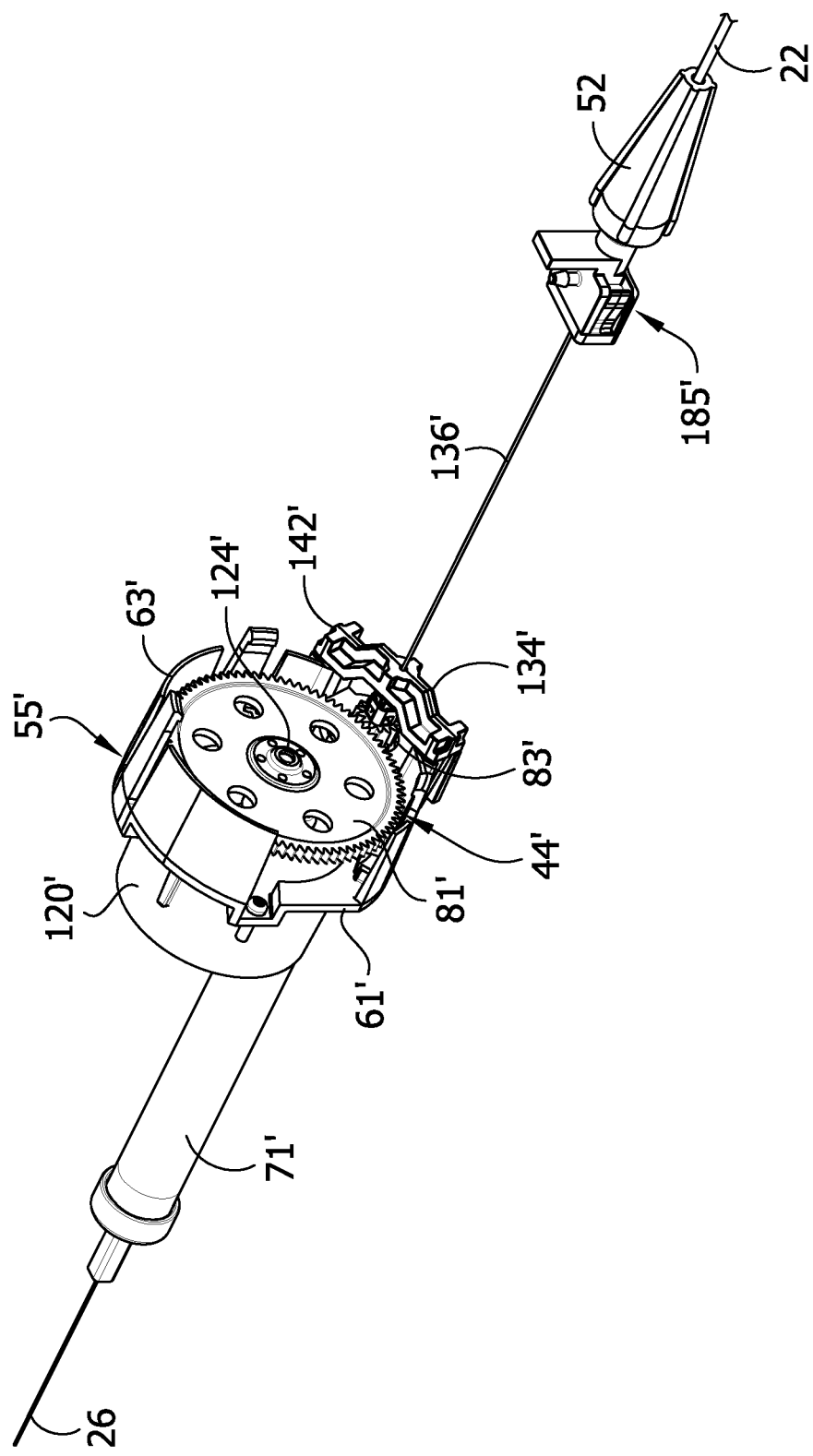
FIG. 49 is a front perspective of components of FIG. 48.
Figure 50:
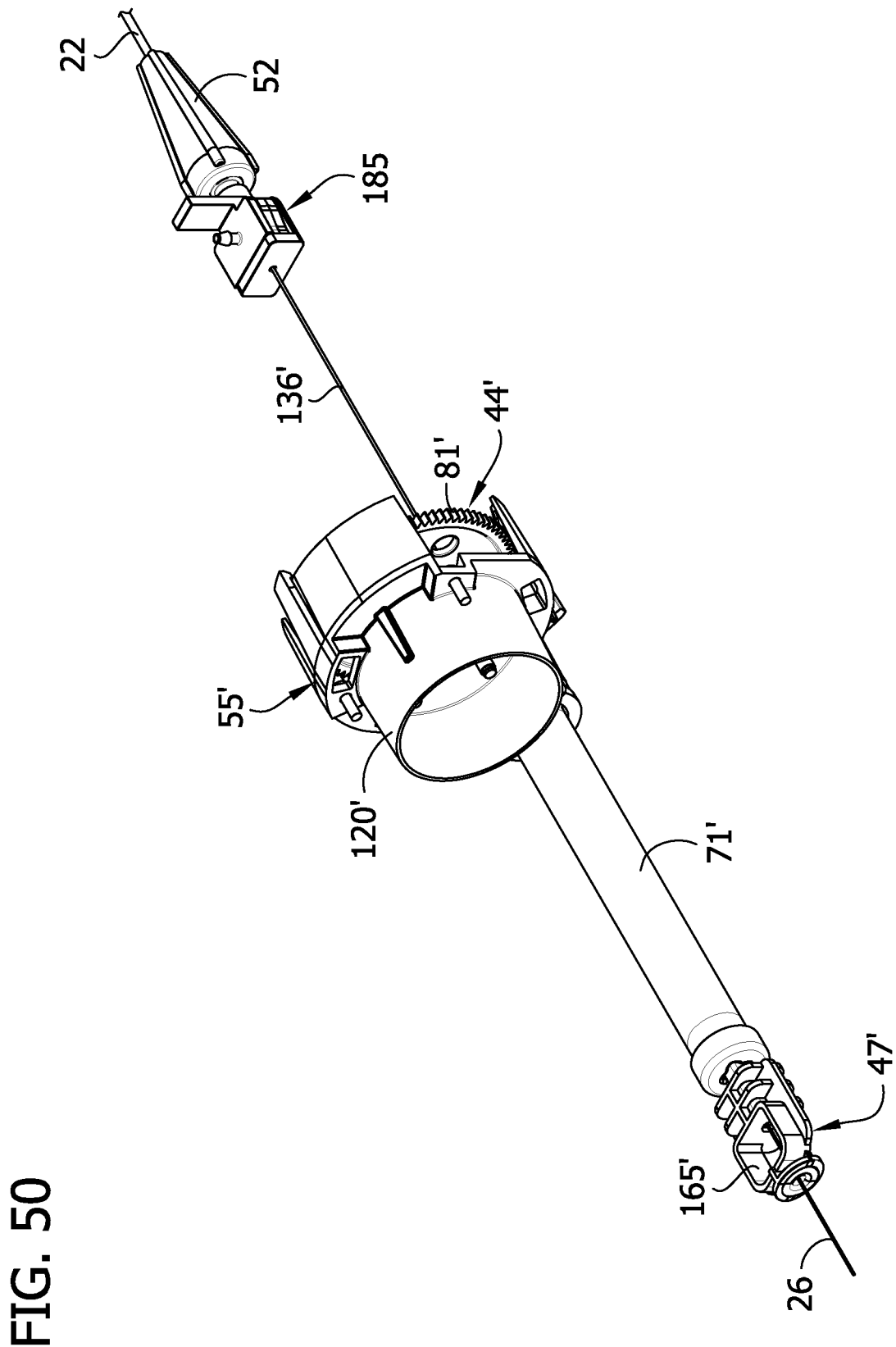
FIG. 50 is a rear perspective of components of the handle and the catheter assembly extending through the handle.
Figure 51:
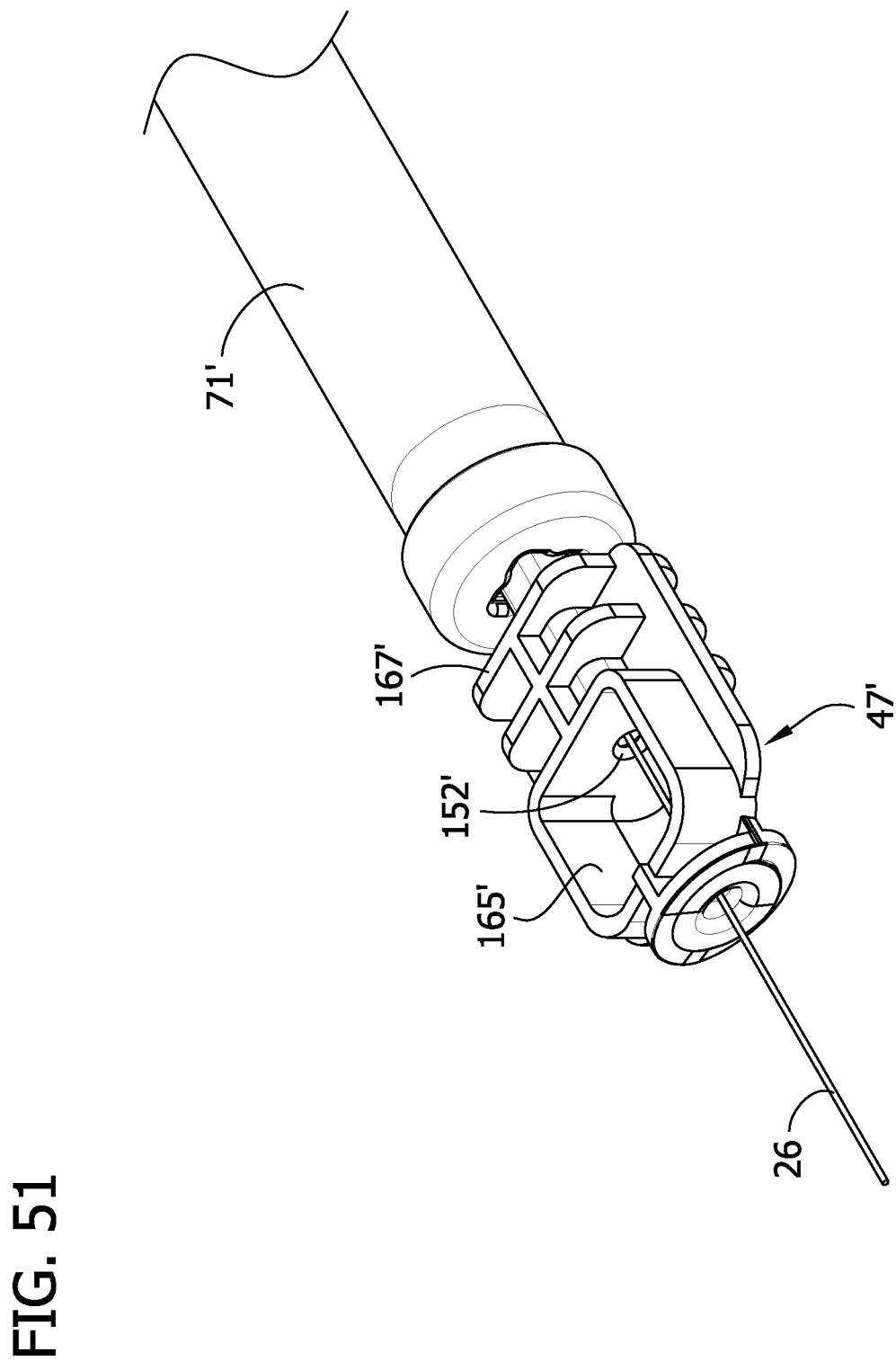
FIG. 51 is an enlarged fragmentary perspective of FIG. 50.
Figure 52:
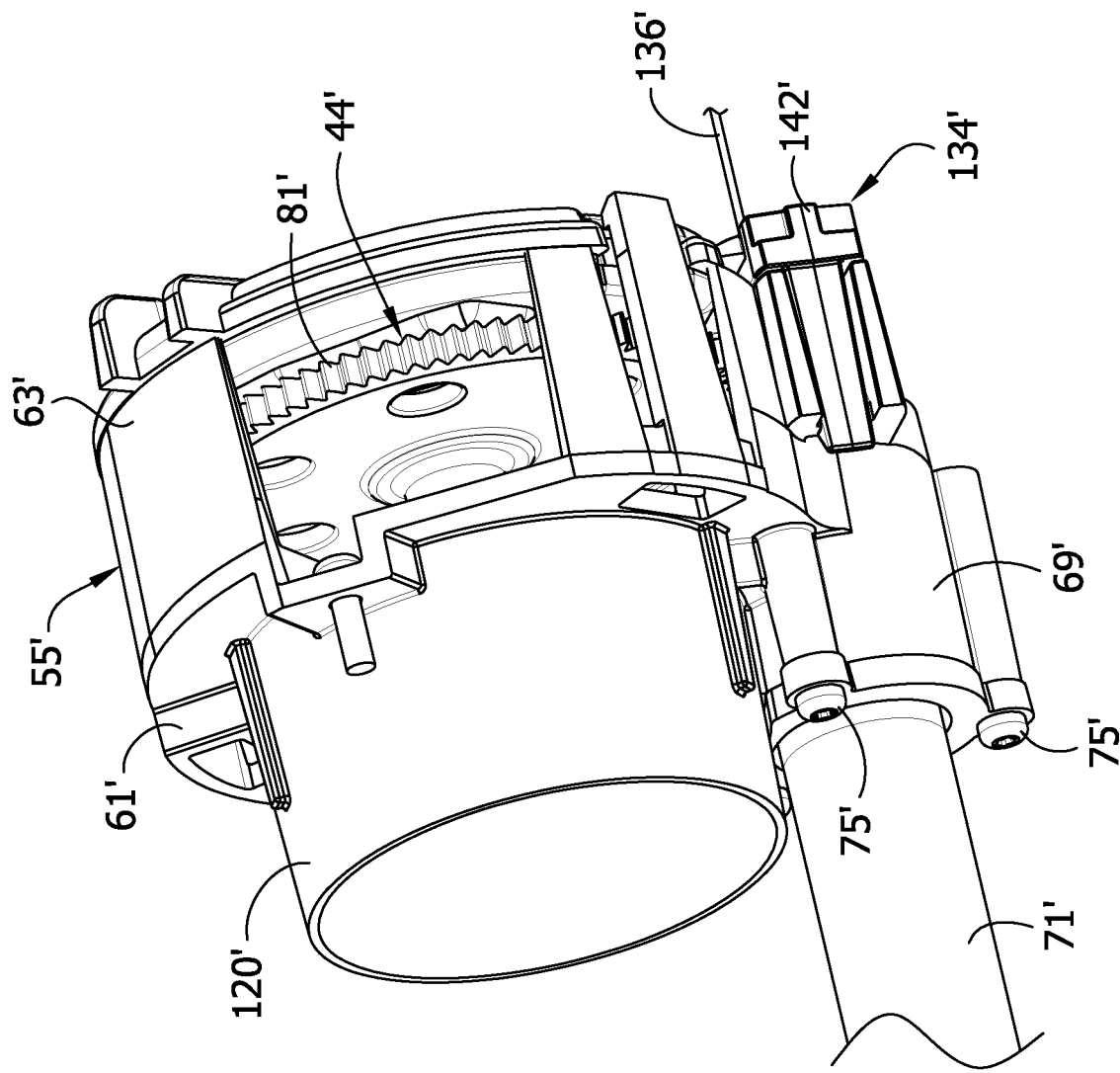
FIG. 52 is an enlarged fragmentary perspective of the components of FIG. 50.
Figure 53:
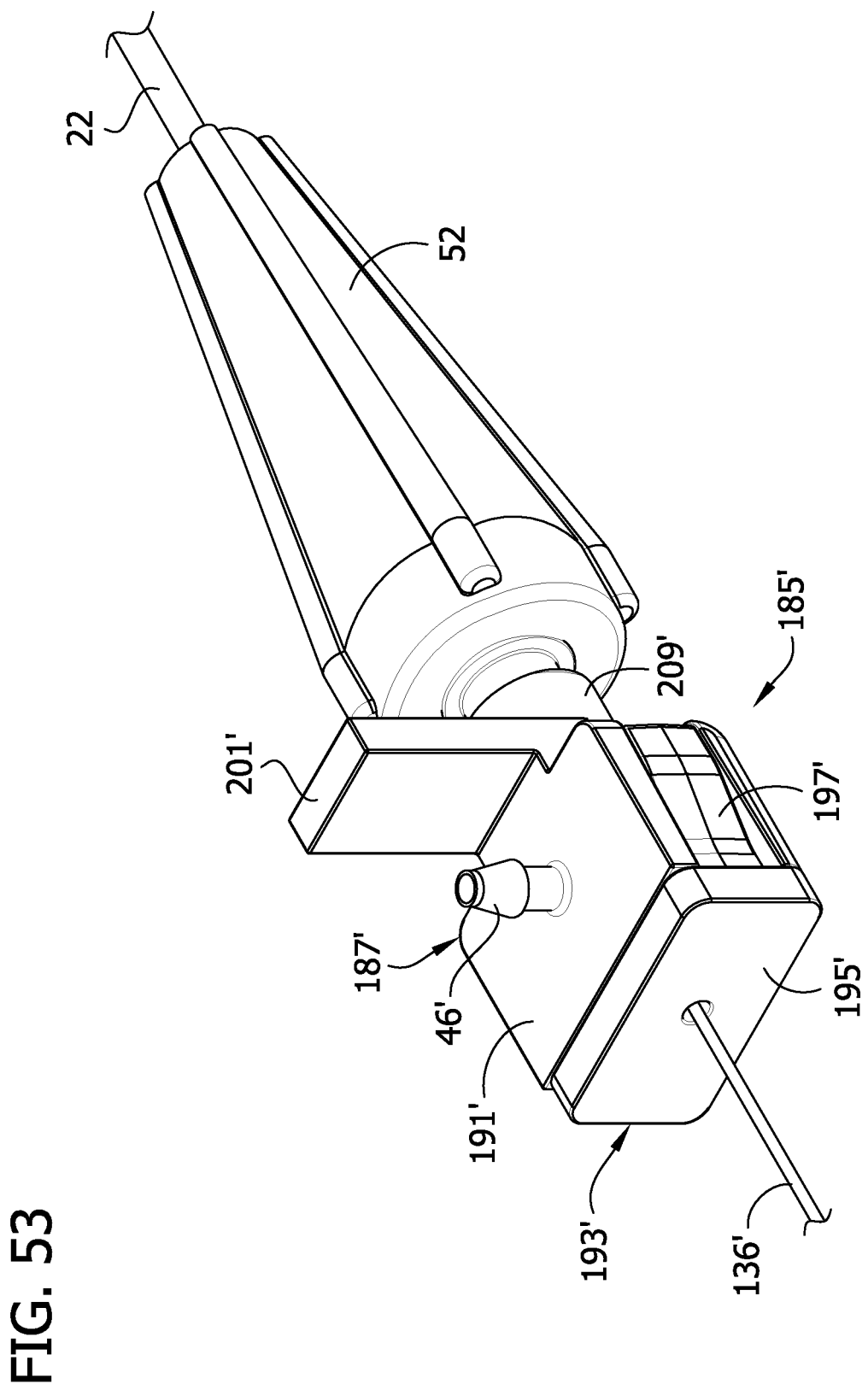
FIG. 53 is an enlarged fragmentary perspective of FIG. 50.
Figure 54:
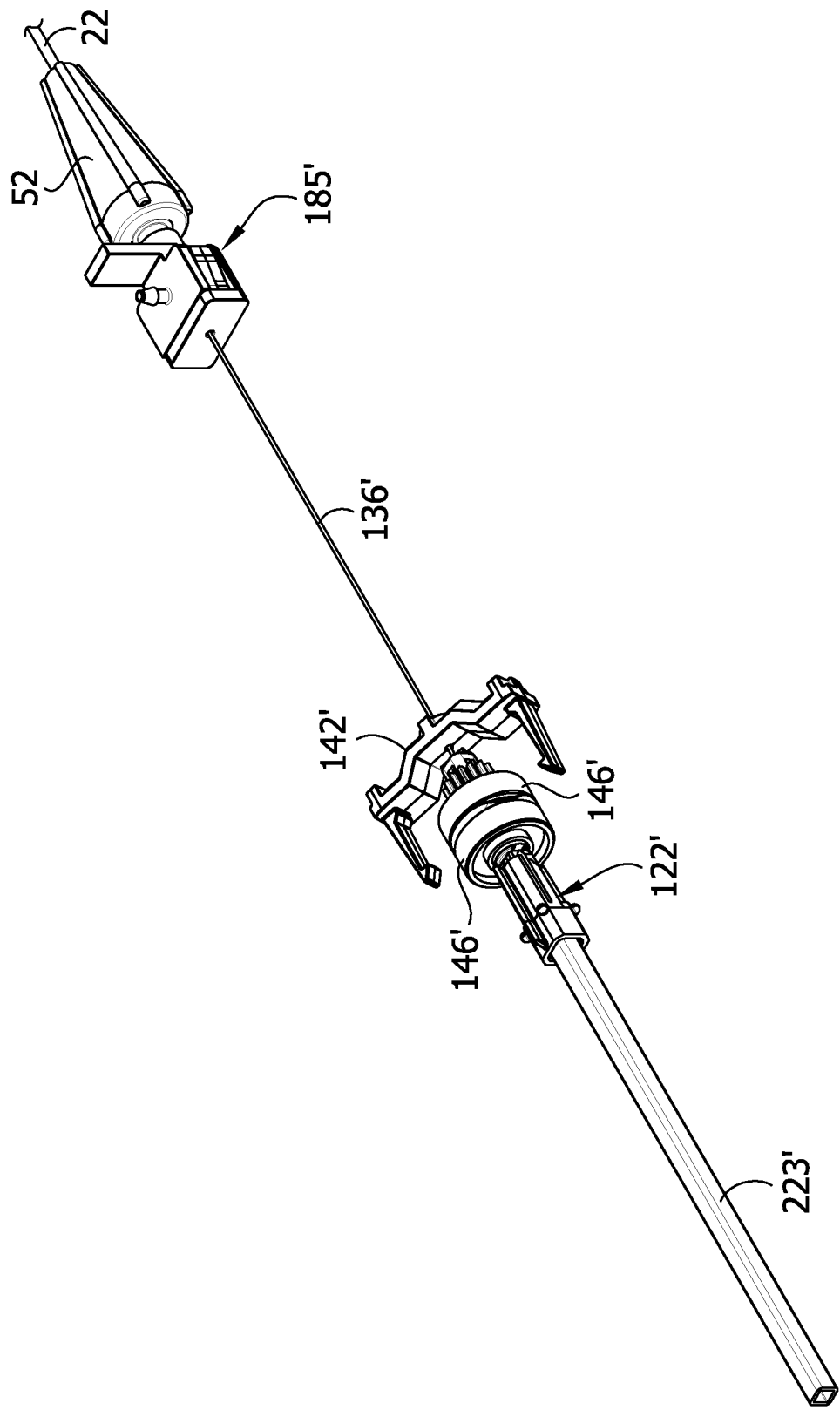
FIG. 54 is a rear perspective of components of the handle and the catheter assembly extending through the handle.
Figure 55:
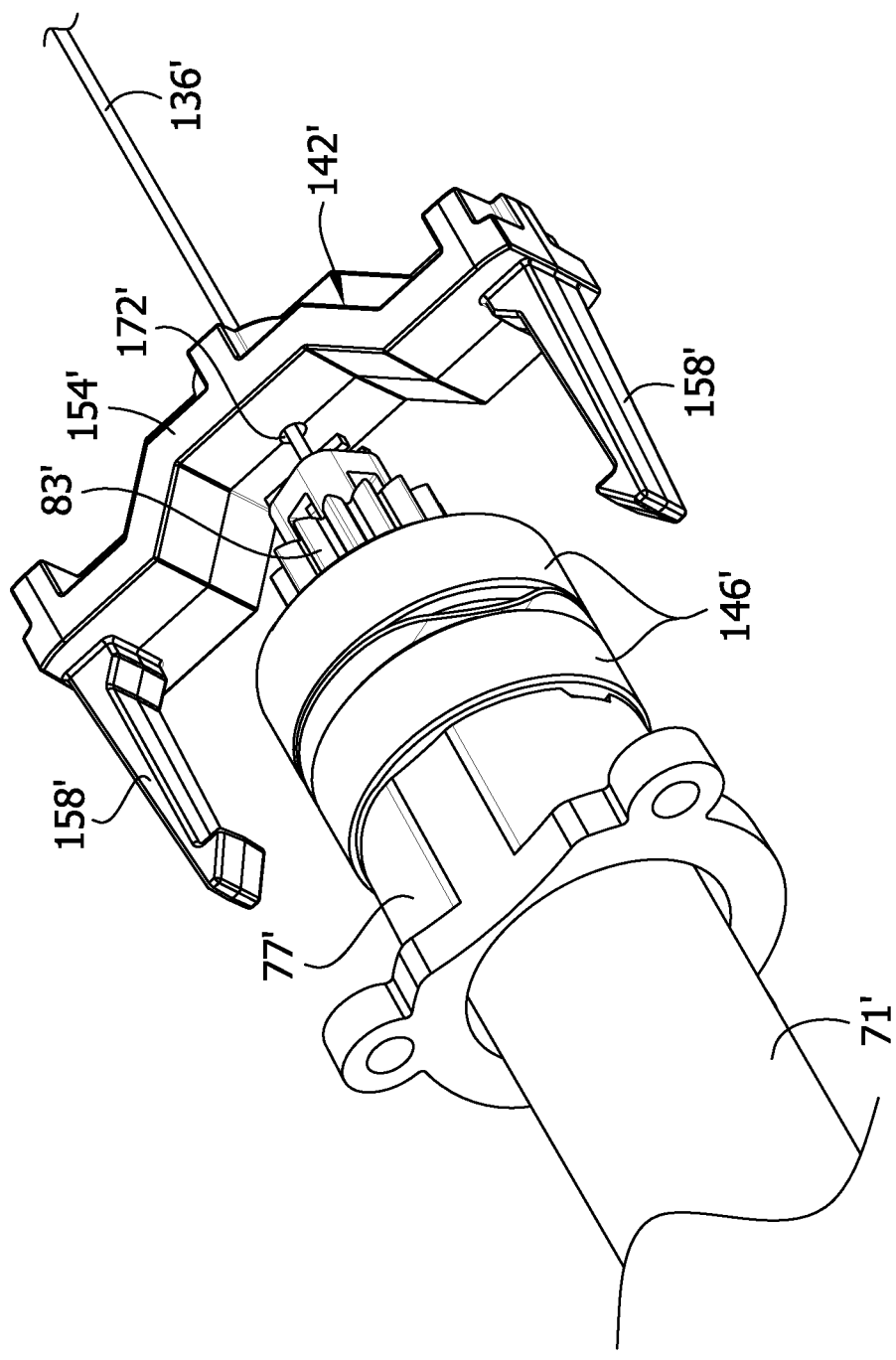
FIG. 55 is an enlarged fragmentary perspective of FIG. 54.
Figure 56:
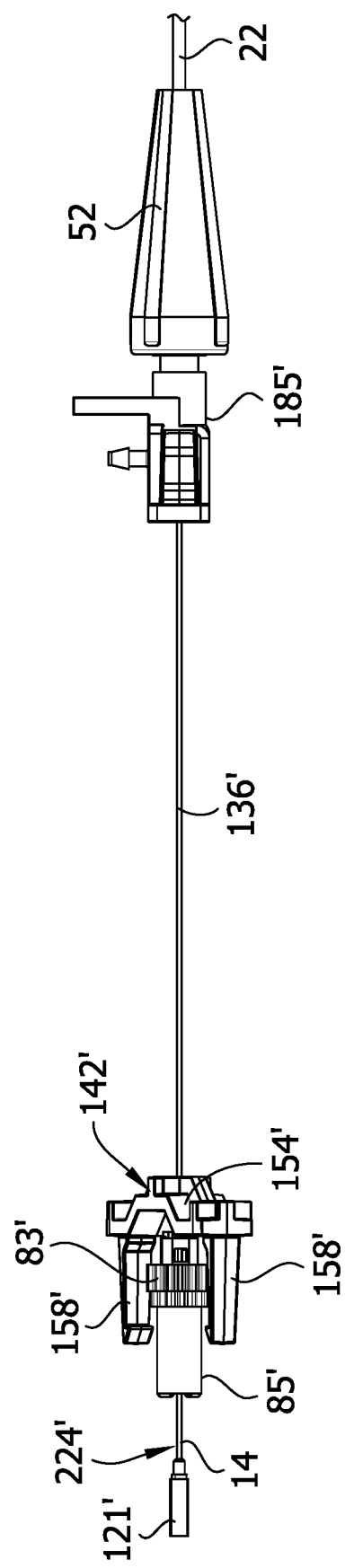
FIG. 56 is a side view of components of the handle and catheter assembly.
Figure 57:
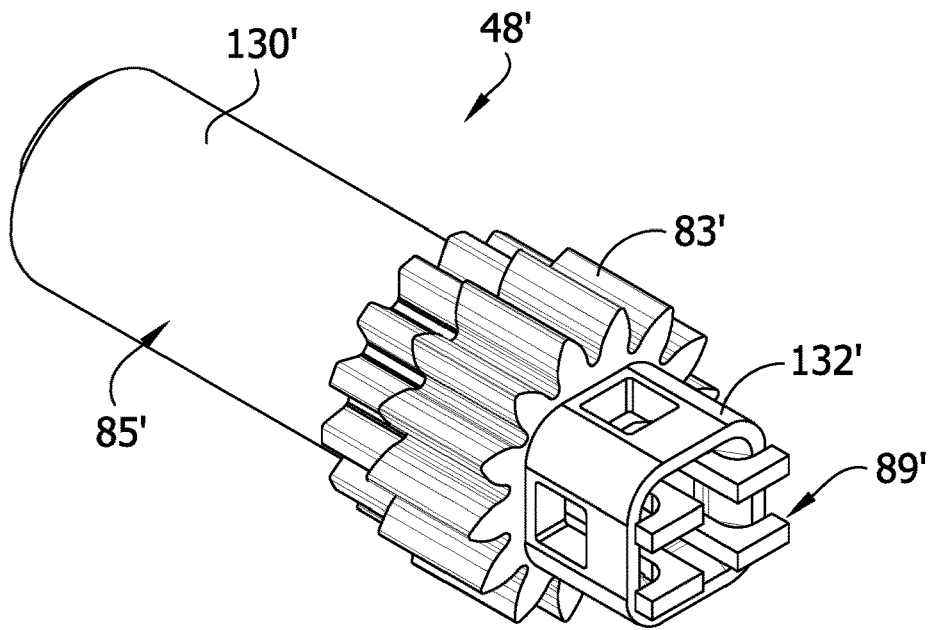
FIG. 57 is a perspective of a driven gear and a drive assembly in the handle.
Figure 58:
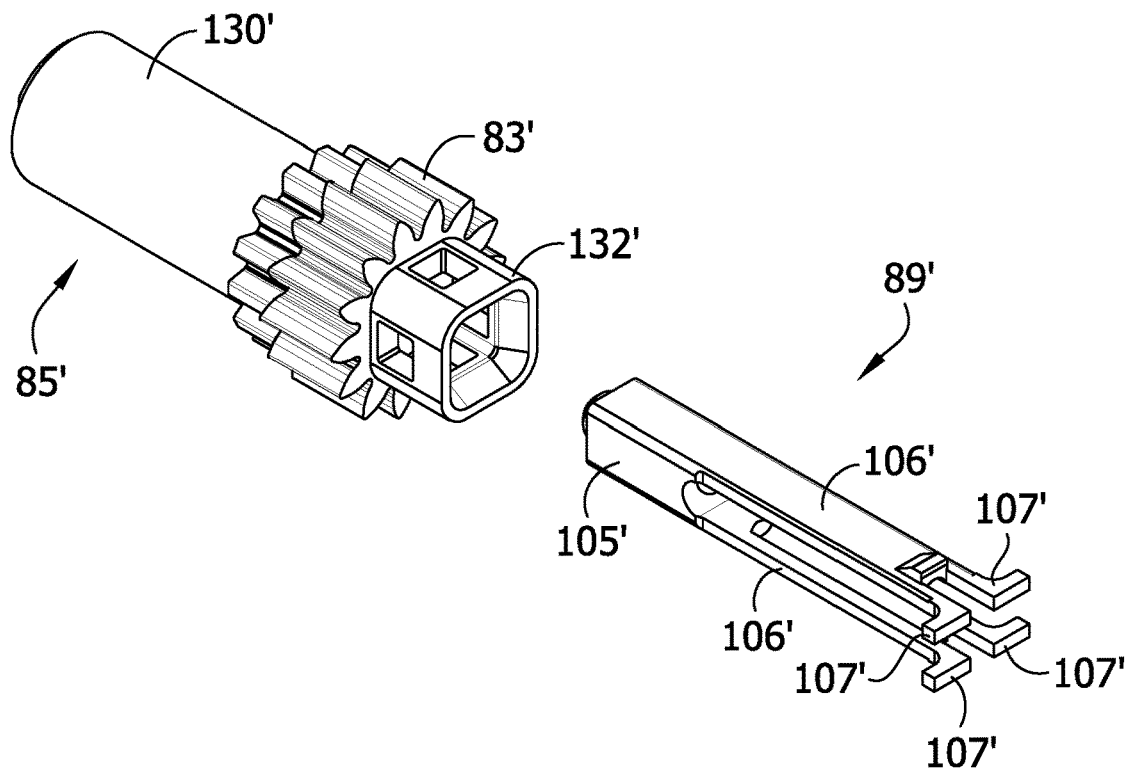
FIG. 58 is an exploded view of the driven gear and drive assembly of FIG. 57.
Figure 59:
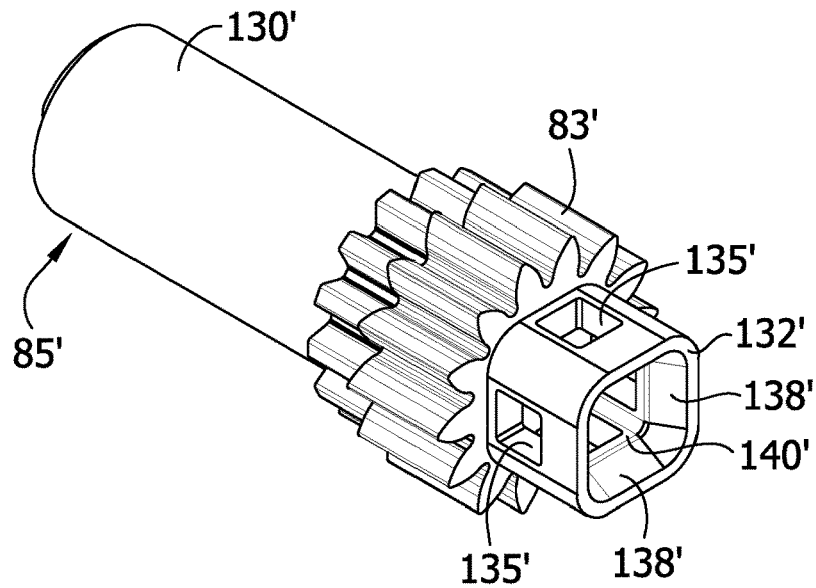
FIG. 59 is a perspective of the driven gear and a gear extension of the drive assembly of FIG. 57.
Figure 60:
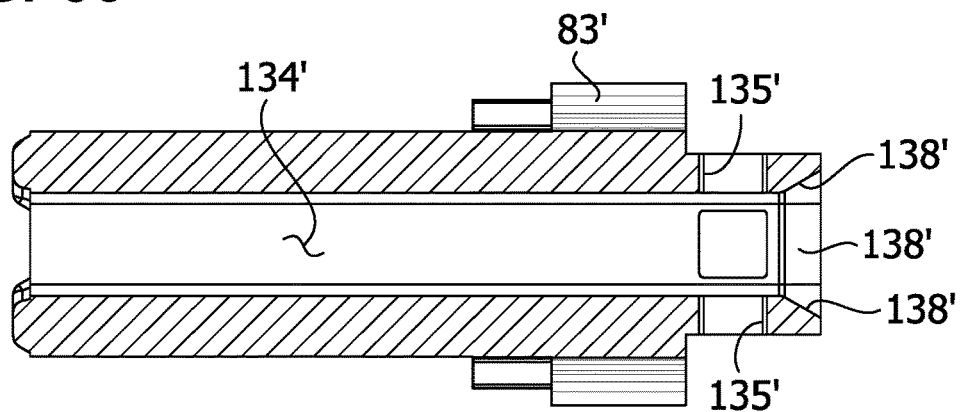
FIG. 60 is a cross section of the driven gear and gear extension of FIG. 59.
Figure 61:
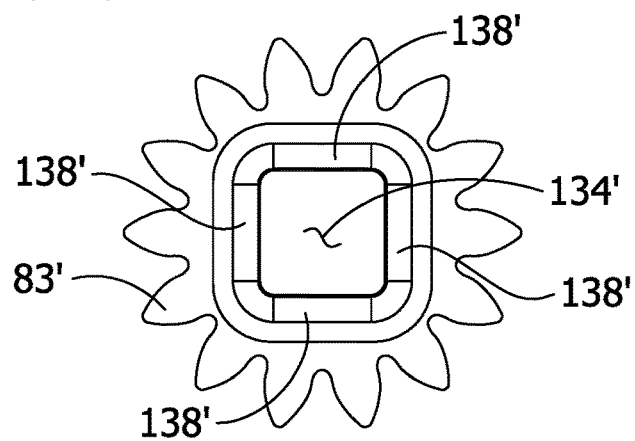
FIG. 61 is an end view of the driven gear and gear extension of FIG. 59.
Figure 62:
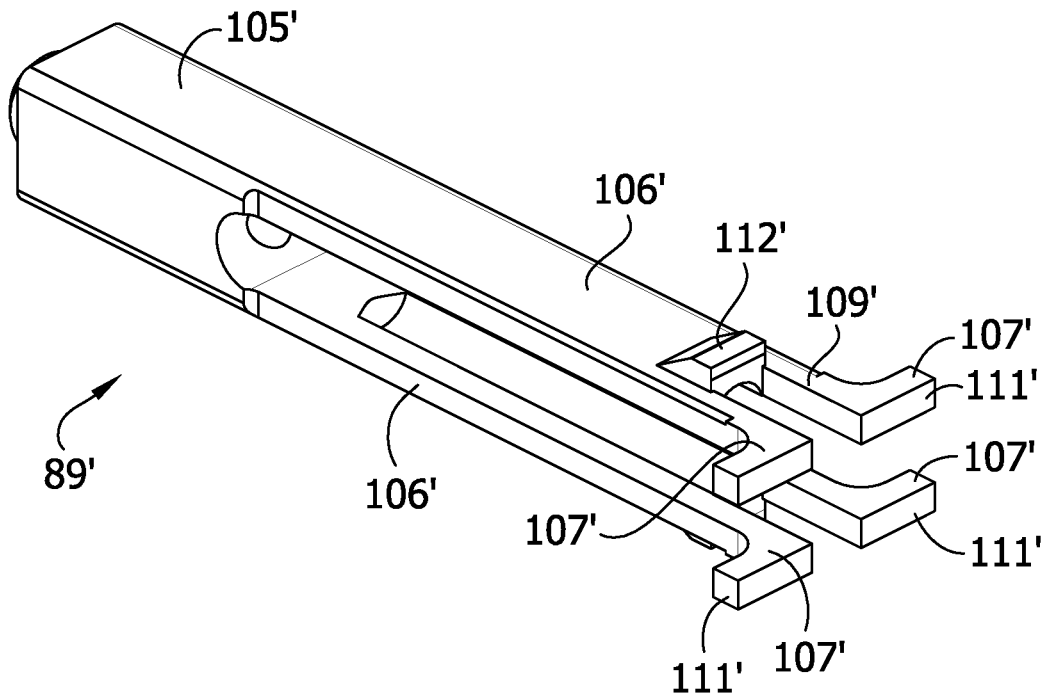
FIG. 62 is a perspective of a gear lock of the drive assembly of FIG. 57.
Figure 63:
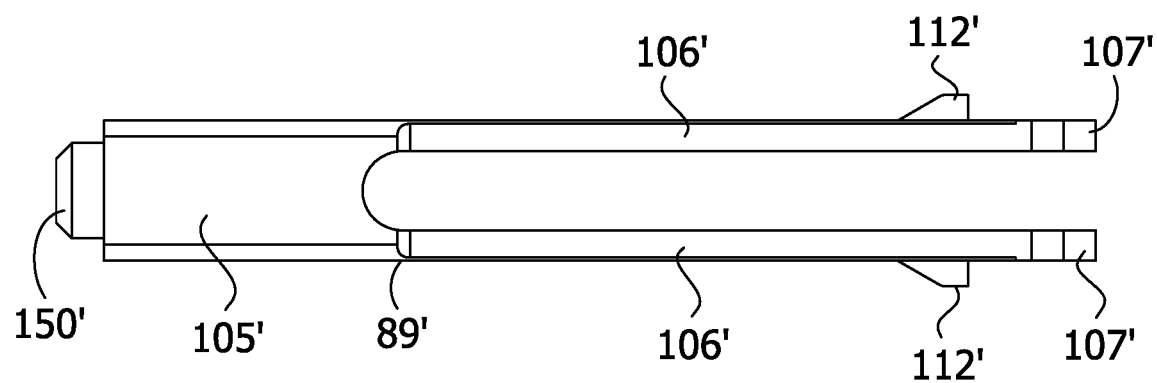
FIG. 63 is a side view of the gear lock of FIG. 62.

Referring to FIGS. 47, 50, and 51, a guidewire port 47' is mounted on a proximal end of the guide tube 223'. The guidewire port 47' provides structure in the handle 40' to support the guidewire at the proximal end of the handle. The guidewire port 47' defines an axial passage 152' through which the guidewire 26 extends. The guidewire port 47' also defines an opening 165' that passes a locking pin 173' of locking the guidewire in place. A flange 167' on a distal end of the guidewire port 47' abuts the proximal end of the guide tube 223' covering at least a portion of a proximal opening of the guide tube. Thus, the flange 167' prevents the liner key 221' from being withdrawn from the proximal end of the guide tube 223'. The passage 152' through the guidewire port 47' communicates an exterior of the handle 40' with the interior of the guide tube 223'. Thus, the guidewire port 47' facilitates flushing of the liner 14 from the proximal end of the handle 40'. In addition, the closer tolerances between the guide tube 223' and the liner key 221' facilitates directing flushing fluid to the liner 14.

Referring to FIGS. 47, 54, and 66-72, the distal end stop 122' is attached to a distal end of the guide tube 223'. In one embodiment, the distal end stop 122' is press fit onto an outer surface of the distal end of the guide tube 223'. However, the distal end stop 122' can be attached to the guide tube 223' by any suitable means. The distal end stop 122' limits the movement of the liner key 221' out of the distal end of the guide tube 223', and is configured to allow the liner key to enter the distal end stop at any entry angle. The distal end stop 122' also centers the guide tube 223' within the buckle tube 71' which in turn centers and aligns the liner 14 within the drive coil 12. Thus, the liner 14 is prevented from being damaged by the drive coil 12 rotating around the liner.

The distal end stop 122' comprises an elongate member having a generally rectangular shape defining four planar side surfaces 174'. The corners of the elongate member are truncated defining four angled corner surfaces 176' connecting adjacent side surfaces 174'. The distal end stop 122' includes a proximal portion 178' and a distal portion 180' extending distally from the proximal portion. In the illustrated embodiment, internal ribs 182' extend along an interior of the proximal portion 178'. The internal ribs 182' provide an engagement surface for press fitting the guide tube 223' in the distal end stop 122'. The proximal portion 178' defines a base of the distal end stop 122' and the distal portion 180' comprises a plurality of extension arms extending from the base. A pair of top and bottom arms 184A' are centered at about mid-width of the distal portion 180' and extend laterally along only a portion of the width of distal portion. Support extensions 190' extend laterally from sides of the top and bottom arms 184A' in opposite directions to opposite sides of the distal portion 180'. The support extensions 190' provide structural rigidity to the top and bottom arms. A pair of side arms 184B' are centered at about mid-height of the distal portion 180' and extend laterally along only a portion of the height of the distal portion. Thus, longitudinal gaps extend between the side arms 184B' and the top and bottom arms 184A'. Free ends of the arms 184A', 184B' project radially inward and together define an interior end surface 192' within the distal end stop 122'. The liner key 221' is configured to engage the interior end surface 192' when the liner 14 is moved distally in the handle 40' preventing the liner key from moving out of the guide tube 223'. Each arm 184A', 184B' also includes angled inlet surfaces 194' that taper radially outward from the interior end surface 192'. The angled surfaces 194' provide inlet guidance at the distal end of the distal end stop 122' so that during assembly the liner key 221' can be inserted into the distal end of the distal end stop at any angle to secure the liner assembly 224' to the guide tube 223' and distal end stop. The side arms 184B' are configured to flex outwardly to provide clearance for inserting the liner key 221'. Once the rectangular member 225' of the liner key 221' is inserted past the free ends of the side arms 184B, the arms will flex back to their natural state capturing the liner key within the distal end stop 122' and preventing the liner key from being pulled back out of the distal end of the distal end stop.

External ribs 196' extend longitudinally along the top and bottom of the distal end stop 122'. Each external rib 196' extends from the proximal portion 178' to the distal portion 180' along the top and bottom arms 184A, respectively. In the illustrated embodiment, the external ribs 196' have a rounded outer surface. Knobs 198' are disposed on the corner surfaces 176' generally between the proximal and distal portions 178', 180'. In the illustrated embodiment, the knobs 198' are domed shaped such that they also have a rounded outer surface. The knobs 198' and external ribs 196' provide an effective circular profile having an effective diameter that provides a close tolerance with the inner diameter of the buckle tube 71' to center the distal end stop 122' within the buckle tube and thereby center the liner key 221' and liner 14 within the buckle tube. Thus, the liner 14 will be centered within the drive coil 12 preventing the liner from being damaged by the drive coil rotating around the liner. It will be understood that the distal end stop 122' could have over shapes without departing from the scope of the disclosure. Additionally or alternatively, the length of the guide tube 223' may be such that the movement of the liner 14 and liner key 221' in the handle 20 is prevented from taking the liner key outside of the guide tube 223' and/or engaging the guidewire port 47' and the distal end stop 122'.

Referring to FIGS. 47, 49, 52, and 54-56, a travel sheath interface assembly 134' is mounted on the distal side of the front housing section 63' of the gearbox housing 55' and secures a travel sheath 136' in the handle 40. Thus, the travel sheath interface assembly 134' joins the travel sheath 136' to the gearbox housing 55' so that the travel sheath moves with the gearbox housing. The travel sheath interface assembly 134' also provides a perfusion seal during advancement and retraction of the catheter components.

The travel sheath interface assembly 134' comprises a travel sheath connector 142' attached to a distal end of the distal sleeve portion 77' of the front housing section 63' of the gearbox housing 55'. The travel sheath connector 142' includes a plate portion 154' and a pair of arms 158' at the periphery of the plate portion that extend proximally from the plate portion. The travel sheath connector 142' is snap fit onto the distal sleeve portion 77' of the front housing section 63' of the gearbox housing 55'. This facilitates removal of the travel sheath connector 142' from the distal sleeve portion 77' with a sufficient distal puling force. A passage 172' extends through the travel sheath interface assembly 134 and receives the travel sheath 136'. The travel sheath 136' is sized to receive the drive coil 12 within an interior of the travel sheath and extends from the travel sheath interface assembly 134' to isolation sheath interface assembly 185'. The travel sheath 136' protects the drive coil 12 and keeps the coil axially aligned during rotation. In one embodiment, the travel sheath connector 142' is overmolded on the travel sheath 136.

Referring to FIGS. 46, 47-50, 53, 56, 73, and 74 an isolation sheath interface assembly 185' is disposed at the distal end of the handle 40'. The assembly 185' comprises an interface housing 187', a lip seal 189' received in a proximal end portion 191' of the interface housing, and a retainer 193' attached to the proximal end of the interface housing to retain the seal to the interface housing. The retainer 193' includes a plate portion 195' and a pair of arms 197' that extend distally from the plate portion. Each arm 197' has a hook 199' at its free end. The arms 197' extend along sides of the proximal end portion 191' of the interface housing 187' and the hooks 199' clip around a distal end of the proximal end portion to attach the retainer 193' to the interface housing by a snap fit engagement. The interface housing 187' further includes a tab 201' on a top of the housing that is received in a slot 203' in the housing 41'. The interface housing 187' further includes a distal end portion 209' that extends through the distal end of the housing 41'. The engagement of the tab 201' and the distal end portion 209' of the interface housing 187' with the housing 41' of the handle 40' mounts the isolation sheath interface assembly 185' to the handle. The distal end portion 209' also extends into a passage in a hub 52 mounted on the proximal end of the isolation sheath 22 to attach the hub to the handle 40'. The engagement between the housing 41' and the interface housing 187' requires the interface housing to be properly seated within the housing 41' of the handle 40' before the housing components of the handle can be joined together.

The interface housing 187' also defines a longitudinal passage 211' extending from the proximal end of the interface housing to a distal end of the interface housing. The longitudinal passage 211' receives the travel sheath 136' and drive coil 12 at the proximal end of the interface housing, and the drive coil extends entirely through the housing to the distal end of the housing. The longitudinal passage 211' receives the isolation sheath 22 at the distal end of the interface housing 187', and the isolation sheath extends to an intermediate location between the proximal and distal ends of the interface housing. A transverse passage 213' extends from the longitudinal passage 211 to a transverse opening 215' in the interface housing 187'. The interface housing 187' also defines a perfusion port 46' for delivering fluid (e.g. saline) between the drive coil 12 and the isolation sheath 22. The transverse passage 213' extends through the perfusion port 46 and thus communicates the perfusion fluid to the longitudinal passage 211'. Therefore, the transverse passage 213' through port 46' communicates with a space between the isolation sheath 22 and the drive coil 12 for delivering the fluid to the rotating drive coil. In one embodiment, a micro pump 217' (FIGS. 42 and 47) may be connected to a fluid (e.g., saline) bag for pumping the fluid through tubing 200' to the perfusion port. In the illustrated embodiment, the sheath 22, hub 52, and interface housing 187' are formed separately. In one embodiment, the isolation sheath 22, hub 52, and interface housing 187' are formed as one integral unit, such as by overmolding.

When introducing elements of the present invention or the one or more embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above apparatuses, systems, and methods without departing from the scope of the invention, it is intended that all matter contained in the above description and shown in the accompanying drawings shall be interpreted as illustrative and not in a limiting sense.

What is claimed is:

1. A tissue-removing catheter for removing tissue in a body lumen, the tissue-removing catheter comprising:
    a catheter body assembly having an axis and proximal and distal end portions spaced apart from one another along the axis, at least a portion of the catheter body assembly being sized and shaped to be received in the body lumen;
    a handle mounted to the proximal end portion of the catheter body assembly and operable to cause rotation of the catheter body assembly, the handle including internal handle components that interface with the catheter body assembly, the internal handle components providing at least four interface locations spaced axially along the catheter body assembly; and
    a tissue-removing element mounted on the distal end portion of the catheter body assembly, the tissue-removing element being configured to remove the tissue as the tissue-removing element is rotated by the catheter body assembly within the body lumen;
    wherein the catheter body assembly includes a rotatable elongate body configured to rotate relative to the handle and sized and shaped to be received within the body lumen, an inner liner assembly movable relative to the rotatable elongate body and having a portion of which received within the rotatable elongate body and defining a guidewire lumen, the internal handle components interfacing with the inner liner assembly and rotatable elongate body of the catheter body assembly, the internal handle components interfacing with the inner liner assembly to permit sliding movement of the inner liner assembly and prevent rotational movement of the inner liner assembly.

2. The tissue-removing catheter as set forth in claim 1, wherein the catheter body assembly includes an isolation sheath disposed around a section of the elongate body, one of the internal handle components interfacing with the isolation sheath of the catheter body assembly.

3. The tissue-removing catheter as set forth in claim 2, wherein the internal handle components comprise a guide tube interfacing with the inner liner assembly, a drive assembly interfacing with the elongate body, a travel sheath interface assembly interfacing with the elongate body, and an isolation sheath interface assembly interfacing with the isolation sheath.

4. The tissue-removing catheter as set forth in claim 3, further comprising a gear assembly in the handle, wherein the drive assembly comprises a gear extension extending from the gear assembly, and a lock secured to the gear extension, the drive assembly being configured to transfer rotation from the gear to the elongate body.

5. The tissue-removing catheter as set forth in claim 4, wherein the travel sheath interface assembly comprises a connector and a travel sheath fixedly attached to the connector and extending around the elongate body.

6. The tissue-removing catheter as set forth in claim 5, further comprising a gear housing enclosing at least a portion of the gear assembly, the connector being attached to the gear housing.

7. The tissue-removing catheter as set forth in claim 3, wherein the isolation sheath interface assembly comprises an interface housing receiving a proximal end of the isolation sheath.

8. The tissue-removing catheter as set forth in claim 3, wherein the inner liner assembly comprises an inner liner and a liner key attached to a proximal end of the inner liner, the guide tube receiving the liner key in a non-rotational, sliding engagement.

9. The tissue-removing catheter as set forth in claim 8, further comprising a distal end stop attached to a distal end of the guide tube for limiting movement of the inner liner assembly out of the guide tube.

10. A handle of a tissue-removing catheter for removing tissue in a body lumen, the handle being operable to cause rotation of a catheter body assembly of the tissue-removing catheter, the handle comprising a housing and internal handle components within the housing configured to interface with the catheter body assembly, the internal handle components providing at least four interface locations spaced axially along the catheter body assembly, wherein the internal handle components are positioned and arranged to interface with an inner liner assembly and a rotatable elongate body of the catheter body assembly configured to rotate relative to the handle, the inner liner assembly being movable relative to the rotatable elongate body and having a portion of which received within the rotatable elongate body and defining a guidewire lumen, wherein the internal handle components interface with the inner liner assembly to permit sliding movement of the inner liner assembly and prevent rotational movement of the inner liner assembly.

11. The handle as set forth in claim 10, wherein one of the internal handle components are positioned and arranged to interface with an isolation sheath of the catheter body assembly.

12. The handle as set forth in claim 11, wherein the internal handle components comprise a guide tube configured to interface with the inner liner assembly, a drive assembly configured to interface with the elongate body, a travel sheath interface assembly configured to interface with the elongate body, and an isolation sheath interface assembly configured to interface with the isolation sheath.

13. The handle as set forth in claim 12, wherein the drive assembly comprises a gear extension and a lock secured to the gear extension, the drive assembly being configured to impart rotation to the elongate body.

14. The handle as set forth in claim 12, wherein the travel sheath interface assembly comprises a connector and a travel sheath fixedly attached to the connector.

15. The handle as set forth in claim 14, further comprising a gear assembly and a gear housing enclosing at least a portion of the gear assembly, the connector being attached to the gear housing.

16. The handle as set forth in claim 12, wherein the isolation sheath interface assembly comprises an interface housing configured to receive a proximal end of the isolation sheath.

17. The handle as set forth in claim 12, wherein the guide tube is configured to receive the inner liner assembly in a non-rotational, sliding engagement.

18. The handle as set forth in claim 12, further comprising a distal end stop attached to a distal end of the guide tube for limiting movement of the inner liner assembly out of the guide tube.

19. A tissue-removing catheter for removing tissue in a body lumen, the tissue-removing catheter comprising:
  a catheter body assembly including a rotatable elongate body having an axis and proximal and distal end portions spaced apart from one another along the axis, the rotatable elongate body being sized and shaped to be received in the body lumen, and a liner assembly movably received within the rotatable elongate body and defining a guidewire lumen, the liner assembly isolating an interior of the guidewire lumen from the rotatable elongate body such that rotational and torsional forces are not transferred from the rotatable elongate body to the interior of the guidewire lumen when the rotatable elongate body is rotated during operation of the tissue-removing catheter; and
  a handle mounted to the proximal end portion of the catheter body assembly and operable to cause rotation of the rotatable elongate body relative to the handle, the handle including internal handle components interfacing with the liner assembly and rotatable elongate body to stabilize the liner assembly and rotatable elongate body and align the liner assembly within the rotatable elongate body for facilitating the isolation of the interior of the guidewire lumen of the liner assembly from the rotatable elongate body;
  wherein the internal handle components interface with the liner assembly to permit sliding movement of the liner assembly and prevent rotational movement of the liner assembly.

20. A tissue-removing catheter for removing tissue in a body lumen, the tissue-removing catheter comprising:
  a catheter body assembly having an axis and proximal and distal end portions spaced apart from one another along the axis, at least a portion of the catheter body assembly being sized and shaped to be received in the body lumen;
  a handle mounted to the proximal end portion of the catheter body assembly and operable to cause rotation of the catheter body assembly, the handle including internal handle components that interface with the catheter body assembly, the internal handle components providing at least four interface locations spaced axially along the catheter body assembly; and
  a tissue-removing element mounted on the distal end portion of the catheter body assembly, the tissue-removing element being configured to remove the tissue as the tissue-removing element is rotated by the catheter body assembly within the body lumen;
  wherein the catheter body assembly includes a rotatable elongate body configured to rotate relative to the handle and sized and shaped to be received within the body lumen, an inner liner assembly movable relative to the rotatable elongate body and having a portion of which received within the rotatable elongate body and defining a guidewire lumen, the internal handle components interfacing with the inner liner assembly and rotatable elongate body of the catheter body assembly; and wherein the internal handle components comprise a drive assembly interfacing with the elongate body, and a gear assembly in the handle, the drive assembly comprising a gear extension extending from the gear assembly, and a lock secured to the gear extension, the drive assembly being configured to transfer rotation from the gear to the elongate body.

* * * * *